(12) United States Patent
Finer et al.

(10) Patent No.: US 6,545,004 B1
(45) Date of Patent: Apr. 8, 2003

(54) METHODS AND COMPOSITIONS UTILIZING QUINAZOLINONES

(75) Inventors: Jeffrey T. Finer, Foster City, CA (US); Gustave Bergnes, Pacifica, CA (US); Whitney W. Smith, El Cerrito, CA (US); John C. Chabala, Mountainside, NJ (US); Bainian Feng, Foster City, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 09/699,047

(22) Filed: Oct. 24, 2000

Related U.S. Application Data

(60) Provisional application No. 60/198,253, filed on Oct. 27, 1999, and provisional application No. 60/213,104, filed on Jun. 21, 2000.

(51) Int. Cl.[7] ...................... A01N 43/54; A61K 31/517; C07D 419/00; C07D 239/72
(52) U.S. Cl. ................. 514/266.2; 514/266.3; 544/284; 544/287
(58) Field of Search .............. 514/266.3, 266.2; 544/284, 287

(56) References Cited

U.S. PATENT DOCUMENTS

| 3,320,124 A | 5/1967 | Waletzky et al. ............ 167/53 |
| 3,322,756 A | 5/1967 | Ruschig et al. .......... 260/247.2 |

(List continued on next page.)

FOREIGN PATENT DOCUMENTS

| DE | 3721855 A1 | 9/1988 | |
| DE | 3721855 A1 | 9/1988 | ............ C07K/5/02 |
| EP | 056637 A1 | 1/1982 | |
| EP | 0056637 A1 | 7/1982 | ......... C07D/239/91 |
| EP | 360417 A2 A3 | 3/1990 | |
| EP | 0884310 A1 | 12/1998 | |
| EP | 884316 A1 | 12/1998 | |
| EP | 884319 A2 A3 | 12/1998 | |
| EP | 900568 A2 | 3/1999 | ......... A61K/31/505 |
| EP | 0903344 A1 | 3/1999 | ......... C07D/239/90 |
| GB | 2271111 A | 4/1994 | ......... C07D/239/90 |
| WO | WO 94/21259 | 9/1994 | |
| WO | WO95/24379 | 9/1995 | |
| WO | WO96/06616 | 3/1996 | |
| WO | WO 96/19224 | 6/1996 | |
| WO | WO 9710221 | 3/1997 | ......... C07D/239/88 |
| WO | WO 97/43276 | 11/1997 | |
| WO | 98/26664 | * 6/1998 | |
| WO | WO 98/34613 | 8/1998 | |
| WO | WO00/07017 | 2/2000 | |
| WO | WO 01/74344 A2 | 10/2000 | .......... A61K/31/00 |
| WO | WO01/16114 A2 | 3/2001 | |
| WO | WO 01/23364 | 4/2001 | |
| WO | WO 01/23365 | 4/2001 | |
| WO | WO 01/25235 | 4/2001 | |
| WO | WO 01/42216 | 6/2001 | |
| WO | WO 01/52234 | 7/2001 | |
| WO | WO 01/66519 | 9/2001 | |

OTHER PUBLICATIONS

Singh et. al., Chem. Abstract, 1980, vol. 92, Abstract No. 58712.*

(List continued on next page.)

Primary Examiner—Richard L. Raymond
Assistant Examiner—Tamthom N. Truong
(74) Attorney, Agent, or Firm—Lauren L. Stevens; Beyer Weaver & Thomas, LLP

(57) ABSTRACT

Quinazolinones of formulae 1a, 1b, 1c and 1d are disclosed. They are useful for treating cellular proliferative diseases and disorders associated with KSP kinesin activity.

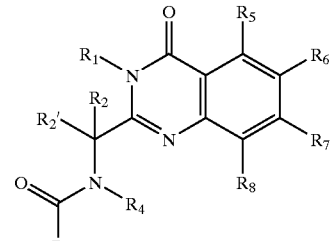

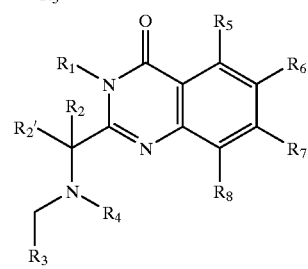

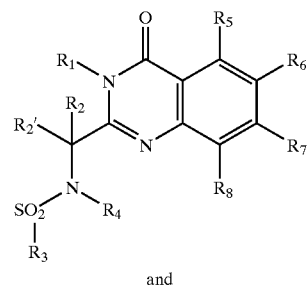

and

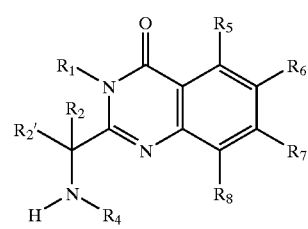

22 Claims, 90 Drawing Sheets

U.S. PATENT DOCUMENTS

| | | | |
|---|---|---|---|
| 3,723,432 A | 3/1973 | Ott | 260/251 |
| 3,740,442 A | 6/1973 | Ott et al. | 424/330 |
| 3,925,548 A | 12/1975 | Oh | 424/251 |
| 4,729,996 A | 3/1988 | Wright et al. | 514/215 |
| 4,808,590 A | 2/1989 | Higa et al. | 514/272 |
| 4,857,530 A | 8/1989 | Berman et al. | 514/259 |
| 4,866,084 A | 9/1989 | Gunasekera et al. | 514/397 |
| 4,970,226 A | 11/1990 | Sun et al. | 514/397 |
| 4,981,856 A | 1/1991 | Hughes | 514/259 |
| 4,992,550 A | 2/1991 | Hughes | 544/284 |
| 5,037,829 A | 8/1991 | Freyne et al. | 514/259 |
| 5,081,124 A | 1/1992 | Hughes | 514/259 |
| 5,147,875 A | 9/1992 | Coates et al. | 514/259 |
| 5,187,167 A | 2/1993 | Hughes | 514/259 |
| 5,204,354 A | 4/1993 | Chakravarty et al. | 514/259 |
| 5,280,027 A | 1/1994 | Andrew et al. | 514/259 |
| 5,316,906 A | 5/1994 | Haugland et al. | 435/4 |
| 5,430,148 A | 7/1995 | Webber et al. | 544/238 |
| 5,449,678 A | 9/1995 | Pines et al. | 514/259 |
| 5,470,878 A | 11/1995 | Michnick et al. | 514/558 |
| 5,561,133 A | 10/1996 | Bisset et al. | 514/259 |
| 5,574,057 A | 11/1996 | Ireland et al. | 514/390 |
| 5,707,992 A | 1/1998 | Webber et al. | 514/253 |
| 5,714,493 A | 2/1998 | Myers et al. | 514/259 |
| 5,747,498 A | 5/1998 | Schnur et al. | 514/259 |
| 5,753,664 A | 5/1998 | Aono et al. | 214/258 |
| 5,756,450 A | 5/1998 | Hahn et al. | 514/9 |
| 5,756,502 A | 5/1998 | Padia et al. | 514/259 |
| 5,756,510 A | 5/1998 | Griffin et al. | 514/261 |
| 5,770,595 A | 6/1998 | Klein et al. | 514/263 |
| 5,773,476 A | 6/1998 | Chen et al. | 514/620 |
| 5,777,115 A | 7/1998 | Leigh et al. | 544/242 |
| 5,780,476 A | 7/1998 | Underiner et al. | 514/263 |
| 5,783,577 A | 7/1998 | Houghten et al. | 514/247 |
| 5,789,427 A | 8/1998 | Chen et al. | 514/352 |
| 5,795,898 A | 8/1998 | Brown et al. | 514/263 |
| 5,801,181 A | 9/1998 | Michnick et al. | 514/269 |
| 5,801,182 A | 9/1998 | Klein et al. | 514/269 |
| 5,804,584 A | 9/1998 | Underiner et al. | 514/269 |
| 5,807,861 A | 9/1998 | Klein et al. | 514/263 |
| 5,807,862 A | 9/1998 | Klein et al. | 514/269 |
| 5,811,429 A | 9/1998 | Connell et al. | 514/259 |
| 5,817,662 A | 10/1998 | Klein et al. | 514/263 |
| 5,837,703 A | 11/1998 | Kumar et al. | 514/183 |
| 5,852,024 A | 12/1998 | Pines et al. | 514/259 |
| 5,859,018 A | 1/1999 | Brown et al. | 514/263 |
| 5,869,665 A | 2/1999 | Padia et al. | 544/236 |
| 5,885,996 A | 3/1999 | Webber et al. | 514/253 |
| 5,891,879 A | 4/1999 | Nagler et al. | 514/259 |
| 5,922,866 A | 7/1999 | Miyata et al. | 544/244 |
| 5,929,081 A | 7/1999 | Brown et al. | 514/263 |
| 6,136,812 A | * 10/2000 | Chenard et al. | 514/259 |

OTHER PUBLICATIONS

Spirkova et. al., Chem. Abstract, 1999, vol. 132, Abstract No. 35672.*

Pandey et. al., Chem. Abstract, 1996, vol. 124, Abstract No. 331723.*

Parasharya et. al., Chem. Abstract, 1994, vol. 121, Abstract No. 108675.*

Saari et. al., Chem. Abstract, 1992, vol. 117, Abstract No. 191731.*

Faraghaly et. al., Chem. Abstract, 1991, vol. 114, Abstract No. 122242.*

El–Nasser Ossman et. al., Chem. Abstract, 1987, vol. 106, Abstract No. 207516.*

Rao et. al., Chem. Abstract, 1986, vol. 105, Abstract No. 97416.*

Kumar et. al., Chem. Abstract, 1985, vol. 102, Abstract No. 1428000.*

Chaurasia et. al., Chem. Abstract, 1982, vol. 96, Abstract No. 6681.*

Tani et. al., Chem. Abstract, 1980, vol. 93, Abstract No. 26374.*

Ager et. al., Chem. Abstract, 1977, vol. 86, Abstract No. 83505.*

Gupta et. al., Chem. Abstract, 1968, vol. 69, Abstract No. 42637.*

A.K. Debnath, "Structure Based Identification of Small Molecule Antiviral Compounds", Journal of Medicinal Chemistry, vol. 42, No. 17, Aug. 1999, pp. 3203–3209.

Bocakei, Zaolt, "Two Antithrombotic Quinazolone Derivatives," Chemical Abstracts, vol. 122, No. 26, Abstract No. 327093n, p. 994, 1995.

Szabo, Monika, "Synthesis of Potential CCK Antagonist Quinazolone," Chemical Abstracts, vol. 124, No. 13, Abstract No. 176002v, pp. 175–181, 1995.

Ager et al., "Synthesis and Central Nervous System Activity of Quinazolones Related to 2–Methyl–3–(o–tolyl)–4(3H)–quinazolone (Methaqualone)", Jrnl of Med. Chem., (1977) vol. 20, No. 3, pp. 379–386.

AU–A–12617/88, Australian patent application "New N–substd. Omega–aminoacid derives.—which are selective inhibitors of human plasma renin" (1988), Derwent Abstract.

Tiwari et al., "Synthesis and CNS Activity of 2–Aryl–3(3', 4'–Dihydroxyphenylethyl) 6–8–substituted–4 (3H)–Quinazolinones", Indian Jrnl of Pharm. Sciences, Mar./Apr. 1978, pp. 40–43.

Rao et al., "Synthesis and Biological Activities of Certain Derivatives of 3–Arl–4(3H)–quinazolinones. Part–II", J. Indian Chem. Soc., vol. LXII, Mar. 1985, pp. 234–237.

CHEMCATS Copyright 2000 ACS, 1998:596123 CHEMCATS, Maybridge, Apr. 3, 2000, DP 01489, N2–(3–pyriaylme~hyl)–4–oxo–3, 4–dihydroquinazoline–2–c~rboxamide, 190437–46–8, Chemical Library.

Q Kozhevnikov, V. and Pilat, N.V. [4–Ouinazolinones. II. 2–(Aminomethyl)–2–aryl–4–quinazolinones.] (Russian) Tr Perm Sel–Khoz Inst (79):66–72, 1971 CA 78:16128.

Gupta, C.M. et al. Drugs acting on the central nervous system. Synthesis of substituted quinazolones and quinazolines and triazepino– and triazocinoquinazolones. J Med Chem 11 :392.395, 1968.

Saari. W .S. et al. Synthesis and evaluation of 2–pyridinone derivatives as HIV–1–specific reverse transcriptase inhibitors. 2. Analogues of 2–aminopyrjdin–2(' H)–one. J Med Chem 35:3792.3802.1992.

Farghaly, A.M. et al. Non–steroidal antiinflammatory agents. Ill: Synthesis of pyrazole derivatives of 4(3H)–quinazolinones. Alexandria J Pharm Sci 4(1):52.56, 1990. CA 114:122242.

Dymek. W. et al. 2–Chloromethyl–6–methylquinazoline–4 and its transformations/ Diss Pharm et Pharmacol 20(1):29–34, 1968.

Pattanaik, J.M. et af. Synthesis and fungicidal activity of 3–aryl.2.(4'.aryl thjazol–2'–ylamunomethyl) quinazol–4(3H)–ones. Indian J Chem 37B:1304–1306, 1998.

Gupta, D.P. and Shanker, K. Thiazolidinones. azetidinones and formazans of quinazolinones. Indian J Chem 26B:1197–1199. 1987.

Parasharya, P.M. and Parikh, A.R. 4–(3H)–Quinazolones part I: 2.Alkyl/arylaminomethyl–3. p–hydroxy/methoxyphenyl.4(3H).quinazolones. J Inst Chemists (India) 64: 184–185, 1992.

Parasharya, P.M. et af. 4(3H)–Q~inaZOlones: 2–N–aryValkyl–amino–methyVethyl–3–p–hydroxyphenyll p–anisyl/p–aryaminoacyloxyphenyl/p–N–arylcarbamoylmethoxyphenyl–4(3H)–quinazolones. J Inst Chemists (India) 64:238–24'.1992.

Matthews. N. et al. Structure–activity relationships of phenothiazines in inhibiting lymphocyte motility as determined by a novel flow cytometric assay. Biochem Pharmacol 50(7):1053–1061.1995.

List of Purchased Compounds 10/00.

* cited by examiner

Figure 2
Step 1: 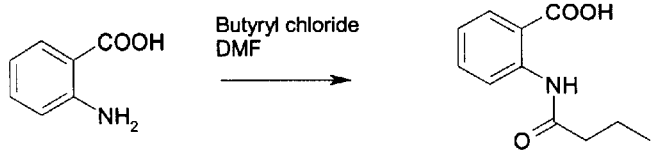
Step 2: 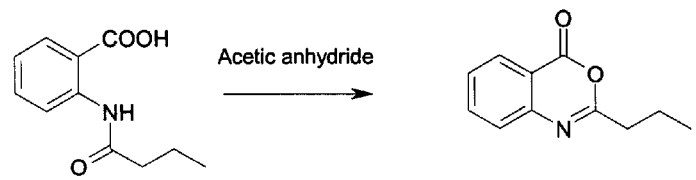
Step 3: 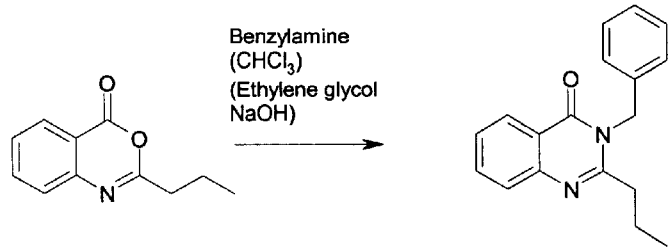
Step 4: 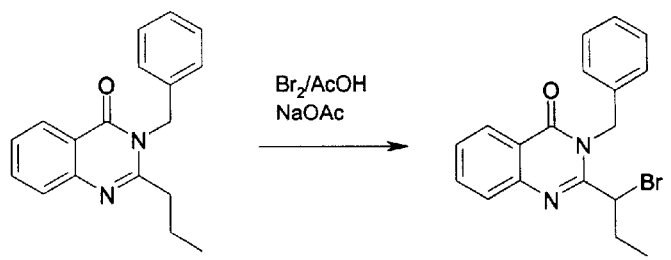
Step 5: 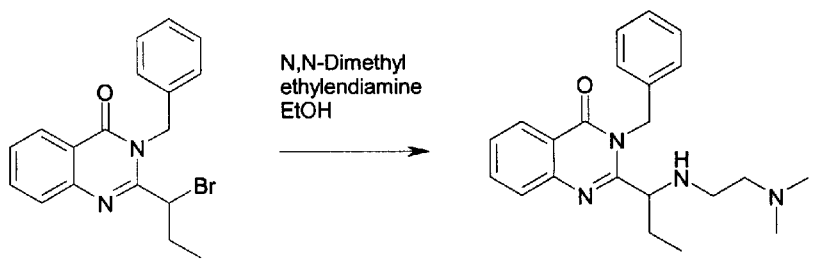
Step 6: 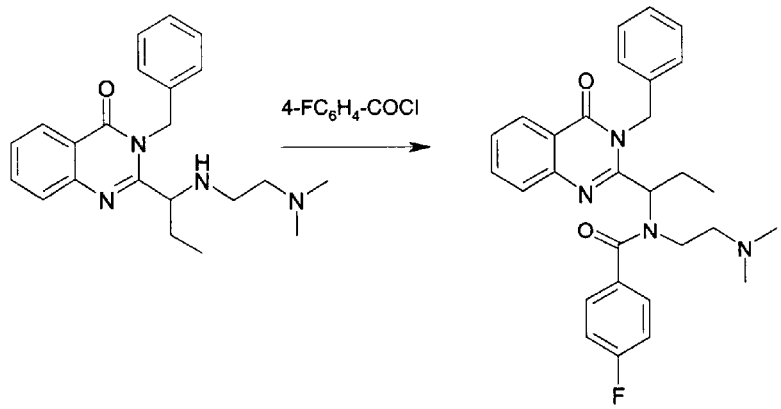

Figure 3A-2

| R₁ | R₂ | R₃ | R₄ | R₅ | R₆ | R₇ | R₈ | Activity |
|---|---|---|---|---|---|---|---|---|
| CH₃–X₁ | H₃C–X₂ | X₃–C₆H₄–Cl (para) | X₄–CH₂CH₂–N(CH₃)₂ | | X₆–Cl | | | %I > 35% @ 40 uM |
| CH₃–X₁ | H₃C–X₂ | X₃–C₆H₄–CH₃ (para) | X₄–CH₂CH₂–N(CH₃)₂ | | X₆–Cl | | | %I > 35% @ 40 uM |
| H₃C–X₁ | H₃C–X₂ | H₃C–(CH₂)ₙ–X₃ (long alkyl chain) | X₄–CH₂CH₂–N(CH₃)₂ | | | | | %I > 35% @ 40 uM |
| CH₃–O–CH₂CH₂–X₁ | CH₃–X₂ | X₃–naphthyl | H₃C–N(CH₃)–CH₂CH₂–X₄ | | | | | %I > 35% @ 40 uM |
| CH₃–X₁ | H₃C–CH₂–X₂ | X₃–C₆H₃(Cl)₂ (2,4-dichloro) | X₄–CH₂CH₂–N(CH₃)₂ | | | X₇–Cl | | %I > 35% @ 40 uM |

Figure 3A-3

| R₁ | R₂ | R₃ | R₄ | R₅ | R₆ | R₇ | R₈ | Activity |
|---|---|---|---|---|---|---|---|---|
| CH₃–X₁ | H₃C–X₂ | X₃–C₆H₄–NO₂ (para) | X₄–CH₂CH₂–N(CH₃)₂ | | | X₇–Cl | | %I > 35% @ 40 uM |
| CH₃–X₁ | H₃C–X₂ | X₃–C₆H₄–F (ortho) | X₄–CH₂CH₂–N(CH₃)₂ | | | X₇–Cl | | %I > 35% @ 40 uM |
| CH₃–X₁ | H₃C–X₂ | X₃–benzo[1,3]dioxole | X₄–CH₂CH₂–N(CH₃)₂ | | | X₇–Cl | | %I > 35% @ 40 uM |
| CH₃–O–X₁ | H₃C–X₂ | X₃–C₆H₄–F (para) | X₄–CH₂CH₂–N(CH₃)₂ | | | | | %I > 35% @ 40 uM |
| CH₃–O–X₁ | H₃C–X₂ | X₃–C₆H₄–F (ortho) | X₄–CH₂CH₂–N(CH₃)₂ | | | | | %I > 35% @ 40 uM |

Figure 3A-4

| R₁ | R₂ | R₃ | R₄ | R₅ | R₆ | R₇ | R₈ | Activity |
|---|---|---|---|---|---|---|---|---|
| CH₃–X₁ | H₃C–X₂ | X₃–⟨C₆H₄⟩–CF₃ (with X₃=N) | X₄–CH₂CH₂–N(CH₃)CH₃ | | | X₇–Cl | | %I > 35% @ 40 uM |
| benzyl–X₁ | H₃C–X₂ | X₃–⟨C₆H₄⟩–F (ortho) | X₄–CH₂CH₂–N(CH₃)CH₃ | | | | | %I > 35% @ 40 uM |
| benzyl–X₁ | H₃C–X₂ | X₃–⟨C₆H₄⟩–Br (meta) | X₄–CH₂CH₂–N(CH₃)CH₃ | | | | | %I > 35% @ 40 uM |
| H₃C–X₁ | H₃C–X₂ | cyclohexyl with CH₃ and X₃ | X₄–CH₂CH₂–N(CH₃)CH₃ | | | X₇–Cl | | %I > 35% @ 40 uM |
| CH₃–X₁ | H₃C–X₂ | X₃–benzo[1,3]dioxole | X₄–CH₃ | | X₆–Cl | | | %I > 35% @ 40 uM |

Figure 3A-5

| R₁ | R₂ | R₃ | R₄ | R₅ | R₆ | R₇ | R₈ | Activity |
|---|---|---|---|---|---|---|---|---|
| ![benzyl-X₁] | H₃C-X₂ | furan-X₃ | X₄-CH₂CH₂-N(CH₃)₂ | | | | | %I > 35% @ 40 uM |
| ![benzyl-X₁] | H₃C-X₂ | X₃-CH₂-C₆H₄-OCH₃ | X₄-CH₂CH₂-N(CH₃)₂ | | | | | %I > 35% @ 40 uM |
| ![benzyl-X₁] | H₃C-X₂ | X₃-C₆H₄-CH₂CH₂CH₃ | X₄-CH₂CH₂-N(CH₃)₂ | | | | | %I > 35% @ 40 uM |
| ![benzyl-X₁] | H₃C-X₂ | X₃-CH=CH-C₆H₅ | X₄-CH₂CH₂-N(CH₃)₂ | | | | | %I > 35% @ 40 uM |

Figure 3A-6

| R$_1$ | R$_2$ | R$_3$ | R$_4$ | R$_5$ | R$_6$ | R$_7$ | R$_8$ | Activity |
|---|---|---|---|---|---|---|---|---|
| | X$_2$—CH$_3$ | 4-methylphenyl-N-X$_3$ (with CH$_3$) | H$_3$C-N(CH$_3$)-CH$_2$CH$_2$-X$_4$ | | | X$_7$—Cl | | %I > 35% @ 40 uM |
| | X$_2$—CH$_3$ | 4-methylphenyl-N-X$_3$ (with CH$_3$) | H$_3$C-N(CH$_3$)-CH$_2$CH$_2$-X$_4$ | | | X$_7$—Cl | | %I > 35% @ 40 uM |
| phenyl-CH$_2$-X$_1$ | H$_3$C-CH$_2$-X$_2$ | phenyl-N-X$_3$ | X$_4$-CH$_2$CH$_2$-N(CH$_3$)-CH$_3$ | | | | | %I > 35% @ 40 uM |
| phenyl-CH$_2$-X$_1$ | H$_3$C-CH$_2$-X$_2$ | 4-methylphenyl-N-X$_3$ | X$_4$-CH$_2$CH$_2$-N(CH$_3$)-CH$_3$ | | | | | %I > 35% @ 40 uM |

| R₁ | R₂ | R₃ | R₄ | R₅ | R₆ | R₇ | R₈ | Activity |
|---|---|---|---|---|---|---|---|---|
| 4-Br-phenyl-X₁ | H₃C-X₂ | X₃-(4-methylphenyl) | X₄-CH₂CH₂-N(CH₃)₂ | | | | | %I > 35% @ 40 uM |
| 4-Br-phenyl-X₁ | H₃C-X₂ | X₃-(4-butylphenyl) | X₄-CH₂CH₂-N(CH₃)₂ | | | | | %I > 35% @ 40 uM |
| 4-Br-phenyl-X₁ | H₃C-X₂ | X₃-(4-methylphenyl) | X₄-CH₂CH₂-N(CH₃)₂ | | | | | %I > 35% @ 40 uM |
| 4-Br-phenyl-X₁ | H₃C-X₂ | X₃-CH=CH-phenyl | X₄-CH₂CH₂-N(CH₃)₂ | | | | | %I > 35% @ 40 uM |
| benzyl-X₁ | X₂-CH₂CH₂-CH₃ | X₃-(3-methoxyphenyl) | X₄-cyclohexyl | | | | | %I > 35% @ 40 uM |

Figure 3A-9

| R1 | R2 | R3 | R4 | R5 | R6 | R7 | R8 | Activity |
|---|---|---|---|---|---|---|---|---|
| CH3-X1 | H3C-X2 | X3-C6H4-Br | X4-CH2CH2-N(CH3)2 | | X6-Cl | | | %I > 35% @ 40 uM |
| CH3-X1 | H3C-X2 | X3-benzodioxole | X4-CH2CH2-N(CH3)2 | | X6-Cl | | | %I > 35% @ 40 uM |
| CH3-CH(CH3)-X1 | CH3-CH(X2)-CH3 | X3-naphthyl | H3C-N(CH3)-CH2CH2-X4 | | | | | %I > 35% @ 40 uM |
| CH3-O-CH2CH2-X1 | H3C-X2 | X3-C6H4-Cl | X4-CH2CH2-N(CH3)2 | | | | | %I > 35% @ 40 uM |
| CH3-X1 | H3C-CH2-X2 | X3-C6H4-CH3 | X4-CH2CH2-N(CH3)2 | | | | | %I > 35% @ 40 uM |

Figure 3A-10

| R₁ | R₂ | R₃ | R₄ | R₅ | R₆ | R₇ | R₈ | Activity |
|---|---|---|---|---|---|---|---|---|
| CH₃–X₁ | H₃C–X₂ (with CH₃) | 3,4-dichlorophenyl-X₃ | X₄–N(CH₃)₂ ethyl | | | | | %I > 35% @ 40 uM |
| CH₃–X₁ | X₂–CH₃ | 2-naphthyl-X₃ | X₄–N(CH₃)₂ with H₃C | | | | | %I > 35% @ 40 uM |
| CH₃–X₁ | H₃C–X₂ | 3-(trifluoromethyl)phenyl-X₃ | X₄–N(CH₃)₂ ethyl | | | | | %I > 35% @ 40 uM |
| CH₃–X₁ | H₃C–X₂ | 4-bromophenyl-X₃ | X₄–N(CH₃)₂ ethyl | | | | | %I > 35% @ 40 uM |
| CH₃–X₁ | H₃C–X₂ | 4-methoxyphenyl-X₃ | X₄–N(CH₃)₂ ethyl | | | X₇–Cl | | %I > 35% @ 40 uM |

Figure 3A-11

| R₁ | R₂ | R₃ | R₄ | R₅ | R₆ | R₇ | R₈ | Activity |
|---|---|---|---|---|---|---|---|---|
| CH₃—X₁ | H₃C—X₂ | 3,5-dimethoxyphenyl-X₃ | X₄—CH₂CH₂—N(CH₃)₂ | | | X₇—Cl | | %I > 35% @ 40 uM |
| CH₃—X₁ | H₃C—X₂ | 3-fluorophenyl-X₃ | X₄—CH₂CH₂—N(CH₃)₂ | | | X₇—Cl | | %I > 35% @ 40 uM |
| CH₃—X₁ | H₃C—X₂ | 4-(butyl)phenyl-X₃ | X₄—CH₂CH₂—N(CH₃)₂ | | | X₇—Cl | | %I > 35% @ 40 uM |
| CH₃—X₁ | H₃C—X₂ | 4-(propyl)phenyl-X₃ | X₄—CH₂CH₂—N(CH₃)₂ | | | X₇—Cl | | %I > 35% @ 40 uM |

Figure 3A-12

| R₁ | R₂ | R₃ | R₄ | R₅ | R₆ | R₇ | R₈ | Activity |
|---|---|---|---|---|---|---|---|---|
| CH₃–X₁ | H₃C–X₂ | X₃–(C₆H₄)–CH₂CH₂CH₂–CH₃ | X₄–CH₂CH₂–N(CH₃)CH₃ | | | X₇–Cl | | %I > 35% @ 40 uM |
| CH₃–X₁ | H₃C–X₂ | X₃–(C₆H₄)–CH₂CH₂–CH₃ | X₄–CH₂CH₂–N(CH₃)CH₃ | | | X₇–Cl | | %I > 35% @ 40 uM |
| CH₃–O–CH₂CH₂–X₁ | H₃C–CH₂–X₂ | X₃–C₆H₅ | X₄–CH₂CH₂–N(CH₃)CH₃ | | | | | %I > 35% @ 40 uM |
| CH₃–O–CH₂CH₂–X₁ | H₃C–CH₂–X₂ | X₃–(C₆H₄)–O–CH₃ | X₄–CH₂CH₂–N(CH₃)CH₃ | | | | | %I > 35% @ 40 uM |

Figure 3A-13

| R₁ | R₂ | R₃ | R₄ | R₅ | R₆ | R₇ | R₈ | Activity |
|---|---|---|---|---|---|---|---|---|
| CH₃-O-\_/\-X₁ | H₃C-\_/\-X₂ | X₃-(3-F-phenyl) | X₄-CH₂CH₂-N(CH₃)CH₃ | | | | | %I > 35% @ 40 uM |
| CH₃-O-\_/\-X₁ | H₃C-\_/\-X₂ | X₃-(3,5-bis-CF₃-phenyl) | X₄-CH₂CH₂-N(CH₃)CH₃ | | | | | %I > 35% @ 40 uM |
| CH₃-O-\_/\-X₁ | H₃C-\_/\-X₂ | X₃-(benzodioxole) | X₄-CH₂CH₂-N(CH₃)CH₃ | | | | | %I > 35% @ 40 uM |
| CH₃-O-\_/\-X₁ | H₃C-\_/\-X₂ | X₃-(3-OCH₃-phenyl) | X₄-CH₂CH₂-N(CH₃)CH₃ | | | | | %I > 35% @ 40 uM |
| Ph-CH₂-X₁ | H₃C-X₂ | X₃-(3-F-phenyl) | X₄-CH₂CH₂-N(CH₃)CH₃ | | | | | %I > 35% @ 40 uM |

Figure 3A-14

| R₁ | R₂ | R₃ | R₄ | R₅ | R₆ | R₇ | R₈ | Activity |
|---|---|---|---|---|---|---|---|---|
| H₃C—X₁ | H₃C—X₂ | X₃-(4-Cl-phenyl) | X₄-CH₂CH₂-N(CH₃)₂ | | | X₇—Cl | | %I > 35% @ 40 uM |
| H₃C—X₁ | H₃C—X₂ | X₃-(4-CH₃-phenyl) | X₄-CH₂CH₂-N(CH₃)₂ | | | X₇—Cl | | %I > 35% @ 40 uM |
| benzyl-X₁ | H₃C-CH₂-X₂ | X₃-CH₂-phenyl | X₄-CH₂CH₂-N(CH₃)₂ | | | | | %I > 35% @ 40 uM |
| benzyl-X₁ | H₃C-CH₂-X₂ | X₃-(2-F-phenyl) | X₄-CH₂CH₂-N(CH₃)₂ | | | | | %I > 35% @ 40 uM |

Figure 3A-15

| R₁ | R₂ | R₃ | R₄ | R₅ | R₆ | R₇ | R₈ | Activity |
|---|---|---|---|---|---|---|---|---|
| | | | | | | | | %I > 35% @ 40 uM |
| | | | | | | | | %I > 35% @ 40 uM |
| | | | | | | | | %I > 35% @ 40 uM |
| | | | | | | | | %I > 35% @ 40 uM |

Figure 3A-16

| R1 | R2 | R3 | R4 | R5 | R6 | R7 | R8 | Activity |
|---|---|---|---|---|---|---|---|---|
| 4-Cl-phenyl-X1 | H3C-X2 | 4-propyl-phenyl-X3 | X4-CH2CH2-N(CH3)2 | | | | | %I > 35% @ 40 uM |
| 4-Cl-phenyl-X1 | H3C-X2 | 4-methyl-phenyl-X3 | X4-CH2CH2-N(CH3)2 | | | | | %I > 35% @ 40 uM |
| 4-Cl-phenyl-X1 | H3C-CH2-X2 | phenyl-X3 | X4-CH2CH2-N(CH3)2 | | | | | %I > 35% @ 40 uM |
| 4-Cl-phenyl-X1 | H3C-CH2-X2 | 4-Cl-phenyl-X3 | X4-CH2CH2-N(CH3)2 | | | | | %I > 35% @ 40 uM |

Figure 3A-17

| R₁ | R₂ | R₃ | R₄ | R₅ | R₆ | R₇ | R₈ | Activity |
|---|---|---|---|---|---|---|---|---|
| 4-Cl-C₆H₄-X₁ | H₃C-CH₂-X₂ | 4-CH₃-C₆H₄-X₃ | X₄-CH₂CH₂-N(CH₃)₂ | | | | | %I > 35% @ 40 uM |
| 4-Cl-C₆H₄-X₁ | H₃C-CH₂-X₂ | 3-F-C₆H₄-X₃ | X₄-CH₂CH₂-N(CH₃)₂ | | | | | %I > 35% @ 40 uM |
| 4-Cl-C₆H₄-X₁ | H₃C-CH₂-X₂ | 4-Br-C₆H₄-X₃ | X₄-CH₂CH₂-N(CH₃)₂ | | | | | %I > 35% @ 40 uM |
| 4-Cl-C₆H₄-X₁ | H₃C-CH₂-X₂ | 3-OCH₃-C₆H₄-X₃ | X₄-CH₂CH₂-N(CH₃)₂ | | | | | %I > 35% @ 40 uM |
| 4-Cl-C₆H₄-X₁ | H₃C-CH₂-X₂ | 4-CH₃-C₆H₄-X₃ | X₄-CH₂CH₂-N(CH₃)₂ | | | | | %I > 35% @ 40 uM |

Figure 3A-18

| R₁ | R₂ | R₃ | R₄ | R₅ | R₆ | R₇ | R₈ | Activity |
|---|---|---|---|---|---|---|---|---|
| 4-Br-C₆H₄-X₁ | H₃C-X₂ | 3-Br-C₆H₄-X₃ | X₄-CH₂CH₂-N(CH₃)₂ | | | | | %I > 35% @ 40 uM |
| 4-Br-C₆H₄-X₁ | H₃C-X₂ | 3-OCH₃-C₆H₄-X₃ | X₄-CH₂CH₂-N(CH₃)₂ | | | | | %I > 35% @ 40 uM |
| C₆H₅-X₁ | CH₃-CH₂-X₂ | naphthyl-X₃ | H₃C-N(CH₃)-CH₂-X₄ | | | | | %I > 35% @ 40 uM |
| 4-CH₃-C₆H₄-X₁ | H₃C-CH₂-X₂ | C₆H₅-X₃ | X₄-CH₂CH₂-N(CH₃)₂ | | | | | %I > 35% @ 40 uM |
| 4-CH₃-C₆H₄-X₁ | H₃C-CH₂-X₂ | 4-Cl-C₆H₄-X₃ | X₄-CH₂CH₂-N(CH₃)₂ | | | | | %I > 35% @ 40 uM |

Figure 3A-19

| R₁ | R₂ | R₃ | R₄ | R₅ | R₆ | R₇ | R₈ | Activity |
|---|---|---|---|---|---|---|---|---|
| H₃C–⟨⟩–X₁ | H₃C–CH₂–X₂ | X₃–⟨⟩–C(CH₃)₂–CH₃ (with H₃C) | X₄–CH₂CH₂–N(CH₃)(CH₃) | | | | | %I > 35% @ 40 uM |
| H₃C–⟨⟩–X₁ | H₃C–CH₂–X₂ | X₃–⟨⟩–F | X₄–CH₂CH₂–N(CH₃)(CH₃) | | | | | %I > 35% @ 40 uM |
| CH₃–⟨⟩–X₁ (with X₁) | X₂–CH₂–CH₃ | X₃–naphthyl | H₃C–N(CH₃)–CH₂CH₂–X₄ | | | | | %I > 35% @ 40 uM |
| H₃C–⟨⟩–X₁ | H₃C–CH₂–X₂ | X₃–⟨⟩–Br | X₄–CH₂CH₂–N(CH₃)(CH₃) | | | | | %I > 35% @ 40 uM |

Figure 3A-20

| R₁ | R₂ | R₃ | R₄ | R₅ | R₆ | R₇ | R₈ | Activity |
|---|---|---|---|---|---|---|---|---|
| 4-methylphenyl-X₁ | H₃C-X₂ | phenyl-X₃ | X₄-CH₂CH₂-N(CH₃)₂ | | | | | %I > 35% @ 40 uM |
| 4-methylphenyl-X₁ | H₃C-X₂ | 3-fluorophenyl-X₃ | X₄-CH₂CH₂-N(CH₃)₂ | | | | | %I > 35% @ 40 uM |
| 4-methylphenyl-X₁ | H₃C-X₂ | 4-propylphenyl-X₃ | X₄-CH₂CH₂-N(CH₃)₂ | | | | | %I > 35% @ 40 uM |
| 4-methylphenyl-X₁ | H₃C-X₂ | 4-methylphenyl-X₃ | X₄-CH₂CH₂-N(CH₃)₂ | | | | | %I > 35% @ 40 uM |

Figure 3A-21

| R₁ | R₂ | R₃ | R₄ | R₅ | R₆ | R₇ | R₈ | Activity |
|---|---|---|---|---|---|---|---|---|
| 4-methoxyphenyl-X₁ | H₃C-X₂ | X₃-phenyl | X₄-CH₂CH₂-N(CH₃)₂ | | | X₇-Cl | | %I > 35% @ 40 uM |
| 4-methoxyphenyl-X₁ | X₂-CH₃ | X₃-naphthyl | X₄-CH₂CH₂-N(CH₃)₂ | | | Cl-X₇ | | %I > 35% @ 40 uM |
| 4-methoxyphenyl-X₁ | H₃C-X₂ | X₃-phenyl-CH₂CH₂CH₃ | X₄-CH₂CH₂-N(CH₃)₂ | | | X₇-Cl | | %I > 35% @ 40 uM |
| 2,3-dimethylphenyl-X₁ | H₃C-X₂ | X₃-phenyl | X₄-CH₂CH₂-N(CH₃)₂ | | | | | %I > 35% @ 40 uM |

Figure 3A-22

| R₁ | R₂ | R₃ | R₄ | R₅ | R₆ | R₇ | R₈ | Activity |
|---|---|---|---|---|---|---|---|---|
|  |  |  |  | | | | | %I > 35% @ 40 uM |
|  |  |  |  | | | | | %I > 35% @ 40 uM |
| 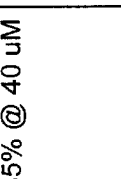 | 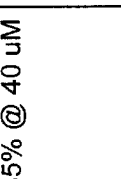 | 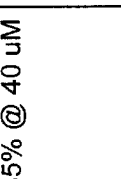 | 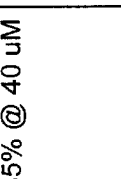 | | | | | %I > 35% @ 40 uM |
|  |  |  |  | | | | | %I > 35% @ 40 uM |
Figure 3A-23

| R1 | R2 | R3 | R4 | R5 | R6 | R7 | R8 | Activity |
|---|---|---|---|---|---|---|---|---|
| 4-Br-phenyl-X1 | H3C-CH2-X2 | 4-Cl-phenyl-X3 | X4-CH2CH2-N(CH3)2 | | | | | %I > 35% @ 40 uM |
| 4-Br-phenyl-X1 | H3C-CH2-X2 | 3,4-diCl-phenyl-X3 | X4-CH2CH2-N(CH3)2 | | | | | %I > 35% @ 40 uM |
| 4-Br-phenyl-X1 | H3C-CH2-X2 | 3-F-phenyl-X3 | X4-CH2CH2-N(CH3)2 | | | | | %I > 35% @ 40 uM |
| 4-Br-phenyl-X1 | H3C-CH2-X2 | 3-Br-phenyl-X3 | X4-CH2CH2-N(CH3)2 | | | | | %I > 35% @ 40 uM |
| 4-Br-phenyl-X1 | H3C-CH2-X2 | 4-Br-phenyl-X3 | X4-CH2CH2-N(CH3)2 | | | | | %I > 35% @ 40 uM |

Figure 3A-24

| R₁ | R₂ | R₃ | R₄ | R₅ | R₆ | R₇ | R₈ | Activity |
|---|---|---|---|---|---|---|---|---|
| 4-Br-C₆H₄-X₁ | H₃C-CH₂-X₂ | 3-OCH₃-C₆H₄-X₃ | X₄-CH₂CH₂-N(CH₃)₂ | | | | | %I > 35% @ 40 uM |
| 2-CH₃-4-Cl-C₆H₃-X₁ | H₃C-CH₂-X₂ | 3-F-C₆H₄-X₃ | X₄-CH₂CH₂-N(CH₃)₂ | | | | | %I > 35% @ 40 uM |
| X₁-CH₂CH₂-C(O)-O-CH₃ | H₃C-X₂ | 3,4-diCl-C₆H₃-N(X₃)₂ | 2-CH₃-C₆H₄-CH₂-X₄ | | | | | %I > 35% @ 40 uM |
| C₆H₅-CH₂-X₁ | X₂-CH₃ | cyclohexyl-N(X₃)- | (CH₃)₃C-X₄ | | | | | %I > 35% @ 40 uM |

Figure 3A-25

| $R_1$ | $R_2$ | $R_3$ | $R_4$ | $R_5$ | $R_6$ | $R_7$ | $R_8$ | Activity |
|---|---|---|---|---|---|---|---|---|
| 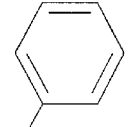 |  | 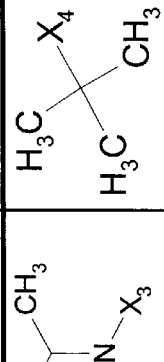 | 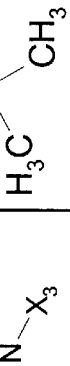 | | | | | %I > 35% @ 40 uM |
| 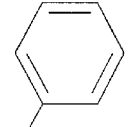 |  | 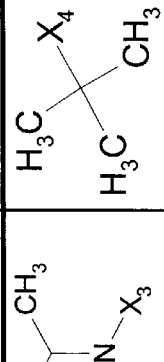 | 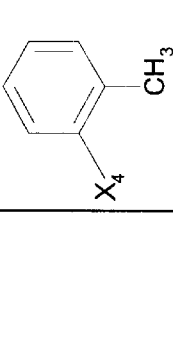 | | | | | %I > 35% @ 40 uM |
| 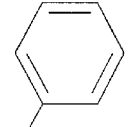 |  | 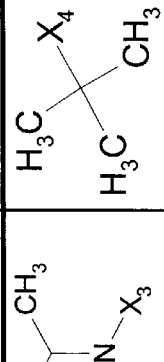 | 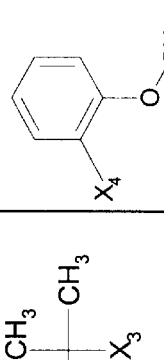 | | | | | %I > 35% @ 40 uM |
| 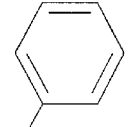 |  | 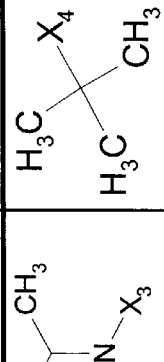 | 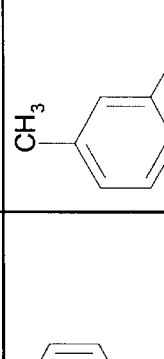 | | | | | %I > 35% @ 40 uM |
Figure 3A-26

| $R_1$ | $R_2$ | $R_3$ | $R_4$ | $R_5$ | $R_6$ | $R_7$ | $R_8$ | Activity |
|---|---|---|---|---|---|---|---|---|
| 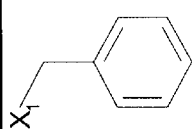 | 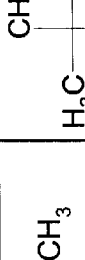 | 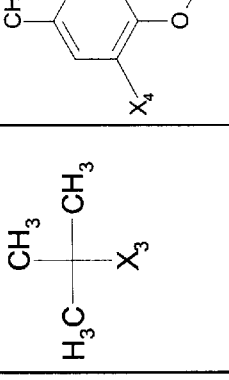 | 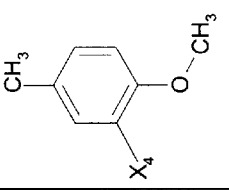 | | | | | %I > 35% @ 40 uM |
| 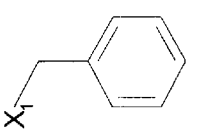 | 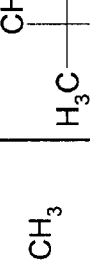 | 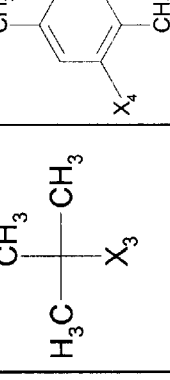 | 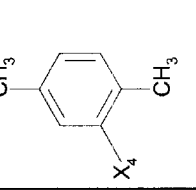 | | | | | %I > 35% @ 40 uM |
| 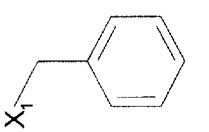 |  | 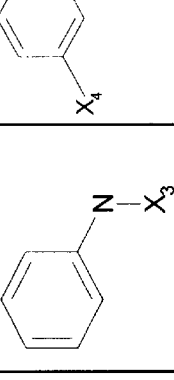 | 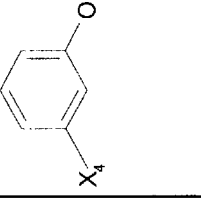 | | | | | %I > 35% @ 40 uM |
| 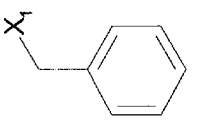 | 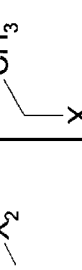 | 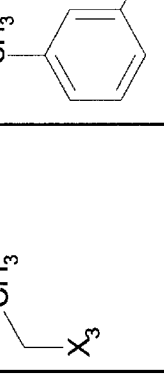 | 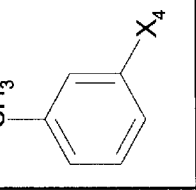 | | | | | %I > 35% @ 40 uM |
Figure 3A-27

| R₁ | R₂ | R₃ | R₄ | R₅ | R₆ | R₇ | R₈ | Activity |
|---|---|---|---|---|---|---|---|---|
| X₁-CH₂-C₆H₅ | X₂-CH₃ | H₃C-(CH₂)₃-X₃ | 3-hydroxyphenyl-X₄ | | | | | %I > 35% @ 40 uM |
| X₁-CH₂-C₆H₅ | H₃C-X₂ | (CH₃)₂CH-N(CH₃)-X₃ | 2-methylphenyl-X₄ | | | | | %I > 35% @ 40 uM |

Figure 3A-28

| R1 | R2 | R3 | R4 | R5 | R6 | R7 | R8 | Activity |
|---|---|---|---|---|---|---|---|---|
| ![benzyl] | H3C-X2 | X3-C6H4-CH3 (para) | X4-CH2CH2CH2-NH-CH(CH3)2 | | | X7-Cl | | IC50 < 100 nM |
| 4-Cl-C6H4-X1 | H3C-X2 | X3-C6H4-Br (para) | X4-CH2CH2-N(CH3)2 | | | X7-Cl | | IC50 < 100 nM |
| ![benzyl] | H3C-X2 | X3-C6H4-CH3 (para) | X4-CH2CH2CH2-N(CH3)2 | | | X7-Cl | | IC50 < 100 nM |

Figure 3A-29

| R₁ | R₂ | R₃ | R₄ | R₅ | R₆ | R₇ | R₈ | Activity |
|---|---|---|---|---|---|---|---|---|
| benzyl-X₁ | X₂-CH₃ | X₃-C₆H₄-CH₃ | X₄-(CH₂)₃-NH₂ | | | X₇-Cl | | IC50 < 100 nM |
| 3-methoxybenzyl-X₁ | H₃C-X₂ | X₃-C₆H₄-CH₃ | X₄-(CH₂)₃-NH₂ | | | X₇-Cl | | IC50 < 100 nM |
| benzyl-X₁ | X₂-CH₃ | X₃-C₆H₄-Br | X₄-(CH₂)₃-NH₂ | | | X₇-Cl | | IC50 < 100 nM |
| benzyl-X₁ | (CH₃)₂CH-X₂ | X₃-C₆H₄-CH₃ | X₄-(CH₂)₃-NH₂ | | | X₇-Cl | | IC50 < 100 nM |
| benzyl-X₁ | X₂-CH₃ | X₃-C₆H₄-CH₃ | X₄-CH₂-azetidinyl | | | X₇-Cl | | IC50 < 100 nM |

Figure 3A-30

| R₁ | R₂ | R₃ | R₄ | R₅ | R₆ | R₇ | R₈ | Activity |
|---|---|---|---|---|---|---|---|---|
| benzyl-X₁ | X₂-CH₂-CH₃ | X₃-C₆H₄-Br | X₄-CH₂CH₂-NH-CH₃ | | | X₇-Cl | | IC50 < 100 nM |
| benzyl-X₁ | X₂-CH₃ | X₃-C₆H₄-CH₃ | X₄-CH₂-(azetidinyl) | | | X₇-Cl | | IC50 < 100 nM |
| benzyl-X₁ | X₂-CH₂-CH₃ | X₃-C₆H₄-Br | X₄-CH₂CH₂CH₂-NH₂ | | | X₇-Cl | | IC50 < 100 nM |
| benzyl-X₁ | X₂-CH₂-S-CH₃ | X₃-C₆H₄-CH₃ | X₄-(CH₂)₄-NH₂ | | | X₇-Cl | | IC50 < 100 nM |
| benzyl-X₁ | X₂-CH₂-CH₃ | X₃-C₆H₄-CH₃ | X₄-CH₂-(3-piperidinyl) | | | X₇-Cl | | IC50 < 100 nM |

Figure 3A-32

| R₁ | R₂ | R₃ | R₄ | R₅ | R₆ | R₇ | R₈ | Activity |
|---|---|---|---|---|---|---|---|---|
| benzyl-X₁ | X₂-CH₃ | X₃-C₆H₄-CH₃ | X₄-(CH₂)-NH₂ | | | X₇-F | | IC50 < 100 nM |
| benzyl-X₁ | X₂-CH₃ | X₃-C₆H₄-Br | X₄-CH₂-N(CH₃)₂ | | | X₇-Cl | | IC50 < 100 nM |
| benzyl-X₁ | H₃C-X₂ | X₃-C₆H₄-Br | X₄-(CH₂)-NH₂ | | | | | IC50 < 100 nM |
| benzyl-X₁ | X₂-CH₃ | X₃-C₆H₄-CH₃ | X₄-(2-piperidyl) | | | X₇-Cl | | IC50 < 100 nM |
| benzyl-X₁ | H₃C-X₂ | X₃-C₆H₄-Br | X₄-(CH₂)-NH₂ | | | X₇-Cl | | IC50 < 100 nM |

Figure 3A-33

| R1 | R2 | R3 | R4 | R5 | R6 | R7 | R8 | Activity |
|---|---|---|---|---|---|---|---|---|
| 3-Cl-benzyl | ethyl | 4-Br-phenyl | -CH2CH2N(CH3)2 | | | Cl | | IC50 < 100 nM |
| benzyl | ethyl | 4-Br-phenyl | -CH2CH2N(CH3)2 | | | Cl | | IC50 < 100 nM |
| benzyl | methyl | 4-CH3-phenyl | -CH2CH2-piperidinyl | | | Cl | | IC50 < 100 nM |
| benzyl | methyl | 4-CH3-phenyl | -CH2CH2-imidazolyl | | | Cl | | IC50 < 100 nM |
| benzyl | methyl | 4-CH3-phenyl | -CH2-pyrrolidinyl | | | Cl | | IC50 < 100 nM |

| R₁ | R₂ | R₃ | R₄ | R₅ | R₆ | R₇ | R₈ | Activity |
|---|---|---|---|---|---|---|---|---|
| PhCH₂-X₁ | X₂-CH₂-CH₃ | X₃-C₆H₄-CH₃ | X₄-(CH₂)₂-N(azetidine) | | | Cl-X₇ | | IC50 < 100 nM |
| PhCH₂-X₁ | X₂-CH₂-CH₃ | X₃-C₆H₄-CH₃ | X₄-(CH₂)₂-N(pyrrolidine) | | | Cl-X₇ | | IC50 < 100 nM |
| PhCH₂-X₁ | X₂-CH₂-CH₃ | X₃-C₆H₄-CH₃ | X₄-(CH₂)₃-N(pyrrolidine) | | | Cl-X₇ | | IC50 < 100 nM |
| PhCH₂-X₁ | H₃C-X₂-CH₂-CH₂ | X₃-C₆H₄-Br | X₄-(CH₂)₃-N(CH₃)₂ | | | X₇-Cl | | IC50 < 100 nM |
| PhCH₂-X₁ | H₃C-X₂-CH₂-CH₂ | X₃-C₆H₄-Br | X₄-(CH₂)₂-N(CH₃)₂ | | | X₇-Cl | | IC50 < 100 nM |

Figure 3A-36

| R₁ | R₂ | R₃ | R₄ | R₅ | R₆ | R₇ | R₈ | Activity |
|---|---|---|---|---|---|---|---|---|
| benzyl | ethyl-X₂ | 4-Br-phenyl | ethyl-pyrrolidine | | | X₇-Cl | | IC50 < 100 nM |
| benzyl | ethyl-X₂ | 4-Br-phenyl | propyl-pyrrolidine | | | X₇-Cl | | IC50 < 100 nM |
| benzyl | propyl-CH₃ | 4-CH₃-phenyl | 4-piperidinylmethyl | | | X₇-Cl | | IC50 < 100 nM |
| benzyl | S-CH₃ propyl | 4-CH₃-phenyl | propyl-NH₂ | | | X₇-Cl | | IC50 < 100 nM |
| benzyl | propyl-CH₃ | 4-CH₃-phenyl | propyl-piperidine | | | X₇-Cl | | IC50 < 100 nM |

Figure 3A-37

| R₁ | R₂ | R₃ | R₄ | R₅ | R₆ | R₇ | R₈ | Activity |
|---|---|---|---|---|---|---|---|---|
| benzyl-X₁ | phenyl-X₂ | X₃-C₆H₄-CH₃ | X₄-(CH₂)₃-NH₂ | | | X₇-Cl | | IC50 < 100 nM |
| benzyl-X₁ | X₂-CH₂-CH₃ | X₃-C₆H₄-Br | X₄-CH₂-(N-methylpyrrolidinyl) | | | X₇-Cl | | IC50 < 100 nM |
| benzyl-X₁ | X₂-CH₂-CH₃ | X₃-C₆H₄-CH₃ | X₄-(3-piperidinyl) | | | X₇-Cl | | IC50 < 100 nM |
| benzyl-X₁ | X₂-CH₂-CH₃ | X₃-C₆H₄-CH₃ | X₄-(4-piperidinyl) | | | X₇-Cl | | IC50 < 100 nM |
| 4-Cl-benzyl-X₁ | H₃C-CH₂-X₂ | X₃-C₆H₄-Br | X₄-CH₂CH₂-N(CH₃)₂ | | | X₇-Cl | | IC50 < 100 nM |

Figure 3A-38

| $R_1$ | $R_2$ | $R_3$ | $R_4$ | $R_5$ | $R_6$ | $R_7$ | $R_8$ | Activity |
|---|---|---|---|---|---|---|---|---|
| benzyl-$X_1$ | $X_2$-CH$_2$CH$_2$-CH$_3$ | $X_3$-C$_6$H$_4$-Br | $X_4$-C(CH$_3$)$_3$-CH$_2$-N(CH$_3$)$_2$ | | | $X_7$-Cl | | IC50 < 100 nM |
| benzyl-$X_1$ | H$_3$C-CH$_2$CH$_2$-$X_2$ | $X_3$-C$_6$H$_4$-Br | $X_4$-(CH$_2$)$_4$-NH$_2$ | | | $X_7$-Cl | | IC50 < 100 nM |
| benzyl-$X_1$ | H$_3$C-CH$_2$CH$_2$-$X_2$ | $X_3$-C$_6$H$_4$-CH$_3$ | $X_4$-(CH$_2$)$_3$-N(CH$_3$)$_2$ | | | $X_7$-F | | IC50 < 100 nM |
| benzyl-$X_1$ | $X_2$-CH$_2$CH$_2$-CH$_3$ | $X_3$-C$_6$H$_4$-Br | $X_4$-(CH$_2$)$_2$-N(piperidinyl-CH$_3$) | | | $X_7$-Cl | | IC50 < 100 nM |
| benzyl-$X_1$ | H$_3$C-CH$_2$CH$_2$-$X_2$ | $X_3$-C$_6$H$_4$-CH$_3$ | $X_4$-(CH$_2$)$_2$-N(CH$_3$)$_2$ | | | $X_7$-F | | IC50 < 100 nM |

| R₁ | R₂ | R₃ | R₄ | R₅ | R₆ | R₇ | R₈ | Activity |
|---|---|---|---|---|---|---|---|---|
| benzyl-X₁ | H₃C-X₂ | X₃-C₆H₄-Br (para) | X₄-O-CH₂CH₂-NH₂ | | | X₇-Cl | | IC50 < 100 nM |
| benzyl-X₁ | H₃C-X₂ | X₃-naphthyl | X₄-N(CH₃)₂ | | | X₇-Cl | | IC50 < 100 nM |
| benzyl-X₁ | cyclohexyl-CH₂-X₂ | X₃-C₆H₄-CH₃ (para) | X₄-CH₂CH₂-NH₂ | | | Cl-X₇ | | IC50 < 100 nM |
| benzyl-X₁ | H₃C-X₂ | X₃-C₆H₄-Br (para) | X₄-N(piperidine) | | | X₇-Cl | | IC50 < 100 nM |
| benzyl-X₁ | CH₃-X₂ | X₃-C₆H₄-CH₃ (para) | X₄-CH₂CH₂-OH | | | Cl-X₇ | | IC50 < 100 nM |

| $R_1$ | $R_2$ | $R_3$ | $R_4$ | $R_5$ | $R_6$ | $R_7$ | $R_8$ | Activity |
|---|---|---|---|---|---|---|---|---|
| benzyl-X₁ | H₃C-X₂ | X₃-C₆H₄-CH₃ | X₄-CH₂CH₂-N(CH₃)₂ | | | | X₈-Cl | IC50 < 100 nM |
| benzyl-X₁ | H₃C-X₂ | X₃-C₆H₄-Br | X₄-CH₂CH₂-N(CH₃)(H₃C) | Cl-X₅ | | | | IC50 < 100 nM |
| benzyl-X₁ | X₂-(CH₂)₃-NH₂ | X₃-C₆H₄-CH₃ | X₄-(CH₂)₃-NH₂ | | | Cl-X₇ | | IC50 < 100 nM |
| benzyl-X₁ | H₃C-X₂ | X₃-C₆H₄-CH₃ | X₄-CH₂CH₂-N(CH₃)₂ | | X₆-F | X₇-F | | IC50 < 100 nM |
| 3-CH₃-benzyl-X₁ | H₃C-X₂ | X₃-C₆H₄-Br | X₄-CH₂CH₂-N(CH₃)₂ | | | X₇-Cl | | IC50 < 100 nM |

Figure 3A-43

| R₁ | R₂ | R₃ | R₄ | R₅ | R₆ | R₇ | R₈ | Activity |
|---|---|---|---|---|---|---|---|---|
| Ph-CH₂-X₁ | H₃C-CH₂-X₂ | X₃-C₆H₄-Br | X₄-CH₂CH₂-N(CH₃)₂ | | X₆-F | X₇-F | | IC50 < 100 nM |
| Ph-CH₂-X₁ | X₂-CH₂-CH₃ | X₃-C₆H₄-Br | X₄-CH₂CH₂-COOH | | | X₇-Cl | | IC50 < 100 nM |
| Ph-CH₂-X₁ | X₂-CH₂-CH₃ | X₃-(benzodioxole) | X₄-CH₂CH₂-N(CH₃)H | | | X₇-Cl | | IC50 = 100 nM-1 uM |
| Ph-CH₂-X₁ | H₃C-CH₂-X₂ | X₃-C₆H₄-Br | X₄-CH₂CH₂-(imidazole) | | | X₇-Cl | | IC50 = 100 nM-1 uM |
| Ph-CH₂-X₁ | X₂-CH₂-CH₃ | X₃-C₆H₄-CH₃ | X₄-CH₂CH₂-N(CH₃)H | | | X₇-Cl | | IC50 = 100 nM-1 uM |

Figure 3A-44

| R₁ | R₂ | R₃ | R₄ | R₅ | R₆ | R₇ | R₈ | Activity |
|---|---|---|---|---|---|---|---|---|
| benzyl-X₁ | X₂-CH₂CH₂-CH₃ | X₃-naphthyl | H₃C-N(CH₃)-CH₂CH₂-X₄ | | | X₇-Cl | | IC50 = 100 nM-1 uM |
| benzyl-X₁ | X₂-CH₂CH₂-CH₃ | X₃-(3-bromophenyl) | H₃C-N(CH₃)-CH₂CH₂-X₄ | | | X₇-Cl | | IC50 = 100 nM-1 uM |
| benzyl-X₁ | X₂-CH₂CH₂-CH₃ | X₃-(2-quinolinyl) | H₃C-N(CH₃)-CH₂CH₂-X₄ | | | X₇-Cl | | IC50 = 100 nM-1 uM |
| benzyl-X₁ | H₃C-CH₂CH₂-X₂ | X₃-(4-bromophenyl) | pyrrolidinone-X₄ | | | X₇-Cl | | IC50 = 100 nM-1 uM |
| CH₃-CH₂-X₁ | H₃C-CH₂CH₂-X₂ | X₃-(3,4-dichlorophenyl) | H₃C-N(CH₃)-CH₂CH₂-X₄ | | | X₇-Cl | | IC50 = 100 nM-1 uM |

Figure 3A-45

| R₁ | R₂ | R₃ | R₄ | R₅ | R₆ | R₇ | R₈ | Activity |
|---|---|---|---|---|---|---|---|---|
| benzyl-X₁ | H₃C-X₂ | 3,4-dichlorophenyl-X₃ | X₄-CH₂CH₂-N(CH₃)₂ | | | | | IC50 = 100 nM-1 uM |
| benzyl-X₁ | X₂-CH₂CH₃ | 4-methoxyphenyl-X₃ | X₄-CH₂CH₂-N(CH₃)₂ | | | Cl-X₇ | | IC50 = 100 nM-1 uM |
| benzyl-X₁ | H₃C-X₂ | 4-bromophenyl-X₃ | X₄-CH₂CH₂-N(CH₃)₂ | | | X₇-CH₃ | | IC50 = 100 nM-1 uM |
| benzyl-X₁ | X₂-CH₂CH₃ | 4-methylphenyl-X₃ | X₄-CH₂CH₂-piperazinyl | | | Cl-X₇ | | IC50 = 100 nM-1 uM |
| benzyl-X₁ | X₂-CH₂CH₃ | 3-fluorophenyl-X₃ | X₄-CH₂CH₂-N(CH₃)₂ | | | Cl-X₇ | | IC50 = 100 nM-1 uM |

Figure 3A-46

| R₁ | R₂ | R₃ | R₄ | R₅ | R₆ | R₇ | R₈ | Activity |
|---|---|---|---|---|---|---|---|---|
| phenyl-X₁ | X₂-CH₃ | X₃-C₆H₄-CF₃ | (H₃C)₂N-X₄ | | | X₇-Cl | | IC50 = 100 nM-1 uM |
| phenyl-X₁ | H₃C-X₂ | X₃-C₆H₄-CH₃ | (CH₃)(H₃C)N-X₄ | Cl-X₅ | | | | IC50 = 100 nM-1 uM |
| phenyl-X₁ | H₃C-X₂ | X₃-C₆H₄-Br | (CH₃)(H₃C)N-X₄ | | | X₇-F | | IC50 = 100 nM-1 uM |
| phenyl-X₁ | BnO-X₂ | X₃-C₆H₄-CH₃ | X₄-NH₂ | | | X₇-Cl | | IC50 = 100 nM-1 uM |
| phenyl-X₁ | X₂-S⁺(O⁻)-CH₃ | X₃-C₆H₄-CH₃ | X₄-NH₂ | | | X₇-Cl | | IC50 = 100 nM-1 uM |

Figure 3A-47

| R₁ | R₂ | R₃ | R₄ | R₅ | R₆ | R₇ | R₈ | Activity |
|---|---|---|---|---|---|---|---|---|
| benzyl-X₁ | H₃C-X₂ | 4-Br-phenyl-X₃ | X₄-CH₂CH₂-morpholine | | | X₇-Cl | | IC50 = 100 nM-1 uM |
| benzyl-X₁ | H₃C-X₂ | 4-CF₃-phenyl-X₃ | X₄-CH₂CH₂-N(CH₃)₂ | | | X₇-F | | IC50 = 100 nM-1 uM |
| benzyl-X₁ | H₃C-X₂ | 3-OCH₃-phenyl-X₃ | X₄-CH₂CH₂-N(CH₃)₂ | | | X₇-Cl | | IC50 = 100 nM-1 uM |
| benzyl-X₁ | H₃C-X₂ | 3,4-diCl-phenyl-X₃ | X₄-CH₂CH₂-N(CH₃)₂ | | | X₇-Cl | | IC50 = 100 nM-1 uM |
| benzyl-X₁ | X₂-CH₃ | 2-indolyl-X₃ | H₃C-N(CH₃)-CH₂CH₂-X₄ | | | Cl-X₇ | | IC50 = 100 nM-1 uM |

Figure 3A-48

| R₁ | R₂ | R₃ | R₄ | R₅ | R₆ | R₇ | R₈ | Activity |
|---|---|---|---|---|---|---|---|---|
| benzyl-X₁ | H₃C-X₂ | X₃-C₆H₄-CF₃ | X₄-CH₂CH₂-N(CH₃)₂ | | Cl-X₆ | | | IC50 = 100 nM-1 uM |
| benzyl-X₁ | H₃C-X₂ | X₃-C₆H₄-CF₃ | X₄-CH₂CH₂-N(CH₃)₂ | Cl-X₅ | | | | IC50 = 100 nM-1 uM |
| benzyl-X₁ | X₂-CH₃ | X₃-C₆H₄-Br | X₄-CH₂CH₂C(O)OCH₃ | | | Cl-X₇ | | IC50 = 100 nM-1 uM |
| CH₃O-C₆H₄-CH₂-X₁ | X₂-CH₃ | X₃-C₆H₄-CH₃ | X₄-CH₂CH₂CH₂-NH₂ | | | Cl-X₇ | | IC50 = 100 nM-1 uM |
| benzyl-X₁ | X₂-CH₂-S⁺(CH₃)-O⁻ | X₃-C₆H₄-CH₃ | X₄-CH₂CH₂CH₂-NH₂ | | | Cl-X₇ | | IC50 = 100 nM-1 uM |

Figure 3A-49

| R₁ | R₂ | R₃ | R₄ | R₅ | R₆ | R₇ | R₈ | Activity |
|---|---|---|---|---|---|---|---|---|
| benzyl-X₁ | | X₃-C₆H₄-CH₃ (para) | X₄-CH₂CH₂-pyrrolidinyl | | | Cl-X₇ | | IC50 = 100 nM-1 uM |
| benzyl-X₁ | H₃C-X₂ | X₃-C₆H₄-CF₃ (para) | X₄-CH₂CH₂CH₂-N(CH₃)₂ | | | X₇-F | | IC50 = 100 nM-1 uM |
| benzyl-X₁ | HO-X₂ | X₃-C₆H₄-CH₃ (para) | X₄-CH₂CH₂CH₂-NH₂ | | | Cl-X₇ | | IC50 = 100 nM-1 uM |
| benzyl-X₁ | X₂-CH₃ | X₃-C₆H₄-Br (para) | X₄-CH(CH₃)- | | | Cl-X₇ | | IC50 = 100 nM-1 uM |
| benzyl-X₁ | X₂-CH₃ | X₃-C₆H₄-CF₃ (meta) | X₄-CH₂CH₂-N(CH₃)(CH₃) | | | Cl-X₇ | | IC50 = 100 nM-1 uM |

Figure 3A-50

| R₁ | R₂ | R₃ | R₄ | R₅ | R₆ | R₇ | R₈ | Activity |
|---|---|---|---|---|---|---|---|---|
|  | |  |  | | |  | | IC50 = 100 nM-1 uM |
|  |  |  |  | | |  | | IC50 = 100 nM-1 uM |
|  | |  |  | | |  | | IC50 = 100 nM-1 uM |
|  |  |  |  | | | |  | IC50 = 100 nM-1 uM |
|  |  |  |  | | | | | IC50 = 100 nM-1 uM |
Figure 3A-51

| R₁ | R₂ | R₃ | R₄ | R₅ | R₆ | R₇ | R₈ | Activity |
|---|---|---|---|---|---|---|---|---|
| benzyl-X₁ | X₂-CH₂CH₃ | X₃-C₆H₄-F | X₄-CH₂CH₂-NH₂ | | | | | IC50 = 100 nM-1 uM |
| benzyl-X₁ | X₂-CH₂CH₃ | X₃-C₆H₄-CH₃ | X₄-CH₂CH₂-OH | | | Cl-X₇ | | IC50 = 100 nM-1 uM |
| benzyl-X₁ | H₃C-X₂ | X₃-C₆H₄-F | X₄-CH₂CH₂-N(CH₃)₂ | | | X₇-F | | IC50 = 100 nM-1 uM |
| benzyl-X₁ | | X₃-C₆H₄-Br | X₄-CH₂CH₂-NH₂ | | | X₇-Cl | | IC50 = 100 nM-1 uM |
| benzyl-X₁ | X₂-CH₂CH₃ | X₃-naphthyl | X₄-CH₂-N(CH₃)-CH₂-H₃C | | | | | IC50 = 100 nM-1 uM |

Figure 3A-53

| R₁ | R₂ | R₃ | R₄ | R₅ | R₆ | R₇ | R₈ | Activity |
|---|---|---|---|---|---|---|---|---|
| benzyl-X₁ | X₂-CH₂CH₃ | X₃-C₆H₄-CF₃ | X₄-(CH₂)₃-NH₂ | | | X₇-F | | IC50 = 100 nM-1 uM |
| benzyl-X₁ | X₂-CH₂CH₃ | X₃-C₆H₄-Br | X₄-CH₂CH(CH₃)N(CH(CH₃)₂)CH(CH₃)CH₃ | | | X₇-Cl | | IC50 = 100 nM-1 uM |
| benzyl-X₁ | | X₃-C₆H₄-CH₃ | X₄-(CH₂)₃-NH₂ | | | X₇-Cl | | IC50 = 100 nM-1 uM |
| benzyl-X₁ | H₃C-X₂ | X₃-C₆H₄-H | X₄-(CH₂)₄-N(CH₃)CH₃ | | | X₇-F | | IC50 = 100 nM-1 uM |
| benzyl-X₁ | H₃C-X₂ | X₃-C₆H₄-F | X₄-(CH₂)₄-N(CH₃)CH₃ | | | X₇-F | | IC50 = 100 nM-1 uM |

Figure 3A-54

| $R_1$ | $R_2$ | $R_3$ | $R_4$ | $R_5$ | $R_6$ | $R_7$ | $R_8$ | Activity |
|---|---|---|---|---|---|---|---|---|
| benzyl-$X_1$ | $X_2$-CH$_2$CH$_2$-CH$_3$ | $X_3$-C$_6$H$_4$-Br | $X_4$-CH(CH$_3$)-propyl-N(CH$_3$)(CH$_3$) | | | Cl-$X_7$ | | IC50 = 100 nM-1 uM |
| benzyl-$X_1$ | H$_3$C-CH$_2$-$X_2$ | $X_3$-C$_6$H$_4$-F | $X_4$-CH$_2$CH$_2$-N(CH$_3$)(CH$_3$) | | | $X_7$-CH$_3$ | | IC50 = 100 nM-1 uM |
| benzyl-$X_1$ | H$_3$C-CH$_2$-$X_2$ | $X_3$-C$_6$H$_4$-F | $X_4$-CH$_2$CH$_2$-N(CH$_3$)(CH$_3$) | Cl-$X_5$ | | | | IC50 = 100 nM-1 uM |
| benzyl-$X_1$ | $X_2$-CH$_2$CH$_2$-CH$_3$ | $X_3$-quinoline | H$_3$C-CH$_2$CH$_2$-N(CH$_3$)($X_4$) | | | Cl-$X_7$ | | IC50 = 100 nM-1 uM |
| benzyl-$X_1$ | H$_3$C-CH$_2$-$X_2$ | $X_3$-C$_6$H$_3$(Cl)(Cl) | $X_4$-CH$_2$CH$_2$-N(CH$_3$)(CH$_3$) | | | | | IC50 = 100 nM-1 uM |

| R₁ | R₂ | R₃ | R₄ | R₅ | R₆ | R₇ | R₈ | Activity |
|---|---|---|---|---|---|---|---|---|
| CH₃—X₁ | H₃C—X₂ | X₃—C₆H₄—Br | X₄—CH₂CH₂—N(CH₃)₂ | | | X₇—Cl | | IC50 = 1 uM-10 uM |
| C₆H₅—CH₂—X₁ | H₃C—X₂ | X₃—C₆H₄—Br | X₄—CH₂CH₂—O—CH₃ | | | X₇—Cl | | IC50 = 1 uM-10 uM |
| C₆H₅—CH₂—X₁ | X₂—CH₃ | X₃—C₆H₄—S(O)₂—CH₃ | H₃C—N(CH₃)—CH₂CH₂—X₄ | | | Cl—X₇ | | IC50 = 1 uM-10 uM |
| C₆H₅—CH₂—X₁ | X₂—CH₃ | X₃—C₆H₄—C₆H₅ | H₃C—N(CH₃)—CH₂CH₂—X₄ | | | Cl—X₇ | | IC50 = 1 uM-10 uM |

Figure 3A-58

| R₁ | R₂ | R₃ | R₄ | R₅ | R₆ | R₇ | R₈ | Activity |
|---|---|---|---|---|---|---|---|---|
| CH₃-O-C₆H₄-X₁ | H₃C-X₂ | X₃-C₆H₄-(CH₂)₃-CH₃ | X₄-CH₂CH₂-N(CH₃)₂ | | | X₇-Cl | | IC50 = 1 uM-10 uM |
| C₆H₅-CH₂-X₁ | H₃C-X₂ | X₃-N-C₆H₄-Br | X₄-CH₂CH₂-N(CH₃)₂ | | | | | IC50 = 1 uM-10 uM |
| Br-C₆H₄-X₁ | H₃C-X₂ | X₃-C₆H₄-(CH₂)₃-CH₃ | X₄-CH₂CH₂-N(CH₃)₂ | | | | | IC50 = 1 uM-10 uM |
| Br-C₆H₄-X₁ | H₃C-X₂ | X₃-C₆H₄-F | X₄-CH₂CH₂-N(CH₃)₂ | | | | | IC50 = 1 uM-10 uM |

| R₁ | R₂ | R₃ | R₄ | R₅ | R₆ | R₇ | R₈ | Activity |
|---|---|---|---|---|---|---|---|---|
| benzyl-X₁ | H₃C-X₂ | X₃-C₆H₄-Br | X₄-CH₂CH₂-N(CH₃)₂ | | | | | IC50 = 1 uM-10 uM |
| benzyl-X₁ | H₃C-X₂ | X₃-C₆H₄-Br | X₄-CH₂-(3-pyridyl) | | | X₇-Cl | | IC50 = 1 uM-10 uM |
| naphthyl-X₁ | CH₃-X₂ | X₃-naphthyl | H₃C-N(CH₃)-CH₂CH₂-X₄ | | | | | IC50 = 1 uM-10 uM |
| 2-CH₃-C₆H₄-X₁ | CH₃-X₂ | X₃-naphthyl | H₃C-N(CH₃)-CH₂CH₂-X₄ | | | | | IC50 = 1 uM-10 uM |
| benzyl-X₁ | H₃C-X₂ | X₃-C₆H₄-Br | X₄-CH₂CH₂-morpholinyl | | | | | IC50 = 1 uM-10 uM |

| R₁ | R₂ | R₃ | R₄ | R₅ | R₆ | R₇ | R₈ | Activity |
|---|---|---|---|---|---|---|---|---|
| phenyl-X₁ | H₃C-X₂ | X₃-phenyl-CN | X₄-(CH₂)-N(CH₃)CH₃ | | | X₇-F | | IC50 = 1 uM-10 uM |
| phenyl-X₁ | H₃C-X₂ | X₃-phenyl-Br | X₄-(CH₂)-NH₂ | | | | | IC50 = 1 uM-10 uM |
| phenyl-X₁ | H₃C-X₂ | X₃-phenyl-CH₃ | X₄-CH₂-N(CH₃)CH₃ | | | | | IC50 = 1 uM-10 uM |
| phenyl-X₁ | H₃C-X₂ | X₃-benzodioxole | X₄-CH₂-N(CH₃)CH₃ | | | | | IC50 = 1 uM-10 uM |
| phenyl-X₁ | H₃C-X₂ | X₃-phenyl-F | X₄-CH₂-N(CH₃)CH₃ | | | | | IC50 = 1 uM-10 uM |

Figure 3A-64

| R1 | R2 | R3 | R4 | R5 | R6 | R7 | R8 | Activity |
|---|---|---|---|---|---|---|---|---|
| benzyl-X1 | H3C-X2 | X3-C6H4-CN (4-) | X4-CH2CH2-N(CH3)2 | | | X7-F | | IC50 = 1 uM-10 uM |
| benzyl-X1 | H3C-X2 | X3-C6H4-Br (4-) | X4-CH2CH2-N(CH3)2 | | | | | IC50 = 1 uM-10 uM |
| benzyl-X1 | indol-3-yl-CH2-X2 | X3-C6H4-CH3 (4-) | X4-CH2CH2-NH2 | | | X7-Cl | | IC50 = 1 uM-10 uM |
| benzyl-X1 | H3C-X2 | X3-C6H4-OCH3 (3-) | X4-CH2CH2-N(CH3)2 | | | | | IC50 = 1 uM-10 uM |
| benzyl-X1 | H3C-X2 | X3-C6H5 | X4-CH2CH2-N(CH3)2 | | | | X8-Cl | IC50 = 1 uM-10 uM |

Figure 3A-65

| R₁ | R₂ | R₃ | R₄ | R₅ | R₆ | R₇ | R₈ | Activity |
|---|---|---|---|---|---|---|---|---|
| 2-methylbenzyl-X₁ | H₃C-X₂ | X₃-C₆H₄-Br | X₄-N(CH₃)₂ | | | X₇-Cl | | IC50 = 1 uM-10 uM |
| benzyl-X₁ | | X₃-C₆H₄-Br | X₄-N(CH₃)₂ | | | | | IC50 = 1 uM-10 uM |
| benzyl-X₁ | H₃C-X₂ | X₃-C₆H₄-CH₃ | X₄-NH₂ | | | X₇-Cl | | IC50 = 1 uM-10 uM |
| tetrahydrofurfuryl-X₁ | H₃C-X₂ | X₃-C₆H₄-CH₃ | X₄-NH₂ | | | X₇-Cl | | IC50 = 1 uM-10 uM |
| benzyl-X₁ | CH₃-X₂ | X₃-C₆H₄-Br | X₄-morpholine | | | Cl-X₇ | | IC50 = 1 uM-10 uM |

| R1 | R2 | R3 | R4 | R5 | R6 | R7 | R8 | Activity |
|---|---|---|---|---|---|---|---|---|
| benzyl-X1 | H3C-X2 | X3-C6H4-Cl | X4-CH2CH2-N(CH3)2 | | | | | IC50 = 10 uM-50 uM |
| benzyl-X1 | H3C-X2 | X3-C6H4-Br | X4-CH2-indole | | | X7-Cl | | IC50 = 10 uM-50 uM |
| CH3-O-CH2CH2-X1 | X2-CH2CH3 | X3-naphthyl | X4-CH2CH2-N(CH3)2 | | | | | IC50 = 10 uM-50 uM |
| CH3-CH2-X1 | H3C-X2 | X3-C6H4-Cl | X4-CH2CH2-N(CH3)2 | | | X7-Cl | | IC50 = 10 uM-50 uM |
| 4-Cl-C6H4-X1 | X2-CH2CH3 | X3-naphthyl | X4-CH2CH2-N(CH3)2 | | | | | IC50 = 10 uM-50 uM |

Figure 3A-68

| R₁ | R₂ | R₃ | R₄ | R₅ | R₆ | R₇ | R₈ | Activity |
|---|---|---|---|---|---|---|---|---|
| benzyl-X₁ | H₃C-X₂ ethyl | X₃-phenyl | X₄-CH₂CH₂-N(CH₃)₂ | | | | | IC50 = 10 uM-50 uM |
| benzyl-X₁ | X₂-CH₃ methyl | X₃-naphthyl | X₄-CH₂CH₂-N(CH₃)₂ | | | | | IC50 = 10 uM-50 uM |
| CH₃-X₁ | H₃C-X₂ | X₃-(4-Cl-phenyl) | X₄-CH₂CH₂-N(CH₃)₂ | | | X₇-Cl | | IC50 = 10 uM-50 uM |
| CH₃-X₁ | X₂-CH₂CH₃ | X₃-naphthyl | X₄-CH₂CH₂-N(CH₃)₂ | | | X₇-Cl | | IC50 = 10 uM-50 uM |
| (3-Cl,4-F-phenyl)-X₁ | X₂-CH₂CH₃ | X₃-naphthyl | X₄-CH₂CH₂-N(CH₃)₂ | | | | | IC50 = 10 uM-50 uM |

Figure 3A-69

| R₁ | R₂ | R₃ | R₄ | R₅ | R₆ | R₇ | R₈ | Activity |
|---|---|---|---|---|---|---|---|---|
| naphthyl-X₁ | H₃C—X₂ | X₃-C₆H₄-Cl (para) | X₄-CH₂CH₂-N(CH₃)₂ | | | | | IC50 = 10 uM-50 uM |
| CH₃-O-CH₂CH₂-X₁ | H₃C—X₂ | X₃-C₆H₄-Br (para) | X₄-CH₂CH₂-N(CH₃)₂ | | | | | IC50 = 10 uM-50 uM |
| H₃C-C₆H₄-X₁ (para) | H₃C—X₂ | X₃-C₆H₄-Cl (para) | X₄-CH₃ | | | X₇-Cl | | IC50 = 10 uM-50 uM |
| benzyl-X₁ | H₃C—X₂ | X₃-C₆H₃(OCH₃)₂ (3,5) | X₄-CH₂CH₂-N(CH₃)₂ | | | | | IC50 = 10 uM-50 uM |
| H₃C-C₆H₄-X₁ (para) | H₃C—X₂ | X₃-C₆H₄-Br (para) | X₄-CH₃ | | | X₇-Cl | | IC50 = 10 uM-50 uM |

| R₁ | R₂ | R₃ | R₄ | R₅ | R₆ | R₇ | R₈ | Activity |
|---|---|---|---|---|---|---|---|---|
| 4-methylphenyl-X₁ | X₂-CH₃ | X₃-(2-naphthyl) | X₄-CH₂-O-CH₃ | | | Cl-X₇ | | IC50 = 10 uM-50 uM |
| 4-methylphenyl-X₁ | X₂-CH₂-CH₃ | X₃-(2-naphthyl) | X₄-CH₂-N(CH₃)₂ | | | | | IC50 = 10 uM-50 uM |
| benzyl-X₁ | H₃C-X₂ | X₃-(4-methylphenyl) | X₄-CH₂-CH₂-N(CH₃)₂ | | | | | IC50 = 10 uM-50 uM |
| benzyl-X₁ | H₃C-CH₂-X₂ | X₃-O-phenyl | X₄-CH₂-CH₂-N(CH₃)₂ | | | | | IC50 = 10 uM-50 uM |
| CH₃-O-CH₂-CH₂-X₁ | X₂-CH₂-CH₃ | X₃-(1-naphthyl) | X₄-CH₂-CH₂-N(CH₃)₂ | | | | | IC50 = 10 uM-50 uM |

Figure 3A-72

| R₁ | R₂ | R₃ | R₄ | R₅ | R₆ | R₇ | R₈ | Activity |
|---|---|---|---|---|---|---|---|---|
| benzyl-X₁ | H₃C-CH₂-X₂ | X₃-C₆H₄-F | X₄-CH₂-tetrahydrofuran | | | X₇-Cl | | IC50 = 10 uM-50 uM |
| benzyl-X₁ | X₂-CH₂-CH₃ | X₃-C₆H₄-CH₃ | X₄-CH₂CH₂-COOH | | | X₇-Cl | | IC50 = 10 uM-50 uM |
| benzyl-X₁ | X₂-CH₂-CH₃ | X₃-C₆H₄-CH₃ | X₄-CH₂-COOH | | | X₇-Cl | | IC50 = 10 uM-50 uM |
| benzyl-X₁ | X₂-CH₂-CH₃ | X₃-CH₂CH₂-N(CH₃)₂ | X₄-CH₂-C₆H₅ | | | X₇-Cl | | IC50 = 10 uM-50 uM |
| benzyl-X₁ | X₂-CH₂-CH₃ | X₃-C₆H₄-COOH | X₄-CH₂CH₂-N(CH₃)-CH₃ | | | X₇-Cl | | IC50 = 10 uM-50 uM |

Figure 3A-74

| R1 | R2 | R3 | R4 | R5 | R6 | R7 | R8 | Activity |
|---|---|---|---|---|---|---|---|---|
| Ph-CH2-X1 | | X3-O-C(CH3)(CH3)(CH3) | | | | | | IC50 = 10 uM-50 uM |

Figure 3A-75

| R1 | R2 | R3" | R4 | R5 | R6 | R7 | R8 | Activity |
|---|---|---|---|---|---|---|---|---|
| benzyl-X1 | X2-CH2-CH3 | X3-(3,5-difluorophenyl) | X4-CH2-CH2-NH2 | | | Cl-X7 | | Ki < 100 nM |
| benzyl-X1 | X2-CH2-CH3 | X3-(2-fluorophenyl) | X4-CH2-CH2-NH2 | | | Cl-X7 | | Ki < 100 nM |
| benzyl-X1 | X2-CH2-CH3 | X3-(3-fluorophenyl) | X4-CH2-CH2-NH2 | | | Cl-X7 | | Ki < 100 nM |

Figure 3A-76

| R₁ | R₂ | R₃" | R₄ | R₅ | R₆ | R₇ | R₈ | Activity |
|---|---|---|---|---|---|---|---|---|
| ⌬-X₁ | X₂-CH₃ | X₃-(2,4-diF-phenyl) | X₄-CH₂CH₂-NH₂ | | | Cl-X₇ | | Ki < 100 nM |
| ⌬-X₁ | X₂-CH₃ | X₃-(4-CH₃-phenyl) | X₄-CH₂CH₂-NH₂ | | | Cl-X₇ | | Ki < 100 nM |
| ⌬-X₁ | X₂-CH₃ | X₃-(3,5-diCH₃-phenyl) | X₄-CH₂CH₂-NH₂ | | | Cl-X₇ | | Ki < 100 nM |
| ⌬-X₁ | X₂-CH₃ | X₃-(4-Br-phenyl) | X₄-CH₂CH₂-NH₂ | | | Cl-X₇ | | Ki < 100 nM |
| ⌬-X₁ | X₂-CH₃ | X₃-(4-F-phenyl) | X₄-CH₂CH₂-NH₂ | | | Cl-X₇ | | Ki < 100 nM |

Figure 3A-77

| R1 | R2 | R3" | R4 | R5 | R6 | R7 | R8 | Activity |
|---|---|---|---|---|---|---|---|---|
| benzyl-X1 | X2-CH2CH3 | 3-methylphenyl-X3 | X4-CH2CH2NH2 | | | Cl-X7 | | Ki < 100 nM |
| benzyl-X1 | X2-CH2CH3 | 3,4-difluorophenyl-X3 | X4-CH2CH2NH2 | | | Cl-X7 | | Ki < 100 nM |
| benzyl-X1 | X2-CH2CH3 | 4-methylphenyl-X3 | X4-CH2-(pyrrolidin-2-yl) | | | Cl-X7 | | Ki < 100 nM |
| benzyl-X1 | X2-CH2CH3 | phenyl-X3 | X4-CH2CH2NH2 | | | Cl-X7 | | Ki < 100 nM |
| benzyl-X1 | X2-CH2CH3 | 2-methylphenyl-X3 | X4-CH2CH2NH2 | | | Cl-X7 | | Ki < 100 nM |

Figure 3A-78

| $R_1$ | $R_2$ | $R_3''$ | $R_4$ | $R_5$ | $R_6$ | $R_7$ | $R_8$ | Activity |
|---|---|---|---|---|---|---|---|---|
| benzyl-$X_1$ | $X_2$-CH2CH2-CH3 | $X_3$-C6H4-F | $X_4$-(CH2)3-NH2 | | | $X_7$-Cl | | Ki < 100 nM |
| benzyl-$X_1$ | $X_2$-CH2CH2-CH3 | $X_3$-C6H4-CH3 | $X_4$-(CH2)3-NH2 | | | $X_7$-Cl | | Ki < 100 nM |
| benzyl-$X_1$ | $X_2$-CH2CH2-CH3 | $X_3$-C6H4-CH3 | $X_4$-CH2-piperidine | | | $X_7$-Cl | | Ki < 100 nM |
| benzyl-$X_1$ | $X_2$-CH2CH2-CH3 | $X_3$-C6H4-Cl | $X_4$-(CH2)2-NH2 | | | $X_7$-Cl | | Ki < 100 nM |
| benzyl-$X_1$ | $X_2$-CH2CH2-CH3 | $X_3$-naphthyl | $X_4$-(CH2)2-NH2 | | | $X_7$-Cl | | Ki < 100 nM |

Figure 3A-79

| R₁ | R₂ | R₃" | R₄ | R₅ | R₆ | R₇ | R₈ | Activity |
|---|---|---|---|---|---|---|---|---|
| benzyl-X₁ | X₂-CH₂-CH₃ | X₃-(4-methylphenyl) | X₄-CH₂-(2-piperidinyl) | | | Cl-X₇ | | Ki < 100 nM |
| benzyl-X₁ | X₂-CH₂-CH₃ | X₃-(3-methoxyphenyl) | X₄-(CH₂)₃-NH₂ | | | Cl-X₇ | | Ki < 100 nM |
| benzyl-X₁ | X₂-CH₂-CH₃ | X₃-(4-methylphenyl) | X₄-CH₂-(3-piperidinyl) | | | Cl-X₇ | | Ki < 100 nM |
| benzyl-X₁ | X₂-CH₂-CH₃ | X₃-(2-methylphenyl) | X₄-(CH₂)₃-NH₂ | | | Cl-X₇ | | Ki < 100 nM |
| benzyl-X₁ | X₂-CH₂-CH₃ | X₃-(2,5-difluorophenyl) | X₄-(CH₂)₂-NH₂ | | | Cl-X₇ | | Ki < 100 nM |

Figure 3A-80

| $R_1$ | $R_2$ | $R_3$ | $R_4$ | $R_5$ | $R_6$ | $R_7$ | $R_8$ | Activity |
|---|---|---|---|---|---|---|---|---|
| benzyl-$X_1$ | $X_2$-CH2CH3 | 3,5-dimethylphenyl-$X_3$ | $X_4$-CH2CH2CH2NH2 | | | Cl-$X_7$ | | Ki < 100 nM |
| benzyl-$X_1$ | $X_2$-CH2CH3 | 2,3-difluorophenyl-$X_3$ | $X_4$-CH2CH2NH2 | | | Cl-$X_7$ | | Ki < 100 nM |
| benzyl-$X_1$ | $X_2$-CH2CH3 | 2,6-difluorophenyl-$X_3$ | $X_4$-CH2CH2NH2 | | | Cl-$X_7$ | | Ki < 100 nM |
| benzyl-$X_1$ | $X_2$-CH2CH3 | 3,5-dimethoxyphenyl-$X_3$ | $X_4$-CH2CH2NH2 | | | Cl-$X_7$ | | Ki < 100 nM |
| benzyl-$X_1$ | $X_2$-CH2CH3 | 3-chlorophenyl-$X_3$ | $X_4$-CH2CH2NH2 | | | Cl-$X_7$ | | Ki < 100 nM |

| R₁ | R₂ | R₃" | R₄ | R₅ | R₆ | R₇ | R₈ | Activity |
|---|---|---|---|---|---|---|---|---|
| 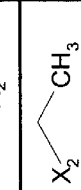 | 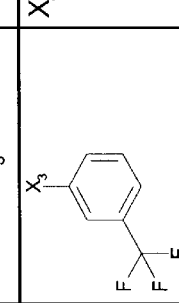 | 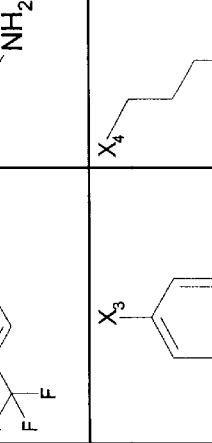 | 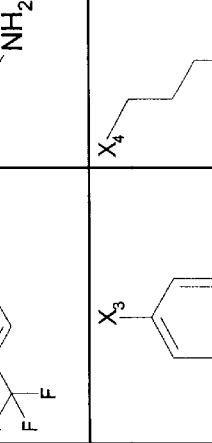 | | | 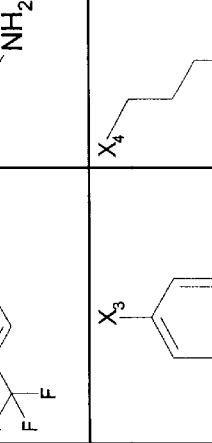 | | Ki < 100 nM |
| 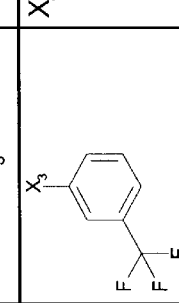 | 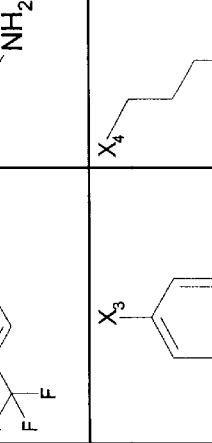 | 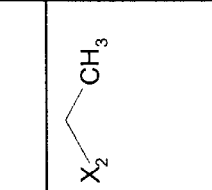 |  | | |  | | Ki < 100 nM |
| 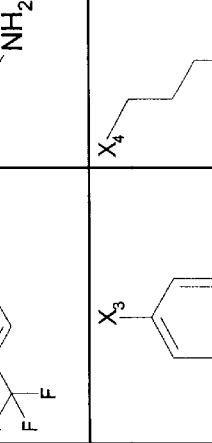 | 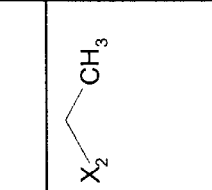 |  | 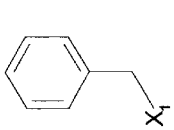 | | | 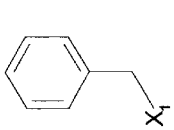 | | Ki < 100 nM |
| 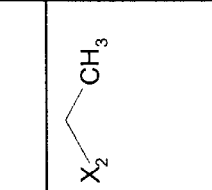 |  | 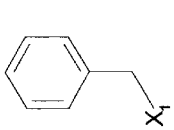 | 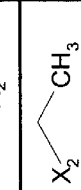 | | | 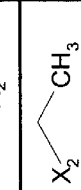 | | Ki < 100 nM |
|  | 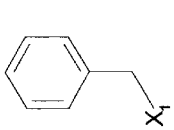 | 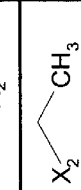 | 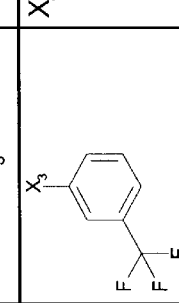 | | | 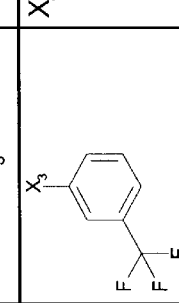 | | Ki < 100 nM |
Figure 3A-83

| $R_1$ | $R_2$ | $R_3''$ | $R_4$ | $R_5$ | $R_6$ | $R_7$ | $R_8$ | Activity |
|---|---|---|---|---|---|---|---|---|
| Benzyl-X₁ | X₂-CH₃ | Pentafluorophenyl-X₃ | X₄-CH₂CH₂-NH₂ | | | Cl-X₇ | | Ki < 100 nM |
| Benzyl-X₁ | X₂-CH₃ | 3,5-difluorophenyl-X₃ | X₄-CH₂CH₂-NH₂ | | | Cl-X₇ | | Ki < 100 nM |
| Benzyl-X₁ | X₂-CH₃ | 4-methylphenyl-X₃ | X₄-piperidine (N) | | | Cl-X₇ | | Ki < 100 nM |
| Benzyl-X₁ | X₂-CH₃ | 4-(methoxycarbonyl)phenyl-X₃ | X₄-CH₂CH₂-NH₂ | | | Cl-X₇ | | Ki < 100 nM |
| Benzyl-X₁ | X₂-CH₃ | 2-naphthyl-X₃ | X₄-CH₂CH₂-NH₂ | | | Cl-X₇ | | Ki < 100 nM |

Figure 3A-84

| R₁ | R₂ | R₃" | R₄ | R₅ | R₆ | R₇ | R₈ | Activity |
|---|---|---|---|---|---|---|---|---|
| ⟨benzyl-X₁⟩ | X₂-CH₂-CH₃ | X₃-C₆H₄-CN (para) | X₄-CH₂CH₂CH₂-NH₂ | | | Cl-X₇ | | Ki < 100 nM |
| ⟨benzyl-X₁⟩ | X₂-CH₂-CH₃ | X₃-C₆H₄-CN (ortho) | X₄-CH₂CH₂-NH₂ | | | Cl-X₇ | | Ki < 100 nM |
| ⟨benzyl-X₁⟩ | X₂-CH₂-CH₃ | X₃-C₆H₄-CF₃ (ortho) | X₄-CH₂CH₂-NH₂ | | | Cl-X₇ | | Ki < 100 nM |
| ⟨benzyl-X₁⟩ | X₂-CH₂-CH₃ | X₃-C₆H₄-OCF₃ (para) | X₄-CH₂CH₂-NH₂ | | | Cl-X₇ | | Ki = 100 nM-1 uM |
| ⟨benzyl-X₁⟩ | X₂-CH₂-CH₃ | X₃-C₆H₃-(CF₃)₂ (3,5) | X₄-CH₂CH₂-NH₂ | | | Cl-X₇ | | Ki = 100 nM-1 uM |

Figure 3A-85

| $R_1$ | $R_2$ | $R_3''$ | $R_4$ | $R_5$ | $R_6$ | $R_7$ | $R_8$ | Activity |
|---|---|---|---|---|---|---|---|---|
| $X_1$-CH2-phenyl | $X_2$-CH2CH2-CH3 | $X_3$-phenyl-O-CF3 | $X_4$-(CH2)3-NH2 | | | $X_7$-Cl | | Ki = 100 nM-1 uM |
| $X_1$-CH2-phenyl | $X_2$-CH2CH2-CH3 | $X_3$-phenyl-C(CH3)2-CH3 | $X_4$-(CH2)3-NH2 | | | $X_7$-Cl | | Ki = 100 nM-1 uM |
| $X_1$-CH2-phenyl | $X_2$-CH2CH2-CH3 | $X_3$-phenyl(OCH3)2 | $X_4$-(CH2)3-NH2 | | | $X_7$-Cl | | Ki = 100 nM-1 uM |
| $X_1$-CH2-phenyl | $X_2$-CH2CH2-CH3 | $X_3$-phenyl-C(=O)-O-CH3 | $X_4$-(CH2)3-NH2 | | | $X_7$-Cl | | Ki = 1 uM-10 uM |
| $X_1$-CH2-phenyl | $X_2$-CH2CH2-CH3 | $X_3$-phenyl-C(CH3)2-CH3 | $X_4$-(CH2)3-NH2 | | | $X_7$-Cl | | Ki = 1 uM-10 uM |

Figure 3A-86

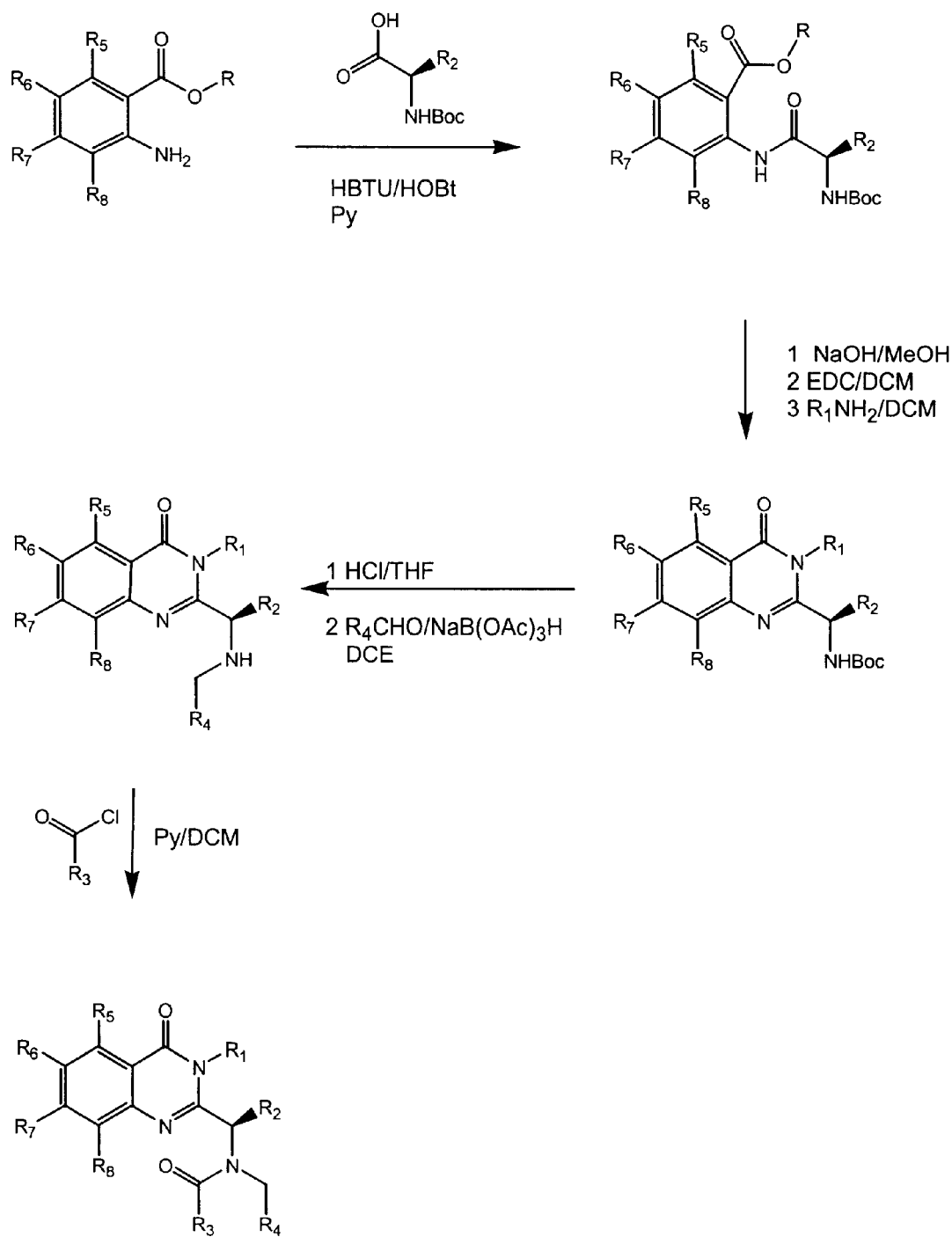
Figure 4: Asymmetric Synthesis

Figure 5
Figure 5a: Sulfonamide Synthesis
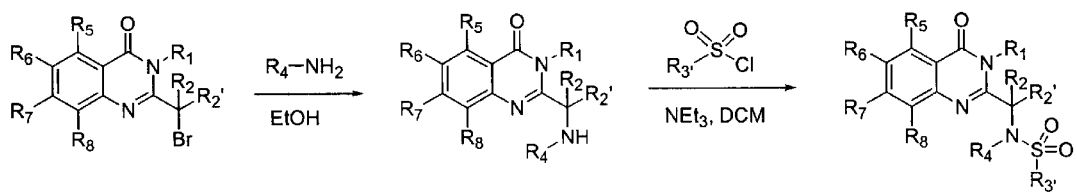
Figure 5b: Carbamate Synthesis
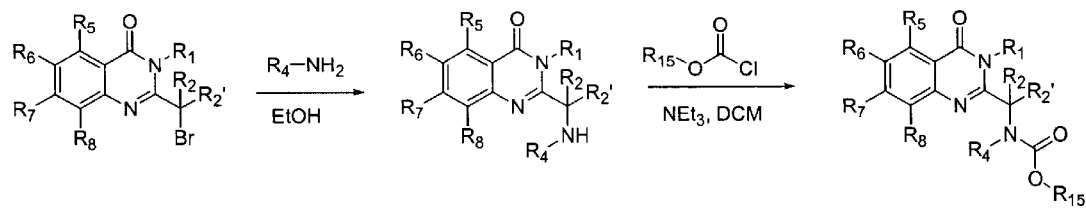
Figure 5c: Urea Synthesis
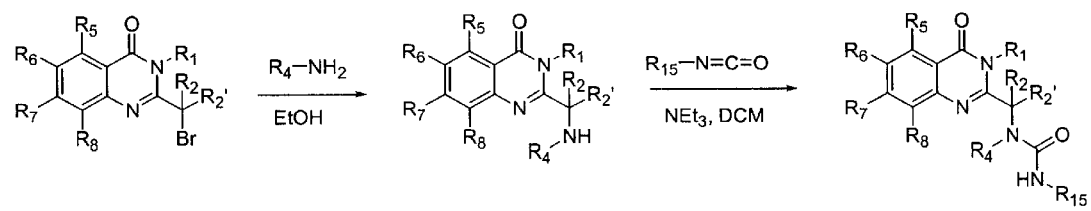
Figure 5d: Primary and Secondary Amine R4 Synthesis
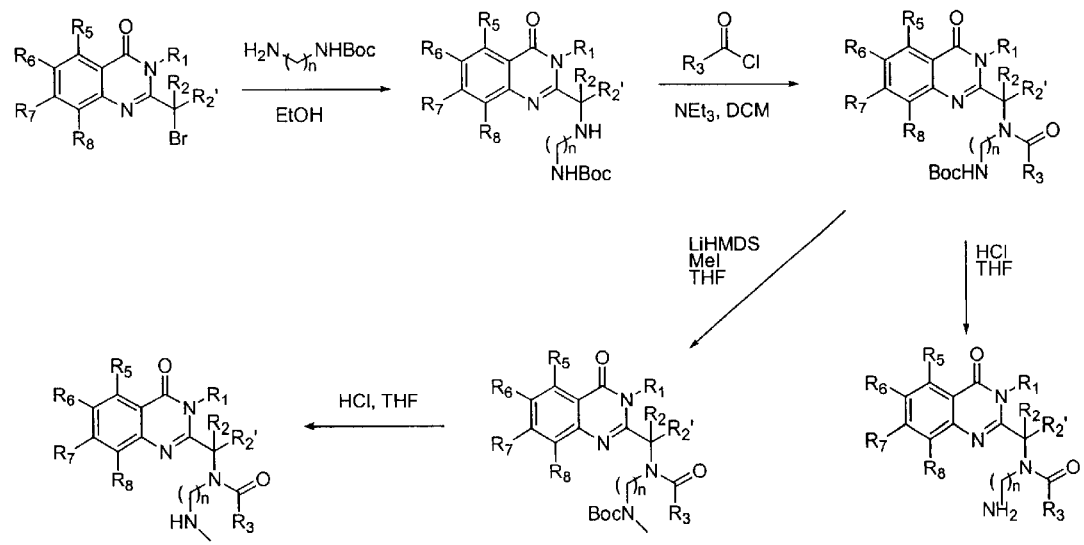

METHODS AND COMPOSITIONS UTILIZING QUINAZOLINONES

CROSS-REFERENCE TO RELATED APPLICATION

This application claims priority under 35 USC 119(e) from U.S. Provisional Application No. 60/198,253, having Jeffrey T. Finer as the inventor, filed Oct. 27, 1999, and titled "METHODS AND COMPOSITIONS UTILIZING QUINAZOLINONES", which is incorporated by reference herein for all purposes; it also claims priortity under 35 USC 119(e) from U.S. Provisional Patent Application No. 60/213, 104, having Jeffrey T. Finer et al. as inventors, filed Jun. 21, 2000, and titled "METHODS AND COMPOSITIONS UTILIZING QUINAZOLINONES", which is incorporated by reference herein for all purposes.

FIELD OF THE INVENTION

This invention relates to quinazolinone derivatives which are inhibitors of the mitotic kinesin KSP and are useful in the treatment of cellular proliferative diseases, for example cancer, hyperplasias, restenosis, cardiac hypertrophy, immune disorders and inflammation.

BACKGROUND OF THE INVENTION

Interest in the medicinal chemistry of quinazoline derivatives was stimulated in the early 1950's with the elucidation of the structure of a quinazoline alkaloid, 3-[β-keto-gamma-(3-hydroxy-2-piperidyl)-propyl]-4-quinazolone, from an Asian plant known for its antimalarial properties. In a quest to find additional antimalarial agents, various substituted quinazolines have been synthesized. Of particular import was the synthesis of the derivative 2-methyl-3-o-tolyl-4-(3H)-quinazolinone. This compound, known by the name methaqualone, though ineffective against protozoa, was found to be a potent hypnotic.

Since the introduction of methaqualone and its discovery as a hypnotic, the pharmacological activity of quinazolinones and related compounds has been investigated. Quinazolinones and derivatives thereof are now known to have a wide variety of biological properties including hypnotic, sedative, analgesic, anticonvulsant, antitussive and anti-inflammatory activities.

Quinazolinone derivatives for which specific biological uses have been described include U.S. Pat. No. 5,147,875 describing 2-(substituted phenyl)-4-oxo quinazolines with bronchodilator activity. U.S. Pat. Nos. 3,723,432, 3,740,442, and 3,925,548 describe a class of 1-substituted-4-aryl-2 (1H)-quinazolinone derivatives useful as anti-inflammatory agents. European patent publication EP 0 056 637 B1 claims a class of 4(3H)-quinazolinone derivatives for the treatment of hypertension. European patent publication EP 0 884 319 A1 describes pharmaceutical compositions of quinazolin-4-one derivatives used to treat neurodegenerative, psychotropic, and drug and alcohol induced central and peripheral nervous system disorders.

Quinazolinones are among a growing number of therapeutic agents used to treat cell proliferative disorders, including cancer. For example, PCT WO 96/06616 describes a pharmaceutical composition containing a quinazolinone derivative to inhibit vascular smooth cell proliferation. PCT WO 96/19224 uses this same quinazolinone derivative to inhibit mesengial cell proliferation. U.S. Pat. Nos. 4,981, 856, 5,081,124 and 5,280,027 describe the use of quinazolinone derivatives to inhibit thymidylate synthase, the enzyme that catalyzes the methylation of deoxyuridine monophosphate to produce thymidine monophosphate which is required for DNA synthesis. U.S. Pat. Nos. 5,747,498 and 5,773,476 describe quinazolinone derivatives used to treat cancers characterized by over-activity or inappropriate activity of tyrosine receptor kinases. U.S. Pat. No. 5,037,829 claims (1H-azol-1-ylmethyl) substituted quinazoline compositions to treat carcinomas which occur in epithelial cells. PCT WO 98/34613 describes a composition containing a quinazolinone derivative useful for attenuating neovascularization and for treating malignancies. U.S. Pat. No. 5,187, 167 describes pharmaceutical compositions comprising quinazolin-4-one derivatives which possess anti-tumor activity.

Other therapeutic agents used to treat cancer include the taxanes and vinca alkaloids. Taxanes and vinca alkaloids act on microtubules, which are present in a variety of cellular structures. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers.

During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described [Blangy, et al., Cell, 83:1159–69 (1995); Whitehead, et al., Arthritis Rheum., 39:1635–42 (1996); Galgio et al., J. Cell Biol., 135:339–414 (1996); Blangy, et al., J Biol. Chem., 272:19418–24 (1997); Blangy, et al., Cell Motil Cytoskeleton, 40:174–82 (1998); Whitehead and Rattner, J. Cell Sci., 111:2551–61 (1998); Kaiser, et al., JBC 274:18925–31 (1999); GenBank accession numbers: X85137, NM004523 and U37426], and a fragment of the KSP gene (TRIP5) has been described [Lee, et al., Mol Endocrinol., 9:243–54 (1995); GenBank accession number L40372]. Xenopus KSP homologs (Eg5), as well as Drosophila KLP61 F/KRP1 30 have been reported.

Mitotic kinesins are attractive targets for the discovery and development of novel mitotic chemotherapeutics. Accordingly, it is an object of the present invention to provide methods and compositions useful in the inhibition of KSP, a mitotic kinesin.

SUMMARY OF THE INVENTION

In accordance with the objects outlined above, the present invention provides compositions and methods that can be used to treat diseases of proliferating cells. The compositions are KSP inhibitors, particularly human KSP inhibitors.

In one aspect, the invention relates to methods for treating cellular proliferative diseases, for treating disorders associated with KSP kinesin activity, and for inhibiting KSP kinesin. The methods employ compounds chosen from the group consisting of:

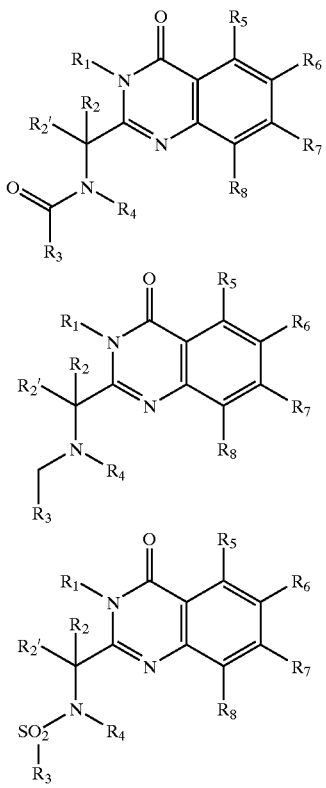

-continued
and

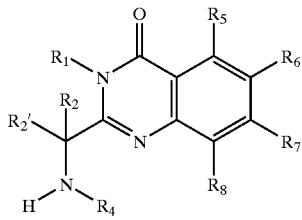

wherein:
$R_1$ is chosen from hydrogen, alkyl, aryl, alkylaryl, heteroaryl, alkylheteroaryl, substituted alkyl, substituted aryl, substituted alkylaryl, substituted heteroaryl, and substituted alkylheteroaryl;

$R_2$ and $R_2'$ are independently chosen from hydrogen, alkyl, oxaalkyl, aryl, alkylaryl, heteroaryl, alkylheteroaryl, substituted alkyl, substituted aryl, substituted alkylaryl, substituted heteroaryl, and substituted alkylheteroaryl; or $R_2$ and $R_2'$ taken together form a 3- to 7-membered ring;

$R_3$ is chosen from hydrogen, alkyl, aryl, alkylaryl, heteroaryl, alkylheteroaryl, substituted alkyl, substituted aryl, substituted alkylaryl, substituted heteroaryl, substituted alkylheteroaryl, oxaalkyl, oxaalkylaryl, substituted oxaalkylaryl, $R_{15}O—$ and $R_{15}—NH—$;

$R_{3'}$ is chosen from hydrogen, alkyl, aryl, alkylaryl, heteroaryl, alkylheteroaryl, substituted alkyl, substituted aryl, substituted alkylaryl, substituted heteroaryl, substituted alkylheteroaryl and $R_{15}—NH—$;

$R_{3''}$ is chosen from alkyl, aryl, alkylaryl, heteroaryl, alkylheteroaryl, substituted alkyl, substituted aryl, substituted alkylaryl, substituted heteroaryl, and substituted alkylheteroaryl;

$R_4$ is chosen from hydrogen, alkyl, aryl, alkylaryl, heteroaryl, alkylheteroaryl, substituted alkyl, substituted aryl, substituted alkylaryl, substituted heteroaryl, substituted alkylheteroaryl, and $R_{16}$-alkylene-;

$R_5$, $R_6$, $R_7$ and $R_8$ are independently chosen from hydrogen, alkyl, alkoxy, halogen, fluoroalkyl, nitro, dialkylamino, alkylsulfonyl, alkylsulfonamido, sulfonamidoalkyl, sulfonamidoaryl, alkylthio, carboxyalkyl, carboxamido, aminocarbonyl, aryl and heretoaryl;

$R_{15}$ is chosen from alkyl, aryl, alkylaryl, heteroaryl, alkylheteroaryl, substituted alkyl, substituted aryl, substituted alkylaryl, substituted heteroaryl, and substituted alkylheteroaryl;

$R_{16}$ is chosen from alkoxy, amino, alkylamino, dialkylamino, N-heterocyclyl and substituted N-heterocyclyl.

Diseases and disorders that respond to therapy with compounds of the invention include cancer, hyperplasia, restenosis, cardiac hypertrophy, immune disorders and inflammation.

In another aspect, the invention relates to compounds useful in inhibiting KSP kinesin. The compounds have the structures shown above.

In an additional aspect, the present invention provides methods of screening for compounds that will bind to a KSP kinesin, for example compounds that will displace or compete with the binding of the compositions of the invention. The methods comprise combining a labeled compound of the invention, a KSP kinesin, and at least one candidate agent and determining the binding of the candidate bioactive agent to the KSP kinesin.

In a further aspect, the invention provides methods of screening for modulators of KSP kinesin activity. The methods comprise combining a composition of the invention, a KSP kinesin, and at least one candidate agent and determining the effect of the candidate bioactive agent on the KSP kinesin activity.

BRIEF DESCRIPTION OF THE DRAWINGS

FIG. 2 depicts a synthetic route for the synthesis of quinazolinone KSP inhibitors.

DETAILED DESCRIPTION OF THE INVENTION

Figure 1:
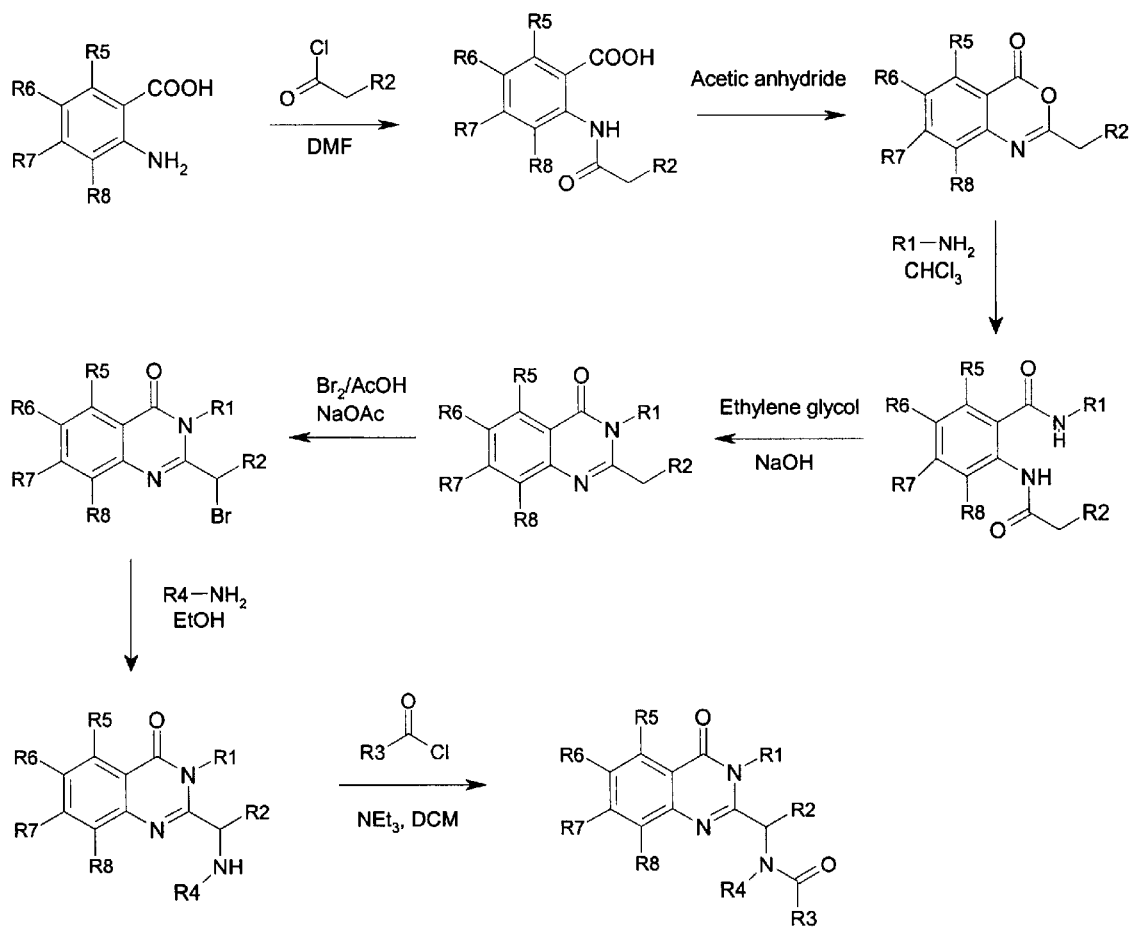
FIG. 1 depicts a generic synthetic scheme to make compositions of the invention.

The present invention is directed to a class of novel compounds, based on a core quinazolinone structure, that are modulators of mitotic kinesins. By inhibiting or modulating mitotic kinesins, but not other kinesins (e.g., transport kinesins), specific inhibition of cellular proliferation is accomplished. Thus, the present invention capitalizes on the finding that perturbation of mitotic kinesin function causes malformation or dysfunction of mitotic spindles, frequently resulting in cell cycle arrest and cell death. The methods of inhibiting a human KSP kinesin comprise contacting an inhibitor of the invention with a KSP kinesin, particularly human KSP kinesins, including fragments and variants of KSP. The inhibition can be of the ATP hydrolysis activity of the KSP kinesin and/or the mitotic spindle formation activity, such that the mitotic spindles are disrupted. Meiotic spindles may also be disrupted.

An object of the present invention is to develop inhibitors and modulators of mitotic kinesins, in particular KSP, for the treatment of disorders associated with cell proliferation. Traditionally, dramatic improvements in the treatment of cancer, one type of cell proliferative disorder, have been associated with identification of therapeutic agents acting through novel mechanisms. Examples of this include not only the taxane class of agents that appear to act on microtubule formation, but also the camptothecin class of topoisomerase I inhibitors. The compositions and methods described herein can differ in their selectivity and are preferably used to treat diseases of proliferating cells, including, but not limited to cancer, hyperplasias, restenosis, cardiac hypertrophy, immune disorders and inflammation.

Accordingly, the present invention relates to methods employing quinazolinone amides of formula 1a:

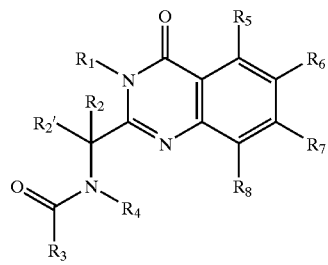

quinazolinone sulfonamides of formula 1b

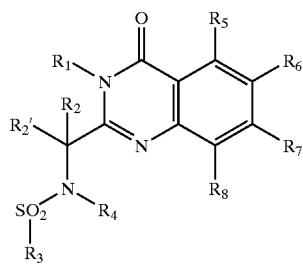

and quinazolinone amines of formulae 1c and 1d

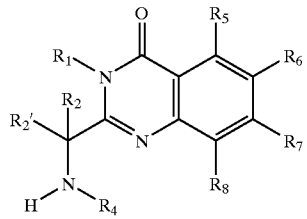

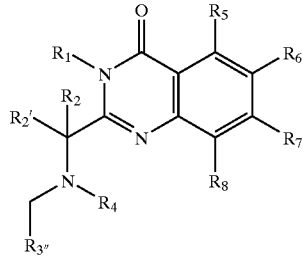

wherein:
  $R_1$ is chosen from hydrogen, alkyl, aryl, alkylaryl, heteroaryl, alkylheteroaryl, substituted alkyl, substituted aryl, substituted alkylaryl, substituted heteroaryl, and substituted alkylheteroaryl;
  $R_2$ and $R_2'$ are independently chosen from hydrogen, alkyl, oxaalkyl, aryl, alkylaryl, heteroaryl, alkylheteroaryl, substituted alkyl, substituted aryl, substituted alkylaryl, substituted heteroaryl, and substituted alkylheteroaryl; or $R_2$ and $R_2'$ taken together form a 3- to 7-membered ring;
  $R_3$ is chosen from hydrogen, alkyl, aryl, alkylaryl, heteroaryl, alkylheteroaryl, substituted alkyl, substituted aryl, substituted alkylaryl, substituted heteroaryl, substituted alkylheteroaryl, oxaalkyl, oxaalkylaryl, substituted oxaalkylaryl, $R_{15}O—$ and $R_{15}—NH—$;

$R_{3'}$ is chosen from hydrogen, alkyl, aryl, alkylaryl, heteroaryl, alkylheteroaryl, substituted alkyl, substituted aryl, substituted alkylaryl, substituted heteroaryl, substituted alkylheteroaryl, and $R_{15}—NH—$;

$R_{3''}$ is chosen from alkyl, aryl, alkylaryl, heteroaryl, alkylheteroaryl, substituted alkyl, substituted aryl, substituted alkylaryl, substituted heteroaryl, and substituted alkylheteroaryl;

$R_4$ is chosen from hydrogen, alkyl, aryl, alkylaryl, heteroaryl, alkylheteroaryl, substituted alkyl, substituted aryl, substituted alkylaryl, substituted heteroaryl, substituted alkylheteroaryl, and $R_{16}$-alkylene-;

$R_5$, $R_6$, $R_7$ and $R_8$ are independently chosen from hydrogen, alkyl, alkoxy, halogen, fluoroalkyl, nitro, dialkylamino, alkylsulfonyl, alkylsulfonamido, sulfonamidoalkyl, sulfonamidoaryl, alkylthio, carboxyalkyl, carboxamido, aminocarbonyl, aryl and heteroaryl;

$R_{15}$ is chosen from alkyl, aryl, alkylaryl, heteroaryl, alkylheteroaryl, substituted alkyl, substituted aryl, substituted alkylaryl, substituted heteroaryl, and substituted alkylheteroaryl;

$R_{16}$ is chosen from alkoxy, amino, alkylamino, dialkylamino, N-heterocyclyl and substituted N-heterocyclyl.

All of the compounds falling within the foregoing parent genus and its subgenera are useful as kinesin inhibitors, but not all the compounds are novel. In particular, certain ureas (i.e. compounds in which $R_3$ is $R_{15}NH$) are disclosed in U.S. Pat. No. 5,756,502 as agents which modify cholecystokinin action. The specific exceptions in the claims reflect applicants' intent to avoid claiming subject matter that, while functionally part of the inventive concept, is not patentable to them for reasons having nothing to do with the scope of the invention.

Definitions

Alkyl is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, isopropyl, butyl, s- and t-butyl and the like. Preferred alkyl groups are those of $C_{20}$ or below. More preferred alkyl groups are those of $C_{13}$ or below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene refers to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Alkylaryl refers to a residue in which an aryl moiety is attached to the parent structure via an alkyl residue. Examples are benzyl, phenethyl, phenylvinyl, phenylallyl and the like. Oxaalkyl and oxaalkylaryl refer to alkyl and alkylaryl residues in which one or more methylenes have been replaced by oxygen. Examples of oxaalkyl and oxaalkylaryl residues are ethoxyethoxyethyl (3,6-dioxaoctyl), benzyloxymethyl and phenoxymethyl; in general, glycol ethers, such as polyethyleneglycol, are intended to be encompassed by this group. Alkylheteroaryl refers to a residue in which a heteroaryl moiety is attached to the parent structure via an alkyl residue. Examples include furanylmethyl, pyridinylmethyl, pyrimidinylethyl and the like.

Heterocycle means a cycloalkyl or aryl residue in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

Substituted alkyl, aryl and heteroaryl refer to alkyl, aryl or heteroaryl wherein H atoms are replaced with alkyl, halogen, hydroxy, alkoxy, alkylenedioxy (e.g. methylenedioxy)fluoroalkyl, carboxy (—COOH), carboalkoxy (i.e. acyloxy RCOO—), carboxyalkyl (—COOR), carboxamido, sulfonamidoalkyl, sulfonamidoaryl, aminocarbonyl, benzyloxycarbonylamino (CBZ-amino), cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy. For the purposes of the present invention, substituted alkyl also includes oxaalkyl residues, i.e. alkyl residues in which one or more carbons has been replaced by oxygen.

Halogen refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

Most of the compounds described herein contain one or more asymmetric centers (e.g. the carbon to which $R_2$ and $R_2'$ are attached) and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

Figures 1, 3A:
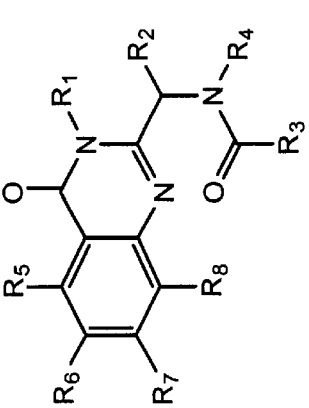
Figures 3, 3A, 4, 5, 6, 7, 8, 9, 10, 11, 12, 13, 14, 15, 16, 17, 18, 19, 20, 21, 22, 23, 24, 25, 26, 27, 28, 29, 30, 31:
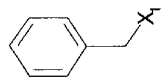
FIG. 3 depicts representative chemical structures of quinazolinone KSP inhibitors.
FIG. 4 depicts a synthetic route to substantially pure single enantiomers.
FIG. 5 depicts synthetic routes to sulfonamides (5a), carbamates (5b), ureas (5c) and amines (5d).
Figures 3, 3A, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
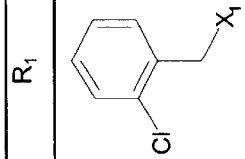
Figures 3A, 59:
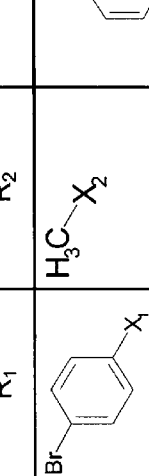
Figures 3A, 73:
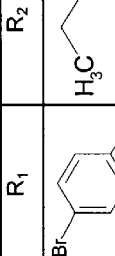

When desired, the R— and S-isomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by symmetric transformation. An example of a synthesis from optically active starting materials is shown in FIG. 4.

In one embodiment, as will be appreciated by those in the art, the two adjacent $R_2$ groups may be fused together to form a ring structure. Again, the fused ring structure may contain heteroatoms and may be substituted with one or more substitution groups "R". It should additionally be noted that for cycloalkyl (i.e. saturated ring structures), each position may contain two substitution groups, R and R'.

Considering structures 1a, 1b, 1c and 1d, but focusing on 1a, in a preferred embodiment $R_1$ is selected from hydrogen, alkyl, aryl, substituted alkyl, substituted aryl, heteroaryl, substituted heteroaryl, alkylaryl and substituted alkylaryl.

In a more preferred embodiment $R_1$ is selected from hydrogen, lower alkyl, substituted lower alkyl, benzyl, substituted benzyl, phenyl, naphthyl and substituted phenyl.

In a most preferred embodiment $R_1$ is chosen from hydrogen, ethyl, propyl, methoxyethyl, naphthyl, phenyl, bromophenyl, chlorophenyl, methoxyphenyl, ethoxyphenyl, tolyl, dimethylphenyl, chorofluorophenyl, methylchlorophenyl, ethylphenyl, phenethyl, benzyl, chlorobenzyl, methylbenzyl, methoxybenzyl, cyanobenzyl, hydroxybenzyl, tetrahydrofuranylmethyl and (ethoxycarbonyl)ethyl.

In a preferred embodiment $R_2$ is hydrogen, alkyl or substituted alkyl. As will be appreciated by those in the art, Structures 1a, 1b, 1c and 1d possess a potentially chiral center at the carbon to which $R_2$ is attached. Thus, the $R_2$ position may comprise two substitution groups, $R_2$ and $R_2'$. The $R_2$ and $R_2'$ groups may be the same or different; if different, the composition is chiral. When the $R_2$ and $R_2'$ are different, preferred embodiments utilize only a single non-hydrogen $R_2$. The invention contemplates the use of pure enantiomers and mixtures of enantiomers, including racemic mixtures, although the use of the substantially optically pure eutomer will generally be preferred.

In a more preferred embodiment, $R_2$ is chosen from hydrogen, lower alkyl and substituted lower alkyl, and $R_2'$ is hydrogen. In a most preferred embodiment $R_2$ is chosen from hydrogen, methyl, ethyl, propyl, methylthioethyl, aminobutyl, (CBZ)aminobutyl, cyclohexylmethyl, benzyloxymethyl, methylsulfinylethyl, methylsulfinylmethyl, hydroxymethyl, benzyl and indolylmethyl.

In a preferred embodiment $R_3$ is selected from chosen from alkyl, substituted alkyl, alkylaryl, heteroaryl, aryl, substituted aryl, substituted oxaalkylaryl, $R_{15}O$— and $R_{15}$—NH—, and $R_{15}$ is chosen from alkyl, aryl and substituted aryl.

In a more preferred embodiment, when $R_3$ is not $R_{15}NH$, $R_3$ is chosen from $C_1$–$C_{13}$ alkyl; substituted lower alkyl; phenyl; naphthyl; phenyl substituted with one or more halo, lower alkyl, loweralkoxy, nitro, carboxy, methylenedioxy or trifluoromethyl; biphenylyl; benzyl; phenoxymethyl; halophenoxymethyl; phenylvinyl; heteroaryl; heteroaryl substituted with lower alkyl; and benzyloxymethyl.

In a most preferred embodiment, when $R_3$ is not $R_{15}NH$, $R_3$ is chosen from ethyl, propyl, chloropropyl, butoxy, heptyl, butyl, octyl, tridecanyl, (ethoxycarbonyl)ethyl, dimethylaminoethyl, dimethylaminomethyl, phenyl, naphthyl, halophenyl, dihalophenyl, cyanophenyl, halo(trifluoromethyl)phenyl, chlorophenoxymethyl, methoxyphenyl, carboxyphenyl, ethylphenyl, tolyl, biphenylyl, methylenedioxyphenyl, methylsulfonylphenyl, methoxychlorophenyl, chloronaphthyl, methylhalophenyl, trifluoromethylphenyl, butylphenyl, pentylphenyl, methylnitrophenyl, phenoxymethyl, dimethoxyphenyl, phenylvinyl, nitrochlorophenyl, nitrophenyl, dinitrophenyl, bis(trifluoromethyl)phenyl, benzyloxymethyl, benzyl, furanyl, benzofuranyl, pyridinyl, indolyl, methylpyridinyl, quinolinyl, picolinyl, pyrazolyl, and imidazolyl.

In a more preferred embodiment, when $R_3$ is $R_{15}NH$, $R_{15}$ is chosen from lower alkyl; cyclohexyl; phenyl; and phenyl substituted with halo, lower alkyl, loweralkoxy, or lower alkylthio.

In a most preferred embodiment, when $R_3$ is $R_{15}NH$, $R_{15}$ is isopropyl, butyl, cyclohexyl, phenyl, bromophenyl, dichlorophenyl, methoxyphenyl, ethylphenyl, tolyl, trifluoromethylphenyl or methylthiophenyl.

In a preferred embodiment $R_4$ is chosen from alkyl, aryl, alkylaryl, alkylheteroaryl, substituted alkyl, substituted aryl, and $R_{16}$-alkylene-, and $R_{16}$ is chosen from alkoxy, amino, alkylamino, dialkylamino and N-heterocyclyl.

In a more preferred embodiment, $R_4$ is selected from lower alkyl, substituted lower alkyl, cyclohexyl; phenyl substituted with hydroxy, lower alkoxy or lower alkyl; benzyl; heteroarylmethyl; heteroarylethyl; heteroarylpropyl and $R_{16}$-alkylene-, wherein $R_{16}$ is amino, lower alkylamino, di(lower alkyl)amino, lower alkoxy, or N-heterocyclyl.

In a most preferred embodiment, $R_4$ is chosen from methyl, ethyl, propyl, butyl, cyclohexyl, carboxyethyl, carboxymethyl, methoxyethyl, hydroxyethyl, hydroxypropyl, dimethylaminoethyl, dimethylaminopropyl, diethylaminoethyl, diethylaminopropyl, aminopropyl, methylaminopropyl, 2,2-dimethyl-3-(dimethylamino) propyl, 1-cyclohexyl-4-(diethylamino)butyl, aminoethyl, aminobutyl, aminopentyl, aminohexyl, aminoethoxyethyl, isopropylaminopropyl, diisopropylaminoethyl, 1-methyl-4-(diethylamino)butyl, (t-Boc)aminopropyl, hydroxyphenyl, benzyl, methoxyphenyl, methylmethoxyphenyl, dimethylphenyl, tolyl, ethylphenyl, (oxopyrrolidinyl)propyl, (methoxycarbonyl)ethyl, benzylpiperidinyl, pyridinylethyl, pyridinylmethyl, morpholinylethyl morpholinylpropyl, piperidinyl, azetidinylmethyl, azetidinylpropyl pyrrolidinylethyl, pyrrolidinylpropyl, piperidinylmethyl, piperidinylethyl, imidazolylpropyl, imidazolylethyl, (ethylpyrrolidinyl)methyl, (methylpyrrolidinyl)ethyl, (methylpiperidinyl)propyl, (methylpiperazinyl)propyl, furanylmethyl and indolylethyl.

In other preferred embodiments $R_5$ is hydrogen or halo; $R_6$ is hydrogen, methyl or halo; $R_7$ is hydrogen, halo, methyl or trifluoromethyl; and $R_8$ is hydrogen or halo.

In a particularly preferred subgenus, $R_1$ is benzyl or halobenzyl; $R_2$ is chosen from ethyl and propyl; $R_2'$ is hydrogen; $R_3$ is substituted phenyl; $R_3$ is substituted phenyl; $R_{3''}$ is substituted phenyl; $R_4$ is —(CH)$_m$OH or —(CH$_2$)$_p$ $R_{16}$; m is two or three; p is one to three; $R_5$ is hydrogen; $R_6$ is hydrogen; $R_7$ is halo; $R_8$ is hydrogen; and $R_{16}$ is chosen from amino, propylamino, and azetidinyl.

When considering primarily the sulfonamides of structure 1b, $R_1$ is preferably chosen from hydrogen, lower alkyl, substituted lower alkyl, benzyl, substituted benzyl, phenyl and substituted phenyl; $R_2$ is chosen from hydrogen and lower alkyl and $R_2'$ is hydrogen; $R_3$ is chosen from $C_1$–$C_{13}$ alkyl; phenyl; naphthyl; phenyl substituted with halo, lower alkyl, lower alkoxy, nitro, methylenedioxy, or trifluoromethyl; biphenylyl and heteroaryl; and $R_4$ is chosen from lower alkyl, cyclohexyl; phenyl substituted with hydroxy, lower alkoxy or lower alkyl; benzyl; heteroarylmethyl; heteroarylethyl; heteroarylpropyl; heteroarylethyl; heteroarylpropyl and $R_{16}$-alkylene, wherein $R_{16}$ is di(lower alkyl)amino, (lower alkyl)amino, amino, lower alkoxy, or N-heterocyclyl, particularly pyrrolidino, piperidino or imidazolyl.

When considering primarily the sulfonamides of structure 1b, $R_1$ is most preferably chosen from lower alkyl, benzyl, substituted benzyl and substituted phenyl; $R_2$ is hydrogen or lower alkyl; $R_2'$ is hydrogen; $R_3$ is chosen from substituted phenyl and naphthyl; $R_4$ is $R_{16}$-alkylene-; $R_7$ is hydrogen, fluoro, methyl or chloro; $R_5$ $R_6$ and $R_8$ are hydrogen; and $R_{16}$ is chosen from di(lower alkylamino), (lower alkyl)amino, amino, pyrrolidino, piperidino, imidazolyl and morpholino.

When considering primarily the amines of structures 1c and 1d, $R_1$ is preferably chosen from hydrogen, lower alkyl, substituted lower alkyl, benzyl, substituted benzyl, phenyl, naphthyl and substituted phenyl; $R_2$ is chosen from hydrogen, lower alkyl and substituted lower alkyl and $R_2'$ is hydrogen; $R_{3''}$ is chosen from $C_1$–$C_{13}$ alkyl; substituted lower alkyl; phenyl; naphthyl; phenyl substituted with halo, lower alkyl, lower alkoxy, nitro, methylenedioxy, or trifluoromethyl; biphenylyl, benzyl and heterocyclyl; and $R_4$ is chosen from lower alkyl; cyclohexyl; phenyl substituted with hydroxy, lower alkoxy or lower alkyl; benzyl; substituted benzyl; heterocyclyl; heteroarylmethyl; heteroarylethyl; heteroarylpropyl and $R_{16}$-alkylene, wherein $R_{16}$ is di(lower alkyl)amino, (lower alkyl)amino, amino, lower alkoxy, or N-heterocyclyl.

When considering primarily the amines of structure 1c and 1d, $R_1$ is most preferably chosen from lower alkyl, benzyl, substituted benzyl and substituted phenyl; $R_2$ is hydrogen or lower alkyl; $R_2'$ is hydrogen; $R_{3''}$ is chosen from substituted phenyl, heterocyclyl and naphthyl; $R_4$ is chosen from subtituted benzyl, heterocyclyl and $R_{16}$-alkylene-; $R_6$ and $R_7$ are chosen from hydrogen and halo; $R_5$ and $R_8$ are hydrogen; and $R_{16}$ is chosen from di(lower alkylamino), (lower alkyl)amino, amino, pyrrolidinyl, piperidinyl, imidazolyl and morpholinyl. When $R_{3''}$ is present (as in 1d) it is most preferably chosen from halophenyl, polyhalophenyl, tolyl, dimethylphenyl, methoxyphenyl, dimethoxyphenyl, cyanophenyl, trifluoromethylphenyl, trifluoromethoxyphenyl, bis(trifluoromethyl)phenyl, carboxyphenyl, t-butylphenyl, methoxycarbonylphenyl, piperidinyl and naphthyl.

The compositions of the invention are synthesized as outlined below, utilizing techniques well known in the art. For example, as described in Ager et al., J. of Med. Chem., 20:379–386 (1977), hereby incorporated by reference, quinazolinones can be obtained by acid-catalyzed condensation of N-acylanthranilic acids with aromatic primary amines. Other processes for preparing quinazolinones are described in U.S. Pat. Nos. 5,783,577, 5,922,866 and 5,187,167, all of which are incorporated by reference.

The compositions of the invention may be made as shown in FIGS. 1, 2, 4 and 5. Compounds of formulae 1d are made in analogous fashion to FIG. 1, except that the acyl halide in the final step is replaced by an alkyl halide.

Once made, the compositions of the invention find use in a variety of applications. As will be appreciated by those in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a preferred embodiment, the compositions of the invention are used to modulate mitotic spindle formation, thus causing prolonged cell cycle arrest in mitosis. By "modulate" herein is meant altering mitotic spindle formation, including increasing and decreasing spindle formation. By "mitotic spindle formation" herein is meant organization of microtubules into bipolar structures by mitotic kinesins. By "mitotic spindle dysfunction" herein is meant mitotic arrest and monopolar spindle formation.

The compositions of the invention are useful to bind to and/or modulate the activity of mitotic kinesin, KSP. In a preferred embodiment, the KSP is human KSP, although KSP kinesins from other organisms may also be used. In this context, modulate means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See U.S. patent application "Methods of Screening for Modulators of Cell Proliferation and Methods of Diagnosing Cell Proliferation States", filed Oct. 27, 1999 (U.S. Ser. No. 09/428,156), hereby incorporated by reference in its entirety. In addition, other mitotic kinesins may be used in the present invention. However, the compositions of the invention have been shown to have specificity for KSP.

For assay of activity, generally either KSP or a compound according to the invention is non-diffusably bound to an insoluble support having isolated sample receiving areas (e.g., a microtiter plate, an array, etc.). The insoluble support may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

The antimitotic agents of the invention may be used on their own to modulate the activity of a mitotic kinesin, particularly KSP. In this embodiment, the mitotic agents of the invention are combined with KSP and the activity of KSP is assayed. Kinesin activity is known in the art and includes one or more kinesin activities. Kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes; such as kinases or proteases; and specific kinesin cellular activities such as spindle pole separation.

Methods of performing motility assays are well known to those of skill in the art. [See e.g., Hall, et al. (1996), Biophys. J., 71: 3467–3476, Turner et al., 1996, AnaL Biochem. 242 (1):20–5; Gittes et al., 1996, Biophys. J. 70(1): 418–29; Shirakawa et al., 1995, J. Exp. Biol. 198: 1809–15; Winkelmann et al., 1995, Biophys. J. 68: 2444–53; Winkelmann et al., 1995, Biophys. J. 68: 72S.]

Methods known in the art for determining ATPase hydrolysis activity also can be used. Preferably, solution based assays are utilized. U.S. application Ser. No. 09/314,464, filed May 18, 1999, hereby incorporated by reference in its entirety, describes such assays. Alternatively, conventional methods are used. For example, $P_i$ release from kinesin can be quantified. In one preferred embodiment, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 µL of reaction is quenched in 90 µL of cold 0.3 M PCA. Phosphate standards are used so data can be converted to mM inorganic phosphate released. When all reactions and standards have been quenched in PCA, 100 µL of malachite green reagent is added to the relevant wells in e.g., a microtiter plate. The mixture is developed for 10–15 minutes and the plate is read at an absorbance of 650 nm. If phosphate standards were used, absorbance readings can be converted to mM $P_i$ and plotted over time. Additionally, ATPase assays known in the art include the luciferase assay.

ATPase activity of kinesin motor domains also can be used to monitor the effects of modulating agents. In one embodiment ATPase assays of kinesin are performed in the absence of microtubules. In another embodiment, the ATPase assays are performed in the presence of microtubules. Different types of modulating agents can be detected in the above assays. In a preferred embodiment, the effect of a modulating agent is independent of the concentration of microtubules and ATP. In another embodiment, the effect of the agents on kinesin ATPase can be decreased by increasing the concentrations of ATP, microtubules or both. In yet another embodiment, the effect of the modulating agent is increased by increasing concentrations of ATP, microtubules or both.

Agents that modulate the biochemical activity of KSP in vitro may then be screened in vivo. Methods for such agents in vivo include assays of cell cycle distribution, cell viability, or the presence, morphology, activity, distribution, or amount of mitotic spindles. Methods for monitoring cell cycle distribution of a cell population, for example, by flow cytometry, are well known to those skilled in the art, as are methods for determining cell viability. See for example, U.S. patent application "Methods of Screening for Modulators of Cell Proliferation and Methods of Diagnosing Cell Proliferation States," filed Oct. 22, 1999, Ser. No. 09/428,156, hereby incorporated by reference in its entirety.

In addition to the assays described above, microscopic methods for monitoring spindle formation and malformation are well known to those of skill in the art (see, e.g., Whitehead and Rattner (1998), J. Cell Sci. 111:2551–61; Galgio et al, (1996) J. Cell biol., 135:399–414).

The compositions of the invention inhibit the KSP kinesin. One measure of inhibition is $IC_{50}$, defined as the concentration of the composition at which the activity of KSP is decreased by fifty percent. Preferred compositions have $IC_{50}$'s of less than about 1 mM, with preferred embodiments having $IC_{50}$'s of less than about 100 µM, with more preferred embodiments having $IC_{50}$'s of less than about 10 µM, with particularly preferred embodiments having $IC_{50}$'s of less than about 1 µM, and especially preferred embodiments having $IC_{50}$'s of less than about 100 nM, and with the most preferred embodiments having $IC_{50}$'s of less than about 10 nM. Measurement of $IC_{50}$ is done using an ATPase assay.

Another measure of inhibition is $K_i$. For compounds with $IC_{50}$'s less than 1 µM, the $K_i$ or $K_d$ is defined as the dissociation rate constant for the interaction of the quinazolinone with KSP. Preferred compounds have $K_i$'s of less than about 100 µM, with preferred embodiments having $K_i$'s of less than about 10 µM, and particularly preferred embodiments having $K_i$'s of less than about 1 µM and especially preferred embodiments having $K_i$'s of less than about 100 nM, and with the most preferred embodiments having $K_i$'s of less than about 10 nM. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0 \left[ 1 - \frac{(E_0 + I_0 + K_d) - \sqrt{(E_0 + I_0 + K_d)^2 - 4E_0I_0}}{2E_0} \right]$$

Where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Preferred compounds have $GI_{50}$'s of less than about 1 mM. The level of preferability of embodiments is a function of their $GI_{50}$: those having $GI_{50}$'s of less than about 20 $\mu$M are more preferred; those having $GI_{50}$'s of 10 $\mu$M more so; those having $GI_{50}$ of less than about 1 $\mu$M more so; those having $GI_{50}$'s of 100 nM more so; those having $GI_{50}$ of less than about 10 nM even more so. Measurement of $GI_{50}$ is done using a cell proliferation assay.

The compositions of the invention are used to treat cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Accordingly, the compositions of the invention are administered to cells. By "administered" herein is meant administration of a therapeutically effective dose of the mitotic agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Mitotic agents having the desired pharmacological activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1–100 wt. %. The agents may be administered alone or in combination with other treatments, i.e., radiation, or other chemotherapeutic agents.

In a preferred embodiment, the pharmaceutical compositions are in a water soluble form, such as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The administration of the mitotic agents of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the anti-mitotic agents may be directly applied as a solution or spray.

To employ the compounds of the invention in a method of screening for compounds that bind to KSP kinesin, the KSP is bound to a support, and a compound of the invention (which is a mitotic agent) is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the mitotic agent to KSP may be done in a number of ways. In a preferred embodiment, the mitotic agent (the compound of the invention) is labeled, for example, with a fluorescent or radioactive moiety and binding determined directly. For example, this may be done by attaching all or a portion of KSP to a solid support, adding a labeled mitotic agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}$I, or with fluorophores. Alternatively, more than one component may be labeled with different labels; using $^{125}$I for the proteins, for example, and a fluorophor for the mitotic agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, preferred embodiments exclude molecules already known to bind to that particular protein, for example, polymer structures such as microtubules, and energy sources such as ATP. Preferred embodiments of assays herein include candidate agents which do not bind the cellular proliferation protein in its endogenous native state termed herein as "exogenous" agents. In another preferred embodiment, exogenous agents further exclude antibodies to KSP.

Candidate agents can encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Competitive screening assays may be done by combining KSP and a drug candidate in a first sample. A second sample comprises a mitotic agent, KSP and a drug candidate. This may be performed in either the presence or absence of microtubules. The binding of the drug candidate is determined for both samples, and a change, or difference in binding between the two samples indicates the presence of an agent capable of binding to KSP and potentially modulating its activity. That is, if the binding of the drug candidate is different in the second sample relative to the first sample, the drug candidate is capable of binding to KSP.

In a preferred embodiment, the binding of the candidate agent is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to KSP and thus is capable of binding to, and potentially modulating, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

It may be of value to identify the binding site of KSP. This can be done in a variety of ways. In one embodiment, once KSP has been identified as binding to the mitotic agent, KSP is fragmented or modified and the assays repeated to identify the necessary components for binding.

Modulation is tested by screening for candidate agents capable of modulating the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morpohology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Abbreviations and Definitions

The following abbreviations and terms have the indicated meanings throughout:

| | | |
|---|---|---|
| Ac | = | acetyl |
| BNB | = | 4-bromomethyl-3-nitrobenzoic acid |
| Boc | = | t-butyloxy carbonyl |
| Bu | = | butyl |
| c- | = | cyclo |
| CBZ | = | carbobenzoxy = benzyloxycarbonyl |
| DBU | = | diazabicyclo[5.4.0]undec-7-ene |
| DCM | = | dichloromethane = methylene chloride = $CH_2Cl_2$ |
| DCE | = | dichloroethylene |
| DEAD | = | diethyl azodicarboxylate |
| DIC | = | diisopropylcarbodiimide |
| DIEA | = | N,N-diisopropylethyl amine |
| DMAP | = | 4-N,N-dimethylaminopyridine |
| DMF | = | N,N-dimethylformamide |
| DMSO | = | dimethyl sulfoxide |
| DVB | = | 1,4-divinylbenzene |
| EEDQ | = | 2-ethoxy-1-ethoxycarbonyl-1,2-dihydroquinoline |
| Et | = | ethyl |
| Fmoc | = | 9-fluorenylmethoxycarbonyl |
| GC | = | gas chromatography |
| HATU | = | O-(7-Azabenzotriazol-1-yl)-1,1,3,3-tetramethyluronium hexafluorophosphate |
| HMDS | = | hexamethyldisilazane |
| HOAc | = | acetic acid |
| HOBt | = | hydroxybenzotriazole |
| Me | = | methyl |
| mesyl | = | methanesulfonyl |
| MTBE | = | methyl t-butyl ether |
| NMO | = | N-methylmorpholine oxide |
| PEG | = | polyethylene glycol |
| Ph | = | phenyl |
| PhOH | = | phenol |
| PfP | = | pentafluorophenol |
| PPTS | = | pyridinium p-toluenesulfonate |
| Py | = | pyridine |
| PyBroP | = | bromo-tris-pyrrolidino-phosphonium hexafluorophosphate |
| rt | = | room temperature |
| sat=d | = | saturated |
| s- | = | secondary |
| t- | = | tertiary |
| TBDMS | = | t-butyldimethylsilyl |
| TES | = | triethylsilane |
| TFA | = | trifluoroacetic acid |
| THF | = | tetrahydrofuran |
| TMOF | = | trimethyl orthoformate |
| TMS | = | trimethylsilyl |
| tosyl | = | p-toluenesulfonyl |
| Trt | = | triphenylmethyl |

Example 1

Synthesis of Compounds

The general synthesis is shown in FIGS. 1 and 2.

Step 1: N-butyryl anthranilic acid.

To a three-necked, 500 mL round-bottom flask equipped with a thermometer, dropping funnel, and an efficient magnetic stir bar, was added anthranilic acid (1) (0.5 mole, 68.5 g) and dimethyl formamide (250 mL). To this solution was added butyryl chloride (0.55 mole, 57.1 mL) dropwise at such a rate that the temperature of the mixture did not rise above 40° C. The suspension was stirred vigorously at room temperature for at least an additional 3 h. The mixture was poured into water (2000 mL) and stirred for another 1 h. The precipitated product was collected by filtration, washed with cold water, and dried under reduced pressure over $P_2O_5$, yielding compound 2 (67.3 g, 65%).

Step 2: 2-Propyl-3,1-[4H]benzoxazin-4-one.

Compound 2 (51.8 g, 0.25 mole) was dissolved in acetic anhydride (180 mL) in a 500 mL round-bottom flask equipped with a magnetic stir bar, a Claisen-distillation head (with vacuum inlet) and a thermometer. The flask was placed in an oil bath and slowly heated to 170–180° C. with vigorous stirring. The acetic acid produced was slowly distilled off under atmospheric pressure. Monitoring the head temperature of the distillation unit was used to follow the progress of the transformation. The reaction mixture was then cooled to 60° C. and the excess of acetic anhydride removed by distillation under reduced pressure (ca. 20 mm Hg). The residue was afterward cooled and the product crystallized. The product was triturated with n-hexane (75 mL) and isolated by filtration to yield 2-propyl-3,1-[4H] benzoxazin-4-one (3) (29.3 g, 62%). The above procedure gave compound 3 sufficiently pure to use directly in the next step.

Step 3: 2-Propyl-3-benzylquinazolin-4-one.

Compound 3 (28.4 g, 0.15 mole) and benzylamine (17.5 mL, 0.16 mole) were refluxed in chloroform (50 ml) in a one-neck 250 mL round-bottom flask for 6 h. After complete consumption of compound 3, the chloroform was evaporated under reduced pressure. Ethylene glycol (100 mL) and NaOH pellets (0.60 g) were added to the residue and the flask equipped with a Claisen-distillation head and a magnetic stir bar. The flask was immersed in an oil bath and reheated to 130–140° C. bath temperature with vigorous stirring and maintained there for 5 h while the water produced was removed by distillation. After completion of the reaction, the clear solution was allowed to cool to room temperature and kept overnight to precipitate the product. The pH of the suspension was adjusted to 7–8 by adding 3% aq. HCl, the crystals were filtered off and washed with cold water, and then recrystallized from isopropanol (or alternatively from acetone) to provide the compound, 2-propyl-3-benzylquinazolin-4-one (compound 4) (28.0 g, 67%).

Step 4: 2-(1'-bromopropyl)-3-benzylquinazolin-4-one.

To a three-neck 250 mL round-bottom flask equipped with a thermometer, dropping funnel, and efficient magnetic stir bar was added compound 4 (27.8 g, 0.10 mole), anhydrous sodium acetate (10.0 g) and glacial acetic acid (130 mL). Bromine (16.0 g, 0.10 mole) dissolved in acetic acid (10 mL) was added dropwise to the above solution at 40° C. for 1–2 h. After addition was complete, the mixture was poured into water (1500 mL) and stirred for 1–2 h at room temperature. The precipitated product, 2-(1'-bromopropyl)-benzylquinazolin-4-one (5) was isolated by filtration, washed with warm water to remove traces of acetic acid, and rinsed with a small amount of isopropanol. Drying yielded compound 5 (33.0 g, 92%).

Step 5: 2-[1'-(N,N-dimethylethylenediamino)propyl]-3-benzylquinazolin-4-one.

Compound 5: (10.7 g, 0.03 mole) and N,N-dimethylethylenediamine (6.6 mL, 0.06 mole) were dissolved in abs. ethanol (60 mL) and heated at reflux for 6 h. After completion of the reaction, the solvent was evaporated under reduced pressure. The residue was dissolved in dichloromethane (150 mL) and washed with 3% aq. NaOH solution (ca. 10–20 mL). The organic layer was dried over $MgSO_4$ and evaporated to dryness under reduced pressure. The remaining oily product was purified by flash chromatography on a short silica gel pad using an eluent of $CHCl_3$—MeOH-aq.$NH_3$, 90:10:0.1, to give the desired compound (5), 2-[1'-(N,N-dimethylethylenediamino) propyl]-3-benzylquinazolin-4-one (6) (6.0 g, 55%).

Step 6: 2-[1'-(N-4-fluorobenzoyl)-(N,N-dimethylethylenediamino)propyl]-3-benzylquinazolin-4-one.

A stock solution of compound 5 (1.822 g, 5.0 mmol) was prepared in HPLC grade $CHCl_3$ (0.5 mL). A stock solution of p-flurobenzoyl chloride (160.2 mg, 1 mmol) in HPLC grade 1,2-dichloroethane (2.0 mL) was prepared in a 2.0 mL volumetric flask. A third solution of triethylamine (2.0 mL of 0.5 M) was prepared in HPLC grade 1,2-dichlorethane. A 100 µL aliquot of each solution was pipetted into a glass reaction vessel using a Beckman Biomet 2000 automated liquid dispenser. The reaction mixture was shaken using a mechanical shaker, sonicated in an ultrasonic water bath, and then incubated overnight at room temperature. The mixture was diluted in $CHCl_3$ (300 µL) and washed with 5% aqueous $NaHCO_3$ and water. The solvent was removed in vacuo to provide compound 6 (65%). The purity of the compound was analyzed by TLC eluted with $CH_2Cl_2$-ethanol-concentrated aqueous $NH_3$, 100:10:1.

Examples 2 and 3

Synthesis of Compounds of General Structure 1d multichannel pipettors. Filtrations were performed using Whatman/Polyfiltronics 24 well, 10 mL filtration blocks. Evaporation of volatile materials from the array was performed with a Labconco Vortex-Evaporator or by sweeping with a 4×6 nitrogen manifold.

Example 2

Solid Phase Synthesis of a Single Compound

STEP 1) 1,3-Diaminopropane trityl resin (Novabiochem, 1.2 mmol/g) (0.20 g, 0.24 mmol) was weighed into a screw-cap vial and 3 mL of a 1:1 mixture of DMF and chloroform was added. DIEA (0.130 mL, 0.72 mmol) and 2-(1'-bromopropyl)-3-benzylquinazolin-4-one (from Example 1) (0.188 g, 0.48 mmol) were added. The vial was sealed, heated to 70° C. and shaken overnight. The resin was filtered and washed (3×DCM, 2×MeOH, 1×DCM, 2×ether) and dried under vacuum. A 27 mg aliquot of resin was treated with 5:5:90 TFA:TES:DCM for 15 min and the mixture was filtered and evaporated, resulting in 8 mg (64% yield) of the quinazolinone-diamine intermediate. LCMS analysis showed >80% purity.

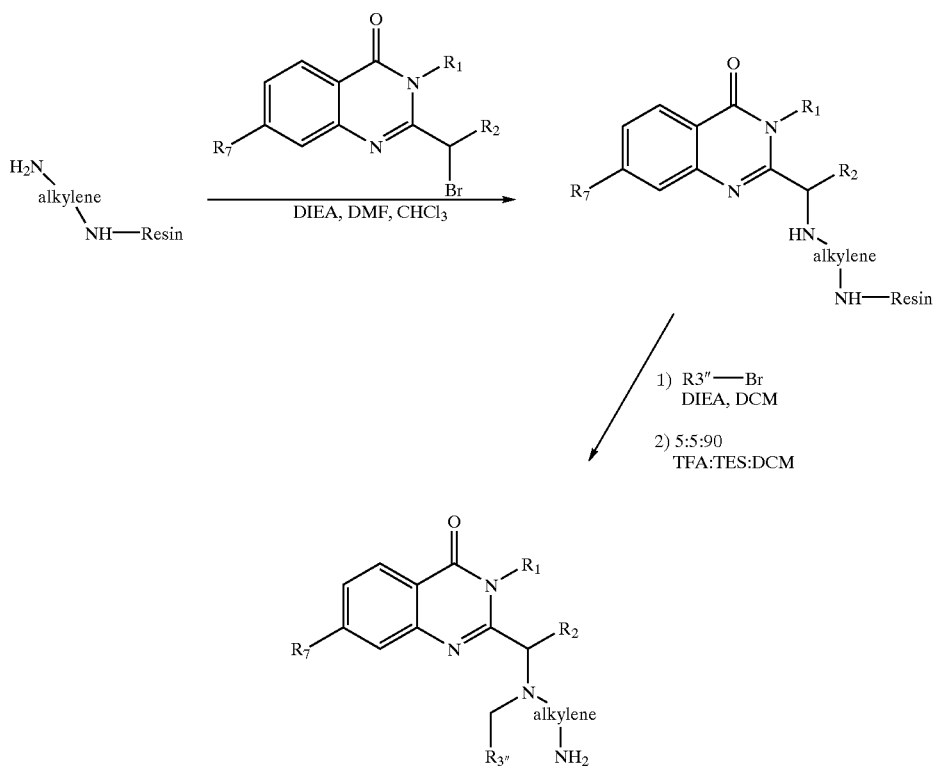

All anhydrous solvents were purchased from Aldrich chemical company in SureSeal® containers. Most reagents were purchase from Aldrich Chemical Company. Abbreviations: DCM, dichloromethane; DIEA, N,N-diisopropylethylamine; DMF, N,N-dimethylformamide; TES, triethylsilane; TFA, trifluoroacetic acid. Array synthesis was conducted in 15×75 mm glass round bottom screw-cap vials contained in a 4×6 array aluminum synthesis block, sealed with a Teflon-lined rubber membrane. Reagents were added and aqueous extractions performed with single or STEP 2) The resin from Step 1 was swelled in 3 mL of DCM. DIEA (0.130 mL, 0.72 mmol) and 4-bromobenzyl bromide (0.12 g, 0.48 mmol) were added. The vial was sealed and shaken overnight. LCMS analysis of a cleaved aliquot revealed an approximate 1:1 mixture of starting material and product. Another 0.130 mL of DIEA and 0.12 g of 4-bromobenzyl bromide were added and the mixture was shaken at 70° C. for 8 h. The resin was filtered, washed (as above), and dried under vacuum.

STEP 3) The resin from Step 2 was twice shaken for 30 min with 5:5:90 TFA:TES:DCM and filtered. The filtrates were combined and evaporated, yielding 140 mg of an orange oil. This material was purified by reverse phase preparative HPLC (acetonitrile-water gradient) to provide 27 mg (17% for 3 steps) of the mono-TFA salt.

Example 3

Combinatorial Synthesis of Multiple Compounds

STEP 1) 1,2-Diaminoethane trityl resin (Novabiochem, 0.95 mmol/g) (200 g, 1.9 mmol) and 1,3-Diaminopropane trityl resin (Novabiochem, 1.14 mmol/g) (2.0 g, 2.28 mmol) were each placed in different 10 mL polypropylene fritted tubes (Bio-Rad). To each were added 4 mL of DMF, 4 mL of chloroform, 3 eq. of DIEA (1.0 mL and 1.2 mL, respectively) and 2 eq. of 2-(1'-bromopropyl)-3-benzylquinazolin-4-one (from Example 1) (1.5 g and 1.8 g, respectively). The mixtures were shaken at 70° C. overnight. Each mixture was washed (3×DCM, 2×MeOH, 1×DCM, 2×ether) and dried under vacuum. Analysis of a cleaved aliquot revealed the presence of the appropriate quinazolinone-diamine for each in >90% purity.

STEP 2) The quinazolinone ethyl-diamine resin (105 mg, 0.10 mmol) was placed into each of the vials in the first 2 rows of the array, and the quinazolinone propyl-diamine resin (88 mg, 0.10 mmol) was placed into each vial of the last 2 rows of the array. To each vial was added DIEA (0.131 mL, 0.75 mmol). Into each vial of the first 2 rows of the array was added a different amine, and the additions were repeated for the last two rows of the array. The reaction block was shaken at 70° C. overnight. Liquid was removed from each vial by multichannel pipette using fine-pointed gel-well tips, and the resins were washed (2×DCM, 1×MeOH, 1×DCM) and dried under vacuum.

STEP 3) To each vial of the array was added 2 mL of a 10:5:85 TFA:TES:DCM solution. The reaction block was shaken for 45 min and the mixtures were transferred to a filter block, filtered, and washed twice with 0.75 mL DCM. The solutions were evaporated to yield yellow-to-red oils. These thick oils were triturated twice with ether, dissolved in DCM and treated with 4 M HCl in dioxane to provide the HCl salts (unknown number of salts per compound) as tan-to-white powdery or amorphous solids. Analysis by LCMS showed all to be >75% pure.

Examples 4–6

Six racemic quinazolinones were separated into their enantiomers by chiral chromatography. The chiral chromatography of three of these compounds is described below:

Example 4

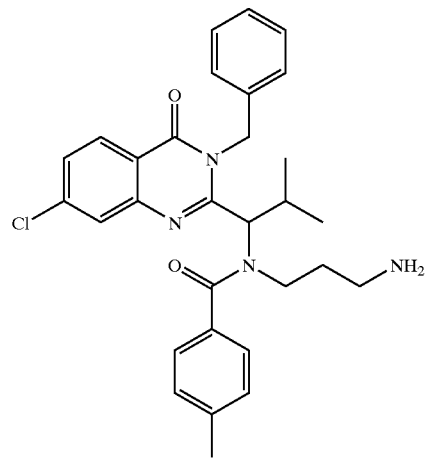

Column—Chiralpak AD, 250×4.6 mm (Diacel Inc.). Sample—0.5 mg/mL in EtOH. Conditions—15 min at 60% EtOH in Hexane, enantiomer 1 elutes at 4.5 min, nantiomer 2 elutes at 4.9 min.

Example 5

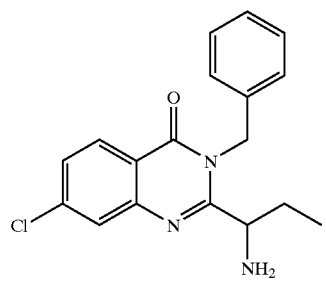

Column—Chiralcel OJ, 250×4.6 mm (Diacel Inc.). Sample—0.5 mg/mL in EtOH. Conditions—15 min at 10% EtOH in Hexane, (R)-enantiomer elutes at 8.4 min, (S)-enantiomer elutes at 9.6 min.

Example 6

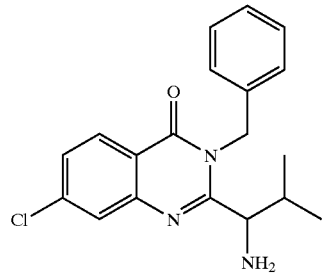

Column—Chiralpak AD, 250×4.6 mm (Diacel Inc.). Sample—0.5 mg/mL in EtOH. Conditions—15 min at 70% EtOH in Hexane, enantiomer 1 elutes at 6.5 min, enantiomer 2 elutes at 8.8 min.

The table below depicts the $IC_{50}$ activity of the racemate and the enantiomers of three other compounds separated as above. In all three cases, one enantiomer was significantly more potent than the other. By independent chiral synthesis, it appears that the more active enantiomer is the R enantiomer.

| | IC$_{50}$ ($\mu$M) Racemate | IC$_{50}$ ($\mu$M) Enantiomer 1 | IC$_{50}$ ($\mu$M) Enantiomer 2 |
|---|---|---|---|
| *[structure: 3-benzyl-2-[1-(N-(2-dimethylaminoethyl)-4-bromobenzamido)propyl]quinazolin-4(3H)-one]* | 0.06 | 0.28 | 0.03 |
| *[structure: 3-benzyl-2-[1-(N-(2-dimethylaminoethyl)-1-naphthamido)propyl]quinazolin-4(3H)-one]* | 12.7 | >>40 | 6.6 |
| *[structure: 3-benzyl-2-[1-(N-(2-dimethylaminoethyl)-4-bromobenzamido)ethyl]quinazolin-4(3H)-one]* | 2.6 | >>40 | 1.3 |

Examples 7 and 8

The following two compounds were synthesized as single enantiomers by the route shown in FIG. 4. The data indicate that the more active enantiomer is the R enantiomer.

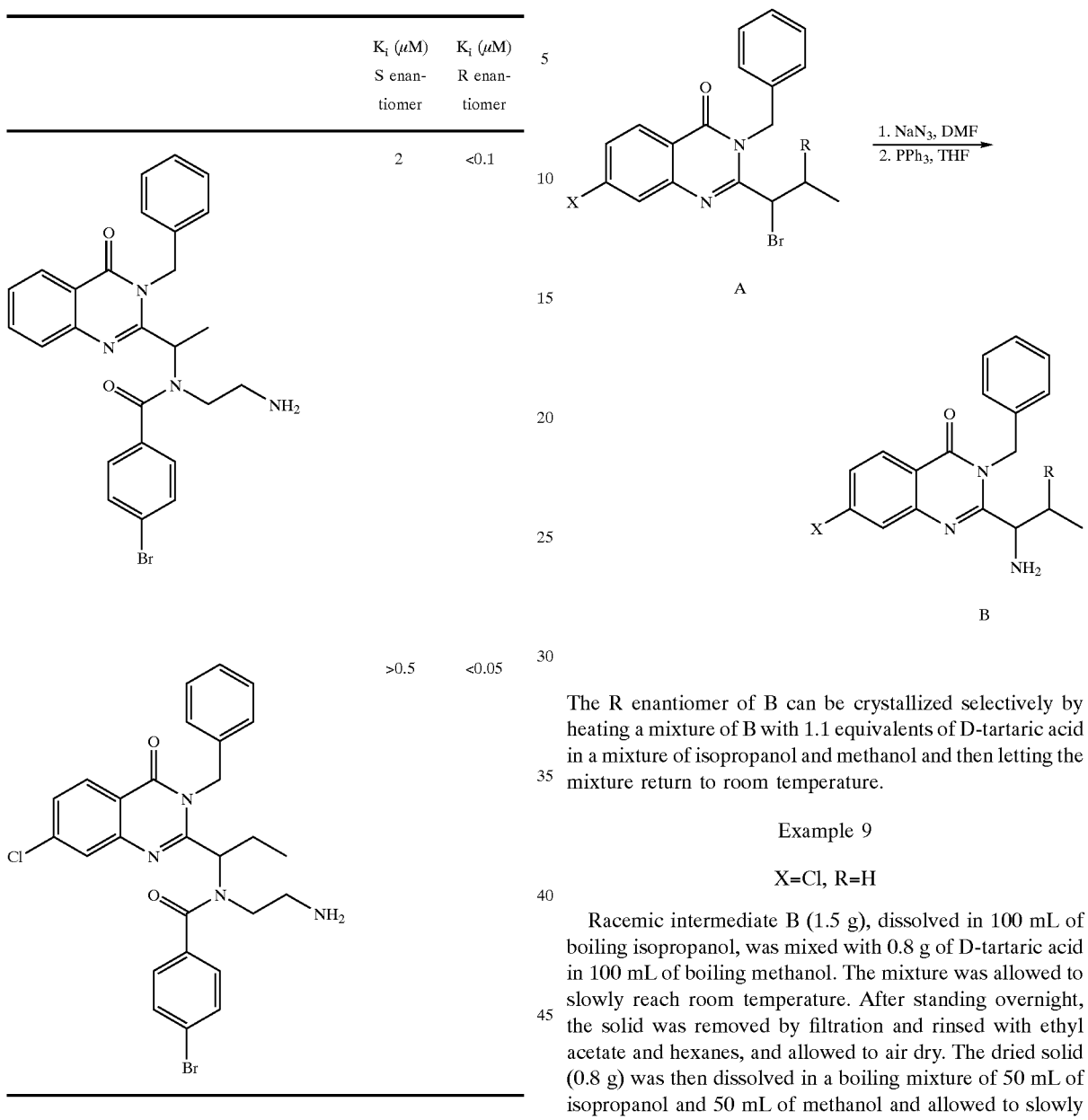

| | $K_i$ (μM) S enantiomer | $K_i$ (μM) R enantiomer |
|---|---|---|
| (structure) | 2 | <0.1 |
| (structure) | >0.5 | <0.05 |

Example 9

Chiral Resolution by Recrystallization with Tartaric Acid

Intermediate A, prepared in Example 1, can be converted to an intermediate B, which, upon resolution, provides an alternative to the first five steps shown in FIG. 4. The process is shown in the scheme below:

The R enantiomer of B can be crystallized selectively by heating a mixture of B with 1.1 equivalents of D-tartaric acid in a mixture of isopropanol and methanol and then letting the mixture return to room temperature.

Example 9

X=Cl, R=H

Racemic intermediate B (1.5 g), dissolved in 100 mL of boiling isopropanol, was mixed with 0.8 g of D-tartaric acid in 100 mL of boiling methanol. The mixture was allowed to slowly reach room temperature. After standing overnight, the solid was removed by filtration and rinsed with ethyl acetate and hexanes, and allowed to air dry. The dried solid (0.8 g) was then dissolved in a boiling mixture of 50 mL of isopropanol and 50 mL of methanol and allowed to slowly cool to room temperature. After standing overnight, the resulting solid was removed by filtration and rinsed with ethyl acetate and hexanes, and allowed to air dry. The dried solid was then stirred with saturated sodium bicarbonate for 30 min and extracted with ethyl acetate. The organics were dried ($MgSO_4$), filtered and evaporated to dryness. The resulting clear oil weighed 345 mg. Chiral purity of >95% was determined by conversion of a portion to the S-Mosher amide and examination of the product by $^1$HNMR. The enantiomerically pure compounds below were prepared, according to the remaining steps in FIG. 4, from material resulting from the procedure described above using both D- and L-tartaric acid.

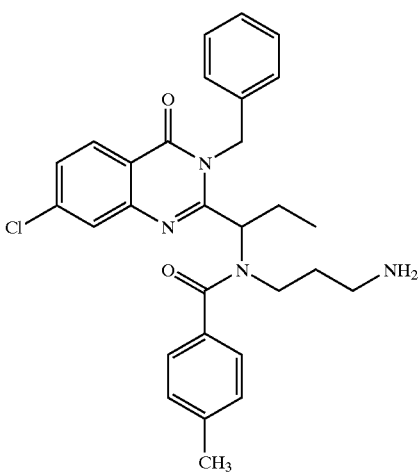

| | Racemic I C$_{50}$ (uM) | R Isomer IC$_{50}$ (uM) | S Isomer IC$_{50}$ (uM) |
|---|---|---|---|
| | <0.05 | <0.05 | >0.5 |

Induction of Mitotic Arrest in Cell Populations Treated with a Quinazolinone KSP Inhibitor FACS analysis to determine cell cycle stage by measuring DNA content was performed as follows. Skov-3 cells (human ovarian cancer) were split 1:10 for plating in 10 cm dishes and grown to subconfluence with RPMI 1640 medium containing 5% fetal bovine serum (FBS). The cells were then treated with either 10 nM paclitaxel, 400 nM quinazolinone 1, 200 nM quinazolinone2, or 0.25% DMSO (vehicle for compounds) for 24 hours. Cells were then rinsed off the plates with PBS containing 5 mM EDTA, pelleted, washed once in PBS containing 1% FCS, and then fixed overnight in 85% ethanol at 4° C. Before analysis, the cells were pelleted, washed once, and stained in a solution of 10 μg propidium iodide and 250 kg of ribonuclease (RNAse) A per milliliter at 37° C. for half an hour. Flow cytometry analysis was performed on a Becton-Dickinson FAC Scan, and data from 10,000 cells per sample was analyzed with Modfit software.

The quinazolinone compounds, as well as the known anti-mitotic agent paclitaxel, caused a shift in the population of cells from a G0/G1 cell cycle stage (2n DNA content) to a G2/M cell cycle stage (4n DNA content). Other compounds of this class were found to have similar effects.

Monopolar Spindle Formation Following Application of a Quinazolinone KSP Inhibitor To determine the nature of the G2/M accumulation, human tumor cell lines Skov-3 (ovarian), HeLa (cervical), and A549 (lung) were plated in 96-well plates at densities of 4,000 cells per well (SKOV-3 & HeLa) or 8,000 cells per well (A549), allowed to adhere for 24 hours, and treated with various concentrations of the quinazolinone compounds for 24 hours. Cells were fixed in 4% formaldehyde and stained with anti-tubulin antibodies (subsequently recognized using fluorescently-labeled secondary antibody) and Hoechst dye (which stains DNA).

Visual inspection revealed that the quinazolinone compounds caused cell cycle arrest in the prometaphase stage of mitosis. DNA was condensed and spindle formation had initiated, but arrested cells uniformly displayed monopolar spindles, indicating that there was an inhibition of spindle pole body separation. Microinjection of anti-KSP antibodies also causes mitotic arrest with arrested cells displaying monopolar spindles.

Inhibition of Cellular Proliferation in Tumor Cell Lines Treated with Quinazolinone KSP Inhibitors Cells were plated in 96-well plates at densities from 1000–2500 cells/well of a 96-well plate (depending on the cell line) and allowed to adhere/grow for 24 hours. They were then treated with various concentrations of drug for 48 hours. The time at which compounds are added is considered $T_0$. A tetrazolium-based assay using the reagent 3-(4,5-dimethylthiazol-2-yl)-5-(3-carboxymethoxyphenyl)-2-(4-sulfophenyl)-2H-tetrazolium (MTS) (I.S>U.S. Pat. No. 5,185,450) (see Promega product catalog #G3580, CellTiter 96®) AQ$_{ueous}$ One Solution Cell Proliferation Assay) was used to determine the number of viable cells at $T_0$ and the number of cells remaining after 48 hours compound exposure. The number of cells remaining after 48 hours was compared to the number of viable cells at the time of drug addition, allowing for calculation of growth inhibition.

The growth over 48 hours of cells in control wells that had been treated with vehicle only (0.25% DMSO) is considered 100% growth and the growth of cells in wells with compounds is compared to this. Quinazolinone KSP inhibitors inhibited cell proliferation in human tumor cell lines of the following tumor types: lung (NCI-H460, A549), breast (MDA-MB-231, MCF-7, MCF-7/ADR-RES), colon (HT29, HCT15), ovarian (SKOV-3, OVCAR-3), leukemia (HL-60 (TB), K-562), central nervous system (SF-268), renal (A498), osteosarcoma (U2-OS), and cervical (HeLa). In addition, a mouse tumor line (B16, melanoma) was also growth-inhibited in the presence of the quinazolinone compounds.

A Gi$_5$, was calculated by plotting the concentration of compound in μM vs the percentage of cell growth of cell growth in treated wells. The Gi$_{50}$ calculated for the compounds is the estimated concentration at which growth is inhibited by 50% compared to control, i.e., the concentration at which:

$100\times[(\text{Treated}_{48}-T_0)/(\text{Control}_{48}-T_0)]=50.$

All concentrations of compounds are tested in duplicate and controls are averaged over 12 wells. A very similar 96-well plate layout and $GI_5$ calculation scheme is used by the National Cancer Institute (see Monks, et al., J. Natl. Cancer Inst. 83:757–766 (1991)). However, the method by which the National Cancer Institute quantitates cell number does not use MTS, but instead employs alternative methods.

Calculation of $IC_{50}$

Measurement of a composition's $IC_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM IDTT (Sigma D-9779), 5 μM paclitaxel (Sigma T-7402), 10 ppm antifoam 289 (Sigma A-8436), 25 mM Pipes/KOH pH 6.8 (Sigma P6757), 2 mM MgCl2 (VWR JT400301), and 1 mM EGTA (Sigma E3889). Solution 2 consists of 1 mM NADH (Sigma N8129), 0.2 mg/ml BSA (Sigma A7906), pyruvate kinase 7 U/ml, L-lactate dehydrogenase 10 U/ml (Sigma P0294), 100 nM KSP motor domain, 50 pg/ml microtubules, 1 mM DTT (Sigma D9779), 5 μM paclitaxel (Sigma T-7402), 10 ppm antifoam 289 (Sigma A-8436), 25 mM Pipes/KOH pH 6.8 (Sigma P6757), 2 mM MgCl2 (VWR JT4003-01), and 1 mM EGTA (Sigma E3889). Serial dilutions (8–12 two-fold dilutions) of the composition are made in a 96-well microtiter plate (Corning Costar 3695) using Solution 1. Following serial dilution each well has 50 μl of Solution 1. The reaction is started by adding 50 μl of solution 2 to each well. This may be done with a multichannel pipettor either manually or with automated liquid handling devices. The microtiter plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{Range}{1+\left(\frac{x}{IC_{50}}\right)^s} + Background$$

Where y is the observed rate and x the compound concentration.

The quinazolinone compounds inhibit growth in a variety of cell lines, including cell lines (MCF-7/ADR-RES, HCT1 5) that express P-glycoprotein (also known as Multi-drug Resistance, or MDR+), which conveys resistance to other chemotherapeutic drugs, such as paclitaxel. Therefore, the quinazolinones are anti-mitotics that inhibit cell proliferation, and are not subject to resistance by overexpression of MDR+ by drug-resistant tumor lines.

Other compounds of this class were found to inhibit cell proliferation, although $GI_{50}$ values varied. $GI_{50}$ values for the quinazolinone compounds tested ranged from 200 nM to greater than the highest concentration tested. By this we mean that although most of the compounds that inhibited KSP activity biochemically did inhibit cell proliferation, for some, at the highest concentration tested (generally about 20 μM), cell growth was inhibited less than 50%. Many of the compounds have $GI_{50}$ values less than 10 μM, and several have $GI_{50}$ values less than 1 μM. Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 μM, and hydroxyurea is 500 μM (data provided by National Cancer Institute, Developmental Therapeutic Program, http://dtp.nci.nih.gov/). Therefore, compounds that inhibit cellular proliferation at virtually any concentration may be useful. However, preferably, compounds will have $GI_{50}$ values of less than 1 mM. More preferably, compounds will have $GI_{50}$ values of less than 20 μM. Even more preferably, compounds will have $GI_{50}$ values of less than 10 μM. Further reduction in $GI_{50}$ values may also be desirable, including compounds with $GI_{50}$ values of less than 1 μM. Some of the quinazolinone compounds of the invention inhibit cell proliferation with $GI_{50}$ values from below 200 nM to below 10 nM.

We claim:

1. A compound of a formula:

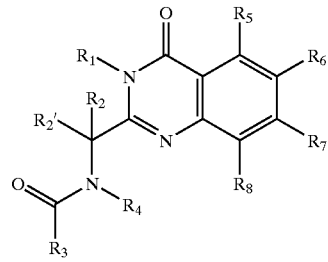

wherein $R_1$ is benzyl; $R_2$ is ethyl; $R_2'$ is hydrogen; $R_3$ is p-tolyl; $R_4$ is 3-(isopropylamino)propyl; $R_5$, $R_6$, and $R_8$ are hydrogen; and $R_7$ is chloro;

$R_1$ is p-chlorobenzyl; $R_2$ is ethyl; $R_2'$ is hydrogen; $R_3$ is p-bromophenyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-(dimethylamino)propyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-aminopropyl; $R_5$, $R_6$, and $R_8$ are hydrogen; and $R_7$ is chloro;

$R_1$ is m-methoxybenzyl; $R_2$ is ethyl; $R_2'$ is hydrogen; $R_3$ is p-tolyl; $R_4$ is 3-aminopropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 3-aminopropyl; $R_5$, $R_6$, and $R_8$ are hydrogen; and $R_7$ is chloro;

$R_1$ is benzyl; $R_2$ is isopropyl; $R_2'$ is hydrogen; $R_3$ is p-tolyl; $R_4$ is 3-aminopropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is azetidin-3-ylmethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-aminoethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 2-aminoethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-aminopropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-(methylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 3-(methylamino)propyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 2-(methylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is azetidin-2-ylmethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 3-aminopropyl; $R_5$, $R_6$, and $R_8$ are hydrogen; and $R_7$ is chloro;

$R_1$ is benzyl; $R_2$ is methylsulfinylmethyl; $R_2'$ is hydrogen; $R_3$ is p-toyl; $R_4$ is 3-aminopropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is piperidin-3-ylmethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-aminopropyl; $R_5$, $R_6$, and $R_8$ are hydrogen; and $R_7$ is fluoro;

$R_1$ is benzyl; $R_2$ is ethyl; $R_2'$ is hydrogen; $R_3$ is p-bromophenyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-aminoethyl; $R_5$, $R_6$, $R_7$ and $R_8$ are hydrogen;

$R_1$ is benzyl; $R_2$ is ethyl; $R_2'$ is hydrogen; $R_3$ is p-tolyl; $R_4$ is piperidin-2-yl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 4-aminobutyl; $R_5$, $R_6$, and $R_8$ are hydrogen; and $R_7$ is chloro;

$R_1$ is m-chlorobenzyl; $R_2$ is ethyl; $R_2'$ is hydrogen; $R_3$ is p-bromophenyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-(piperidin-1-yl)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-(imidazol-3-yl)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is pyrrolidin-3-ylmethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 2-(diethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-chlorophenyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 4-aminobutyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is pyrrolidin-2-ylmethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-(azetidin-1-yl)propyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-(pyrrolidin-1-yl)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-(pyrrolidin-1-yl)propyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 3-(dimethylamino)propyl; $R_5$, $R_6$, and $R_8$ are hydrogen; and $R_7$ is chloro;

$R_1$ is benzyl; $R_2$ is propyl; $R_2'$ is hydrogen; $R_3$ is p-bromophenyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 2-(pyrrolidin-1-yl)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 3-(pyrrolidin-1-yl)propyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is piperidin-4-ylmethyl; $R_5$, $R_6$, and $R_8$ are hydrogen; and $R_7$ is chloro;

$R_1$ is benzyl; $R_2$ is methylsulfinylethyl; $R_2'$ is hydrogen; $R_3$ is p-tolyl; $R_4$ is 3-aminopropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-(piperidin-1-yl)propyl; $R_5$, $R_6$, and $R_8$ are hydrogen; and $R_7$ is chloro;

$R_1$ is benzyl; $R_2$ is benzyl; $R_2'$ is hydrogen; $R_3$ is p-tolyl; $R_4$ is 3-aminopropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is (N-ethylpyrrolidin-2-yl)methyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-piperidinyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 4-piperidinyl; $R_5$, $R_6$, and $R_8$ are hydrogen; and $R_7$ is chloro;

$R_1$ is p-chlorobenzyl; $R_2$ is ethyl; $R_2'$ is hydrogen; $R_3$ is p-bromophenyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 2,2-dimethyl-3-(dimethylamino)propyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 5-aminopentyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-(dimethylamino)propyl; $R_5$, $R_6$, and $R_8$ are hydrogen; and $R_7$ is fluoro;

$R_1$ is benzyl; $R_2$ is ethyl; $R_2'$ is hydrogen; $R_3$ is p-bromophenyl; $R_4$ is 3-(2-methylpiperidin-1-yl)propyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-(dimethylamino)ethyl; $R_5$, $R_6$, and $R_8$ are hydrogen; and $R_7$ is fluoro;

$R_1$ is benzyl; $R_2$ is ethyl; $R_2'$ is hydrogen; $R_3$ is p-bromophenyl; $R_4$ is 2-(N-methylpyrrolidin-2-yl)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-trifluoromethylphenyl; $R_4$ is 3-(dimethylamino)propyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 3-(diethylamino)propyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 3-(N-methylpiperazin-1-yl) propyl; $R_5$, $R_6$, and $R_8$ are hydrogen; and $R_7$ is chloro;

$R_1$ is benzyl; $R_2$ is 4-(CBZ)aminobutyl; $R_2'$ is hydrogen; $R_3$ is p-tolyl; $R_4$ is 3-aminopropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is aminoethoxyethyl; $R_5$, $R_6$, and $R_8$ are hydrogen; and $R_7$ is chloro;

$R_1$ is benzyl; $R_2$ is ethyl; $R_2'$ is hydrogen; $R_3$ is 2-naphthyl; $R_4$ is 2-(dimethylamino)ethyl; $R_5$, $R_6$, and $R_8$ are hydrogen; and $R_7$ is chloro $R_1$ is benzyl; $R_2$ is cyclohexylmethyl; $R_2'$ is hydrogen; $R_3$ is p-tolyl; $R_4$ is 3-aminopropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 2-(piperidin-1-yl)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 3-hydroxypropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-fluorophenyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 6-aminohexyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-(dimethylamino)ethyl; $R_5$, $R_7$, and $R_8$ are hydrogen; and $R_6$ is chloro;

$R_1$ is benzyl; $R_2$ is ethyl; $R_2'$ is hydrogen; $R_3$ is p-bromophenyl; $R_4$ is 2-(dimethylamino)ethyl; $R_5$, $R_6$, and $R_8$ are hydrogen; and $R_7$ is fluoro;

$R_1$ is benzyl; $R_2$ is methyl; $R_2'$ is hydrogen; $R_3$ is p-bromophenyl; $R_4$ is 2-aminoethyl; $R_5$, $R_6$, $R_7$ and $R_8$ are hydrogen;

$R_1$ is benzyl; $R_2$ is ethyl; $R_2'$ is hydrogen; $R_3$ is p-tolyl; $R_4$ is 2-(dimethylamino)ethyl; $R_5$, $R_6$, and $R_7$ are hydrogen; and $R_8$ is chloro;

$R_1$ is benzyl; $R_2$ is ethyl; $R_2'$ is hydrogen; $R_3$ is p-bromophenyl; $R_4$ is 2-(dimethylamino)ethyl; $R_6$, $R_7$, and $R_8$ are hydrogen; and $R_5$ is chloro;

$R_1$ is benzyl; $R_2$ is aminobutyl; $R_2'$ is hydrogen; $R_3$ is p-tolyl; $R_4$ is 3-aminopropyl; $R_5$, $R_6$, and $R_8$ are hydrogen; and $R_7$ is chloro;

$R_1$ is benzyl; $R_2$ is ethyl; $R_2'$ is hydrogen; $R_3$ is p-tolyl; $R_4$ is 2-(dimethylamino)ethyl; $R_5$ and $R_8$ are hydrogen; and $R_6$ and $R_7$ are fluoro;

$R_1$ is m-tolyl; $R_2$ is ethyl; $R_2'$ is hydrogen; $R_3$ is p-bromophenyl; $R_4$ is 2-(dimethylamino)ethyl; $R_5$, $R_6$, and $R_8$ are hydrogen; and $R_7$ is chloro;

$R_1$ is benzyl; $R_2$ is ethyl; $R_2'$ is hydrogen; $R_3$ is p-bromophenyl; $R_4$ is 2-(dimethylamino)ethyl; $R_5$ and $R_8$ are hydrogen; and $R_6$ and $R_7$ are fluoro; or $R_1$ is benzyl; $R_2$ is ethyl; $R_2'$ is hydrogen; $R_3$ is p-bromophenyl; $R_4$ is 2-carboxyethyl; $R_5$, $R_6$, and $R_8$ are hydrogen; and $R_7$ is chloro, or a pharmaceutically acceptable salt of any of the foregoing compounds.

2. A compound according to claim 1 wherein $R_2$ and $R_2'$ are each attached to a stereogenic center having an R-configuration, or a pharmaceutically acceptable salt thereof.

3. A salt of the formula

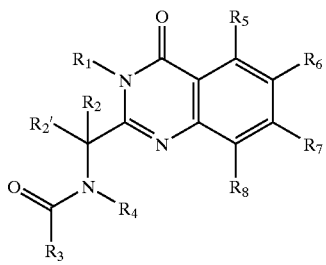

wherein
$R_1$ is benzyl;
$R_2$ is isopropyl;
$R_2'$ is hydrogen;
$R_3$ is p-tolyl;
$R_4$ is 3-aminopropyl;
$R_5$ is hydrogen;
$R_6$ is hydrogen;
$R_7$ is chloro; and
$R_8$ is hydrogen; and wherein
said salt is a mesylate.

4. A compound of formula:
wherein:
$R_1$ is benzyl or halobenzyl;
$R_2$ ethyl or propyl;
$R_2'$;
$R_3$ is substituted phenyl;
$R_4$ is —$(CH_2)_m$OH or —$(CH_2)_p R_{16}$ wherein m is two or three and p is one to three;
$R_5$ is hydrogen;
$R_6$ hydrogen;
$R_7$ is halo;
$R_8$ is hydrogen; and
$R_{16}$ is chosen from amino, propylamino, and azetidinyl;
or a pharmaceutically acceptable salt thereof.

5. A compound according to claim 4 wherein $R_3$ is phenyl substituted with one or more halo, lower alkyl, lower alkoxy, nitro, carboxy, methylenedioxy, or trifluoromethyl, or a pharmaceutically acceptable salt thereof.

6. A compound according to claim 4 wherein $R_2$ and $R_2'$ are each attached to a stereogenic center having an R-configuration, or a pharmaceutically acceptable salt thereof.

7. A compound according to claim 4, wherein
$R_1$ is benzyl;
$R_2$ is isopropyl;
$R_2'$ is hydrogen;
$R_3$ is p-tolyl;
$R_4$ is 3-aminopropyl;
$R_5$ is hydrogen;
$R_6$ is hydrogen;
$R_7$ is chloro; and
$R_8$ is hydrogen;
or a pharmaceutically acceptable salt thereof.

8. A salt according to claim 7, wherein said salt is a mesylate.

9. A composition comprising a pharmaceutically acceptable excipient and a compound or salt of claim 1, 4, or 3.

10. A compound according to claim 5 wherein $R_2$ and $R_{2'}$ are each attached to a stereogenic center having an R-configuration, or a pharmaceutically acceptable salt thereof.

11. A compound according to claim 7 wherein $R_2$ and $R_{2'}$ are each attached to a stereogenic center having an R-configuration, or a pharmaceutically acceptable salt thereof.

12. A composition comprising a pharmaceutically acceptable excipient and a compound or salt of claim 5.

13. A composition according to claim 12, wherein said composition further comprises a taxane.

14. A composition according to claim 12, wherein said composition further comprises a vinca alkaloid.

15. A composition according to claim 12, wherein said composition further comprises a topoisomerase I inhibitor.

16. A composition comprising a pharmaceutically acceptable excipient and a compound or salt of claim 7.

17. A composition according to claim 16, wherein said composition further comprises a taxane.

18. A composition according to claim 16, wherein said composition further comprises a vinca alkaloid.

19. A composition according to claim 16, wherein said composition further comprises a topoisomerase I inhibitor.

20. A composition according to claim 9, wherein said composition further comprises a taxane.

21. A composition according to claim 9, wherein said composition further comprises a vinca alkaloid.

22. A composition according to claim 9, wherein said composition further comprises a topoisomerase I inhibitor.

* * * * *

UNITED STATES PATENT AND TRADEMARK OFFICE
CERTIFICATE OF CORRECTION

PATENT NO. : 6,545,004 B1
APPLICATION NO. : 09/699047
DATED : April 8, 2003
INVENTOR(S) : Jeffrey T. Finer et al.

It is certified that error appears in the above-identified patent and that said Letters Patent is hereby corrected as shown below:

On the title page, item (57), second structure

"
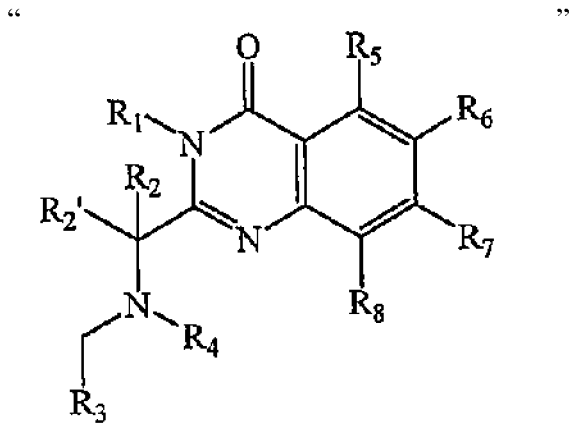
"

should read

--
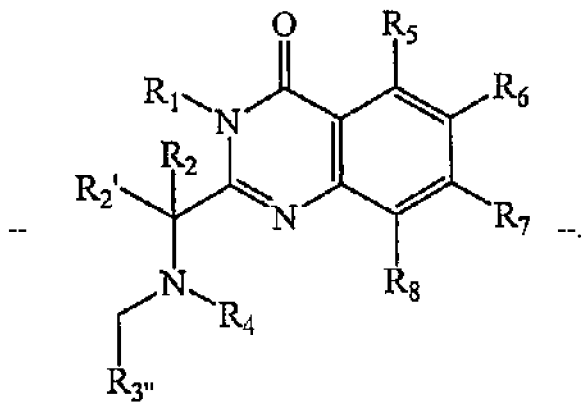
--.

UNITED STATES PATENT AND TRADEMARK OFFICE
CERTIFICATE OF CORRECTION

PATENT NO. : 6,545,004 B1
APPLICATION NO. : 09/699047
DATED : April 8, 2003
INVENTOR(S) : Jeffrey T. Finer et al.

It is certified that error appears in the above-identified patent and that said Letters Patent is hereby corrected as shown below:

On the title page, item (57), Thrid Structure

"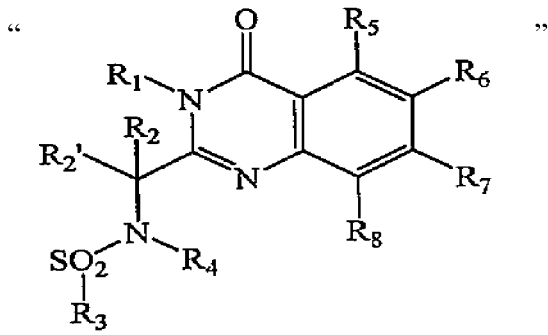"

should read

-- 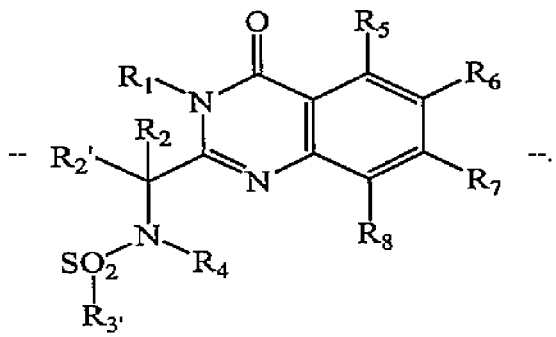 --.

Col. 3, lines 45-55,

"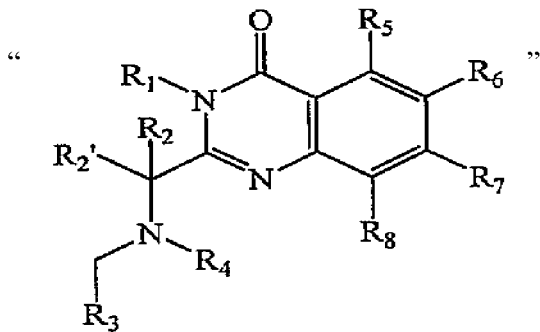"

UNITED STATES PATENT AND TRADEMARK OFFICE
CERTIFICATE OF CORRECTION

PATENT NO. : 6,545,004 B1
APPLICATION NO. : 09/699047
DATED : April 8, 2003
INVENTOR(S) : Jeffrey T. Finer et al.

It is certified that error appears in the above-identified patent and that said Letters Patent is hereby corrected as shown below:

should read

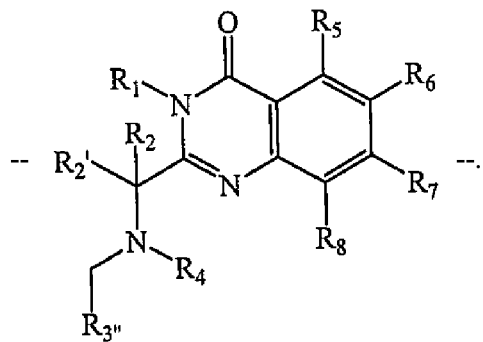

Col. 3, lines 57-67,

"
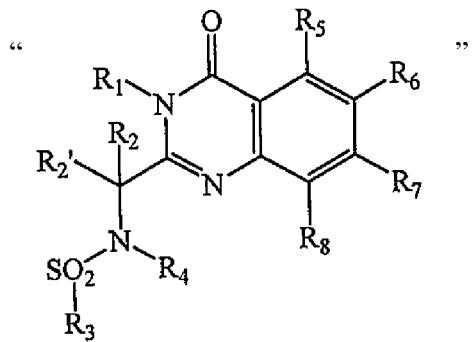
"

should read

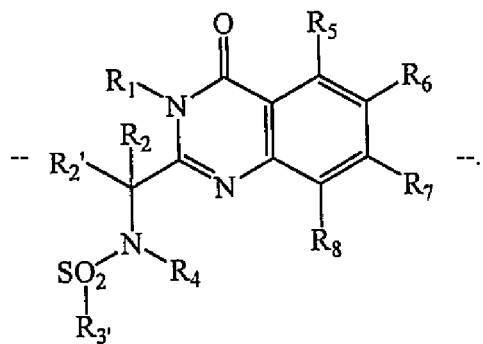

UNITED STATES PATENT AND TRADEMARK OFFICE
CERTIFICATE OF CORRECTION

PATENT NO. : 6,545,004 B1  
APPLICATION NO. : 09/699047  
DATED : April 8, 2003  
INVENTOR(S) : Jeffrey T. Finer et al.

It is certified that error appears in the above-identified patent and that said Letters Patent is hereby corrected as shown below:

Col. 6, lines 15-25,

"
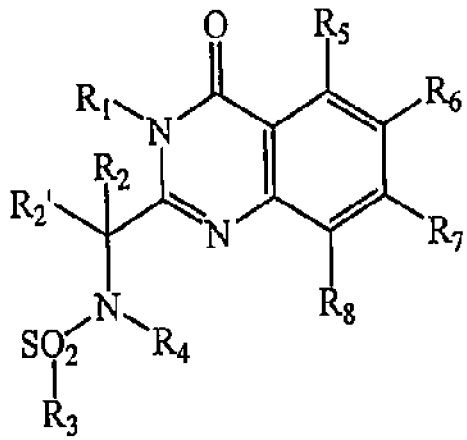
"

should read

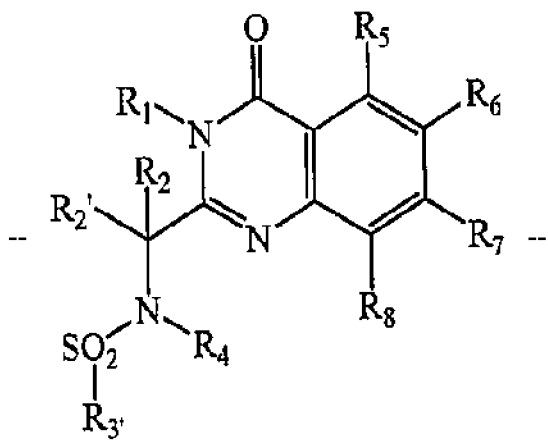

Col. 11, line 24, "$R_3$ is substituted phenyl" (second occurrence) should read --$R_{3'}$ is substituted phenyl--.

UNITED STATES PATENT AND TRADEMARK OFFICE
CERTIFICATE OF CORRECTION

PATENT NO. : 6,545,004 B1
APPLICATION NO. : 09/699047
DATED : April 8, 2003
INVENTOR(S) : Jeffrey T. Finer et al.

It is certified that error appears in the above-identified patent and that said Letters Patent is hereby corrected as shown below:

Col. 23, lines 24-57,

"

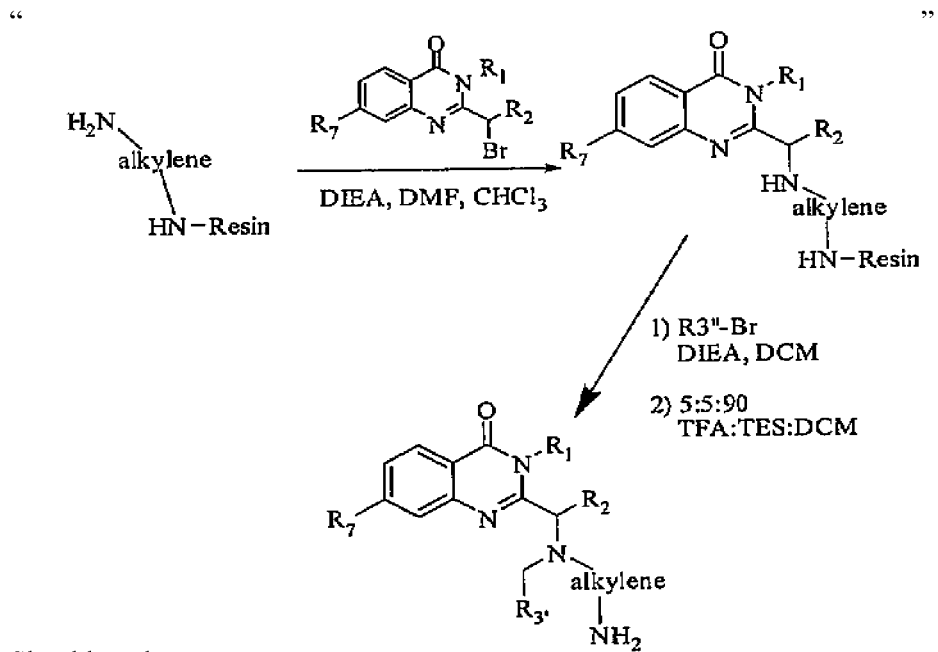

Should read

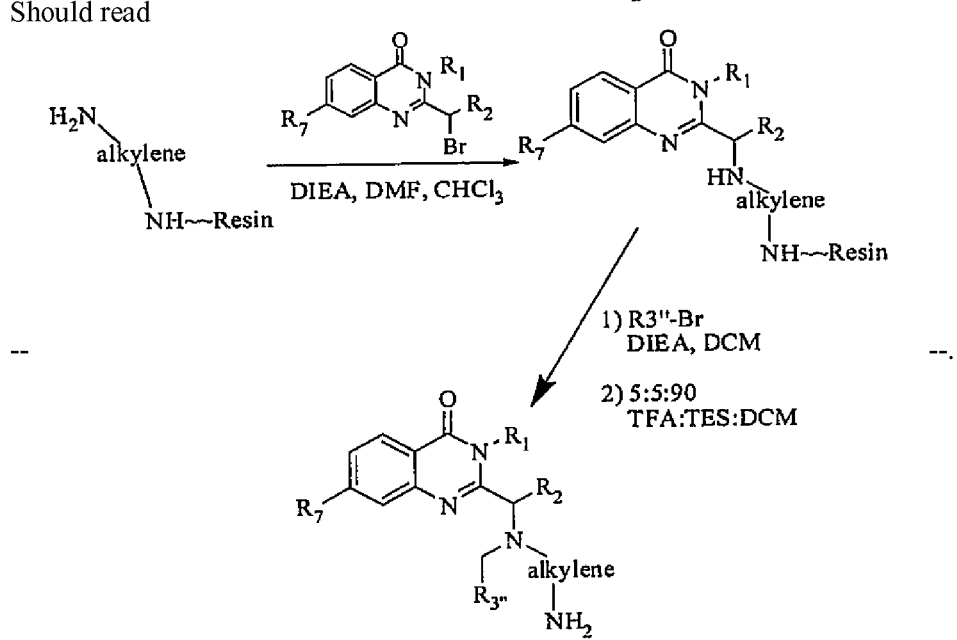

--                                                                                                                                                             --.

"

UNITED STATES PATENT AND TRADEMARK OFFICE
CERTIFICATE OF CORRECTION

PATENT NO.         : 6,545,004 B1
APPLICATION NO. : 09/699047
DATED               : April 8, 2003
INVENTOR(S)       : Jeffrey T. Finer et al.

It is certified that error appears in the above-identified patent and that said Letters Patent is hereby corrected as shown below:

Col. 31, line 41, "250 kg" should read --250 µg--.

Col. 32, line 62, "$Gi_5$," should read --$Gi_{50}$--.

Col. 33, line 5, "$Gi_5$" should read --$Gi_{50}$--.

Col. 33, line 22, "50 pg/ml" should read --50 µg/ml--.

In claim 4, column 38, line 27, after "formula:" insert

-- 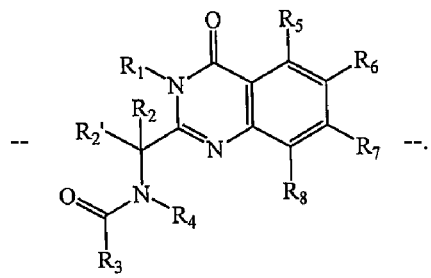 --.

In claim 4, column 38, line 31, "$R_2$ ethyl" should read --$R_2$ is ethyl--.

In claim 4, column 38, line 32, "$R_2$';" should read --$R_2$' is hydrogen;--.

In claim 4, column 38, line 37, "$R_6$ hydrogen;" should read --$R_6$ is hydrogen;--.

Signed and Sealed this

Thirtieth Day of January, 2007

JON W. DUDAS
*Director of the United States Patent and Trademark Office*